US008101350B1

(12) United States Patent
Dobie

(10) Patent No.: US 8,101,350 B1
(45) Date of Patent: Jan. 24, 2012

(54) MODULATION OF EXPORTIN 5 EXPRESSION

(75) Inventor: Kenneth W. Dobie, Delmar, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 11/135,241

(22) Filed: May 23, 2005

Related U.S. Application Data

(60) Provisional application No. 60/574,118, filed on May 24, 2004.

(51) Int. Cl.
*C12Q 1/68* (2006.01)
*C12N 15/11* (2006.01)
*C07H 21/04* (2006.01)

(52) U.S. Cl. ....... 435/6.1; 435/6.11; 536/24.5; 514/44 A

(58) Field of Classification Search .................... 514/44; 435/69.1, 375, 6
See application file for complete search history.

(56) References Cited

U.S. PATENT DOCUMENTS

| | | | | |
|---|---|---|---|---|
| 5,563,255 | A * | 10/1996 | Monia et al. | 536/24.31 |
| 6,165,791 | A * | 12/2000 | Popoff et al. | 435/375 |
| 2003/0228597 | A1* | 12/2003 | Cowsert et al. | 435/6 |
| 2004/0018176 | A1* | 1/2004 | Tolentino et al. | 424/93.21 |
| 2004/0171118 | A1* | 9/2004 | Rossi et al. | 435/69.1 |
| 2005/0014257 | A1* | 1/2005 | Crooke et al. | 435/375 |

OTHER PUBLICATIONS

Patil et al., DNA-based Therapeutics and DNA delivery systems: A comprehensive review, 2005, The AAPS Journal, vol. 7, pp. E61-E77.*
"Significant Technological Challenges Remain for the Development of RNA-based Therapeutics", Feb. 2, 2006, Business Wire, New York, pp. 1-3 of the print-out version are enclosed.*
"Isis says cancer drug failed to show benefit / Late-stage trail sponsored by Lilly", Oct. 28, 2004, The San Diego Union-Tribune, San Diego, California, pp. 1-2 of the print-out version are enclosed.*
Vickers et al., Efficient reduction of target RNAs by small interfering RNA and RNase H-dependent antisense agents, 2003, The Journal of Biological Chemistry, vol. 278, pp. 7108-7118.*
Matveeva et al., Thermodynamic criteria for high hit rate antisense oligonucleotide design, 2003, Nucleic Acids Research, vol. 31, pp. 4989-4994.*
Elbashir et al., Analysis of gene function in somatic mammalian cells using small interfering RNAs, 2002, Methods, vol. 26, pp. 199-213.*
Lassus et al., Confirming specificity of RNAi in mammalian cells, 2002, Science Signaling, The Signal Transduction Knowledge Environment, issue 147, protocol 13, pp. 1-9.*
Amarzguioui et al., Tolerance for mutations and chemical modifications in a siRNA, 2003, Nucleic Acids Research, vol. 31, pp. 589-595.*
GenBank Accession No. AF298880, Version AF2998880.1, Nucleotide-*Homo sapiens* exportin 5 mRNA, complete cds, first submitted on Aug. 24, 2000, date of modification on Jan. 8, 2002, accessed http://www.ncbi.nlm.nih.gov on Jan. 11, 2010, four print-out pages are enclosed.*
Peng et al., Silencing expression of the catalytic subunit of DNA-dependent protein kinase by small interfering RNA sensitizes human cells for radiation-induced chromosome damage, cell killing, and mutation, 2002, Cancer Research, vol. 62, pp. 6400-6404.*
Lee et al., Mammalian APH-1 interacts with presenilin and nicastrin and is required for intramembrane proteolysis of amyloid-beta precursor protein and Notch, 2002, The Journal of Biological Chemistry, vol. 277, pp. 45013-45019.*
Randall et al., Clearance of replicating hepatitis C virus replicon RNAs in cell culture by small interfering RNAs, 2003, PNAS, vol. 100, pp. 235-240.*
Harborth et al., Identification of essential genes in cultured mammalian cells using small intefering RNAs, 2001, Journal of Cell Science, vol. 114, pp. 4557-4565.*
Elbashir et al., Duplexes of 21-nucleotide RNAs mediate RNA interference in cultured mammalian cells, 2001, vol. 411, pp. 494-498.*
Ambros, V. et al., "A uniform system for microRNA annotation," *RNA* (2003) 9:277-279.
Bartel, B. et al., "MicroRNAs: At the Root of Plant Development?" *Plant Physiology* (2003) 132:709-717.
Bohnsack, M. T. et al., "Exp5 exports eEF1A via tRNA from nuclei and synergizes with other transport pathways to confine translation to the cytoplasm," *Embo J.* (2002) 21(22): 6205-6215.
Bohnsack, M. T. et al., "Exportin 5 is a RanGTP-dependent dsRNA-binding protein that mediates nuclear export of pre-miRNAs," *RNA* (2004) 10:185-191.
Bollman, K. M. et al., "HASTY, the *Arabidopsis* ortholog of exportin 5/MSN5, regulates phase change and morphogenesis," *Development* (2003) 130:1493-1504.
Brownawell, A. M. et al., "Exportin-5, a novel karyopherin, mediates nuclear export of double-stranded RNA binding proteins," *J. Cell Biol.* (2002) 156(1):53-64.
Calado, A. et al., "Exportin-5-mediated nuclear export of eukaryotic elongation factor 1A and tRNA," *Embo J.* (2002) 21(22):6216-6224.
Fire, A. et al., "Potent and specific genetic interference by double-stranded RNA in *Caenorhabditis elegans*," *Nature* (1998) 391:806-811.
Guo, S. et al., "*par-1*, a Gene Required for Establishing Polarity in *C. elegans* Embryos, Encodes a Putative Ser/Thr Kinase That Is Asymmetrically Distributed," *Cell* (1995) 81:611-620.
Gwizdek, C. et al., "Exportin-5 Mediates Nuclear Export of Minihelix-containing RNAs," *J. Biol. Chem.* (2003) 278(8):5505-5508.
Gwizdek, C. et al., "Minihelix-containing RNAs Mediate Exportin-5-dependent Nuclear Export of the Double-stranded RNA-binding Protein ILF3," *J. Biol. Chem.* (2004) 279(2):884-891.

(Continued)

*Primary Examiner* — Dana Shin
(74) *Attorney, Agent, or Firm* — Woodcock Washburn

(57) ABSTRACT

Compounds, compositions and methods are provided for modulating the expression of exportin 5. The compositions comprise oligonucleotides, targeted to nucleic acid encoding exportin 5. Methods of using these compounds for modulation of exportin 5 expression and for diagnosis and treatment of diseases and conditions associated with expression of exportin 5 are provided.

6 Claims, No Drawings

OTHER PUBLICATIONS

Johnson, A. W. et al., "Nuclear export of ribosomal subunits," *Trends in Biochem. Sci.* (2002) 27(11):580-585.

Lund, E. et al., "Nuclear Export of MicroRNA Precursors," *Science* (2004) 303:95-98.

Montgomery, M. K. et al., "RNA as a target of double-stranded RNA-mediated genetic interference in *Caenorhabditis elegans*," *Proc. Natl. Acad. Sci. USA* (1998) 95:15502-15507.

Screaton, R. A. et al., "Fas-associated death domain protein interacts with methyl-CpG binding domain protein 4: A potential link between genome surveillance and apoptosis," *PNAS* (2003) 100(9):5211-5216.

Shi, Y., "Mammalian RNAi for the masses," *Trends in Genetics* (2003) 19(1):9-12.

Tijsterman, M. et al., "RNA Helicase MUT-14-Dependent Gene Silencing Triggered in *C. elegans* by Short Antisense RNAs," *Science* (2002) 295:694-697.

Yi, R. et al., "Exportin-5 mediates the nuclear export of pre-microRNAs and short hairpin RNAs," *Genes Dev.* (2003) 17:3011-3016.

* cited by examiner

MODULATION OF EXPORTIN 5 EXPRESSION

CROSS-REFERENCE TO RELATED APPLICATIONS

This application claims priority to U.S. provisional application Ser. No. 60/574,118 filed May 24, 2004, which is incorporated herein by reference in its entirety.

FIELD OF THE INVENTION

The present invention provides compositions and methods for modulating the expression of exportin 5. In particular, this invention relates to oligomeric compounds, particularly antisense compound and oligonucleotide compounds, which, in some embodiments, hybridize with nucleic acid molecules encoding exportin 5. Such compounds are shown herein to modulate the expression of exportin 5.

BACKGROUND OF THE INVENTION

Nuclear envelopes of eukaryotic cells provide a means of spatially separating transcription and translation and allow for extensive processing of RNAs before their use in the cytoplasm. Selective and regulated transport of macromolecules through nuclear pore complexes enables cells to control the delivery of molecules to the cytoplasm and to monitor the maturation and functionality of these cargos (Johnson et al., Trends Biochem. Sci., 2002, 27, 580-585).

Exportin 5, also known as XPO5, belongs to a large family of karyopherins, which are proteins that mediate the transport of cargo between the nuclear and cytoplasmic compartments in a RanGTP-dependent manner. First cloned in 1999 from an adult brain cDNA library, exportin 5 shares significant homology with the general nucleoporin export receptor CRM1 (Brownawell et al., J. Cell. Biol., 2002, 156, 53-64).

RT-PCR studies have detected low to moderate expression in heart, brain, lung, liver, skeletal muscle, kidney, pancreas, spleen, testis, and ovary. The deduced 1,205-amino acid protein has a calculated molecular mass of about 136 kD and exportin 5 homologues have been cloned in Xenopus and Arabidopsi (Bohnsack et al., Rna, 2004, 10, 185-191; Bollman et al., Development, 2003, 130, 1493-1504).

To date, a number of different cargo have been identified for exportin 5, including interleukin enhancer binding protein and the Fas-associated death domain protein (Brownawell et al., J. Cell. Biol., 2002, 156, 53-64; Screaton et al., Proc Natl Acad Sci USA, 2003, 100, 5211-5216). Export of interleukin enhancer binding factor 3 (ILF3) was demonstrated by Bromawell et al. (Brownawell et al., J. Cell. Biol., 2002, 156, 53-64). Exportin 5 was shown to bind ILF3 at its doublestranded RNA-binding domain (dsRBD), and this binding is disrupted in the presence of dsRNA (Brownawell and Macara, J. Cell. Biol., 2002, 156, 53-64). Exportin 5 also binds the dsRBD of the spermatid perinuclear binding protein, staufen, and protein kinase R. It is thought that exportin 5 regulates the translocation of these dsRBD proteins to the cytoplasm, where they interact with target mRNAs.

Bohnsack (Bohnsack et al., Embo. J., 2002, 21, 6205-6215) and Calado (Calado et al., Embo. J., 2002, 21, 6216-6224) report that exportin 5 transports the translation elongation factor 1A (eEF1A), and that this transport depends on interaction via aminoacylated tRNAs, thereby ensuring the confinement of translation to the cytoplasm.

By microinjection in Xenopus oocyte, Gwizdek et al. (Gwizdek et al., J. Biol. Chem., 2003, 278, 5505-5508) found that exportin 5 mediated the nuclear export of adenovirus VA1 RNA. The authors demonstrated that exportin 5 preferentially recognizes and transports RNAs containing a minihelix motif, which is a double-stranded stem structure. Gwizdek et al. (Gwizdek et al., J. Biol. Chem., 2004, 279, 884-891) further demonstrated that the formation of the exportin 5 ILF3 complex is facilitated by the simultaneous binding of exportin 5 to minihelix-containing RNAs.

Exportin 5 has also been shown to mediate the efficient nuclear export of short microRNA (miRNA) precursors (pre-miRNAs) in both Xenopus and human cell lines. (Bohnsack et al., Rna, 2004, 10, 185-191; Lund et al., Science, 2004, 303, 95-98; Yi et al., Genes Dev., 2003, 17, 3011-3016). Pre-miRNAs are endogenous, approximately 70 nucleotide-long hairpin (also known as stem-loop or foldback) precursor transcripts that can form local hairpin structures. Once in the cytoplasm, these miRNA hairpin precursors are processed such that a single-stranded mature miRNA molecule is generated from one arm of the hairpin precursor. Alternatively, a polycistronic miRNA precursor transcript may contain multiple hairpins, each processed into a different, single mature miRNA. The current model is that either the primary miRNA transcript or the hairpin precursor is transported out of the nucleus by and cleaved by Dicer to yield a double-stranded intermediate. Only one strand of this short-lived intermediate accumulates as the mature miRNA (Ambros et al., RNA, 2003, 9, 277-279; Bartel and Bartel, Plant Physiology, 2003, 132, 709-717; Shi, Trends in Genetics, 2003, 19, 9-12). Mature miRNAs are approximately 22 nucleotide-long RNAs that can play important regulatory roles by targeting mRNA for cleavage or translational repression. Lund et al. (Lund et al., Science, 2004, 303, 95-98) further demonstrated that exportin 5 binds correctly processed pre-miRNAs directly and specifically, but interacts only weakly with extended pre-miRNAs that yield incorrect miRNAs when processed. This observation suggests that exportin 5 is key to miRNA biogenesis and may help coordinate nuclear and cytoplasmic processing steps.

Antisense technology is an effective means of reducing the expression of specific gene products and therefore is uniquely useful in a number of therapeutic, diagnostic, and research applications for the modulation of exportin 5 expression. The present invention provides compositions and methods for modulating exportin 5 expression.

SUMMARY OF THE INVENTION

The present invention is directed to oligomeric compounds, such as antisense compounds and nucleic acid and nucleic acid-like oligomers, which are targeted to a nucleic acid encoding exportin 5, and which modulate the expression of exportin 5. Pharmaceutical and other compositions comprising the compounds of the invention are also provided. Further provided are methods of screening for modulators of exportin 5 and methods of modulating the expression of exportin 5 in a cell, tissue or animal comprising contacting the cell, tissue or animal with one or more of the compounds or compositions of the invention. Methods of treating an animal, particularly a human, suspected of having or being prone to a disease or condition associated with expression of exportin 5 are also set forth herein. Such methods comprise administering a therapeutically or prophylactically effective amount of one or more of the compounds or compositions of the invention to the animal.

DESCRIPTION OF EMBODIMENTS

The present invention employs oligomeric compounds, such as oligonucleotides and similar species for use in modulating the function or effect of nucleic acid molecules encoding exportin 5. This is accomplished by providing oligonucleotides which specifically hybridize with one or more nucleic acid molecules encoding exportin 5. As used herein, the terms "target nucleic acid" and "nucleic acid molecule encoding exportin 5" have been used for convenience to encompass DNA encoding exportin 5, RNA (including pre-mRNA and mRNA or portions thereof) transcribed from such DNA, and also cDNA derived from such RNA. The hybridization of a compound of this invention with its target nucleic acid is generally referred to as "antisense." Consequently, one mechanism believed to be included in the practice of some embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently suitable to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include, but are not limited to, functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One result of such interference with target nucleic acid function is modulation of the expression of exportin 5. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the desired form of modulation of expression and mRNA is often a desired target nucleic acid.

In the context of this invention, "hybridization" means the pairing of complementary strands of oligomeric compounds. In the present invention, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid to cause a loss of activity, and there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). The compounds of the present invention comprise at least about 70%, at least about 75%, at least about 80%, at least about 85%, at least about 90%, at least about 95%, at least about 99%, or 100% sequence complementarity to a target region within the target nucleic acid sequence to which they are targeted. For example, a compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, a compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of a compound with a region of a target nucleic acid can be determined routinely using BLAST programs (basic local alignment search tools) and Power-BLAST programs known in the art (Altschul et al., J. Mol. Biol., 1990, 215, 403-410; Zhang et al., Genome Res., 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some embodiments, homology, sequence identity or complementarity, between the oligomeric compound and the target is about 90%, about 92%, about 94%, about 95%, about 96%, about 97%, about 98%, about 99%, or 100%.

According to the present invention, oligomeric compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo et al., Cell, 1995, 81, 611-620). Montgomery et al. have shown that the primary interference effects of dsRNA are posttranscriptional (Montgomery et al., Proc. Natl. Acad. Sci. USA, 1998, 95, 15502-15507). The posttranscriptional antisense mechanism defined in *C. elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., Nature, 1998, 391, 806-811). Recently, it has been shown that it is, in fact, the single-stranded RNA oligomers of antisense polarity of the dsRNAs which are the potent inducers of RNAi (Tijsterman et al., Science, 2002, 295, 694-697).

The compounds of the present invention also include modified compounds in which a different base is present at one or more of the nucleotide positions in the compound. For example, if the first nucleotide is an adenosine, modified compounds may be produced which contain thymidine, guanosine or cytidine at this position. This may be done at any of the positions of the antisense compound. These compounds are then tested using the methods described herein to determine their ability to inhibit expression of exportin 5 mRNA.

In the context of this invention, the term "oligomeric compound" refers to a polymer or oligomer comprising a plurality of monomeric units. The term "oligomeric compound" includes, for example, oligonucleotides and antisense compounds. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

While oligonucleotides are one form of the compounds of this invention, the present invention comprehends other families of antisense compounds as well, including but not limited to oligonucleotide analogs and mimetics such as those described herein.

The compounds in accordance with this invention can comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length, or any range therewithin.

In one embodiment, the compounds of the invention are 12 or 13 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length, or any range therewithin.

In another embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length, or any range therewithin.

Compounds 8 to 80 nucleobases in length comprising a stretch of at least eight (8) consecutive nucleobases selected from within the illustrative compounds are considered to be suitable compounds as well.

Exemplary compounds include oligonucleotide sequences that comprise at least the 8 consecutive nucleobases from the 5'-terminus of one of the illustrative compounds (the remaining nucleobases being a consecutive stretch of the same oligonucleotide beginning immediately upstream of the 5'-terminus of the compound which is specifically hybridizable to the target nucleic acid and continuing until the oligonucleotide contains about 8 to about 80 nucleobases, or any other range set forth herein). Similarly suitable compounds are represented by oligonucleotide sequences that comprise at least the 8 consecutive nucleobases from the 3'-terminus of one of the illustrative compounds (the remaining nucleobases being a consecutive stretch of the same oligonucleotide beginning immediately downstream of the 3'-terminus of the compound which is specifically hybridizable to the target nucleic acid and continuing until the oligonucleotide contains about 8 to about 80 nucleobases, or any other range set forth herein). It is also understood that suitable compounds may be represented by oligonucleotide sequences that comprise at least 8 consecutive nucleobases from an internal portion of the sequence of an illustrative compound, and may extend in either or both directions until the oligonucleotide contains about 8 to about 80 nucleobases, or any other range set forth herein.

One having skill in the art armed with the compounds illustrated herein will be able, without undue experimentation, to identify further compounds.

"Targeting" an oligomeric compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes exportin 5.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding exportin 5, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the compounds of the present invention.

The open reading frame (ORF) or "coding region," which is known in the art to refer to the region between the translation initiation codon and the translation termination codon, is also a region which may be targeted effectively. Within the context of the present invention, a suitable region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also suitable to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also suitable target sites. mRNA transcripts produced via the process of splicing of two (or more) mRNAs from different gene sources known as "fusion transcripts" are also suitable target sites. It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants." Consequently, mRNA variants are processed pre-mRNA variants and each unique pre-mRNA variant must always produce a unique mRNA variant as a result of splicing. These mRNA variants are also known as "alternative splice variants." If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also suitable target nucleic acids.

The locations on the target nucleic acid to which the suitable oligomeric compounds hybridize are hereinbelow referred to as "suitable target segments." As used herein the term "suitable target segment" is defined as at least an 8-nucleobase portion of a target region to which an active oligomeric compound is targeted. While not wishing to be bound by theory, it is presently believed that these target segments represent portions of the target nucleic acid which are accessible for hybridization.

While the specific sequences of certain suitable target segments are set forth herein, one of skill in the art will recognize that these serve to illustrate and describe particular embodiments within the scope of the present invention. Additional target segments may be identified by one having ordinary skill.

Target segments 8-80 nucleobases in length comprising a stretch of at least eight (8) consecutive nucleobases selected from within the illustrative target segments are considered to be suitable for targeting as well.

Target segments can include DNA or RNA sequences that comprise at least the 8 consecutive nucleobases from the 5'-terminus of one of the illustrative target segments (the remaining nucleobases being a consecutive stretch of the same DNA or RNA beginning immediately upstream of the 5'-terminus of the target segment and continuing until the DNA or RNA contains about 8 to about 80 nucleobases, or any range herein). Similarly target segments are represented by DNA or RNA sequences that comprise at least the 8 consecutive nucleobases from the 3'-terminus of one of the illustrative target segments (the remaining nucleobases being a consecutive stretch of the same DNA or RNA beginning immediately downstream of the 3'-terminus of the target segment and continuing until the DNA or RNA contains about 8 to about 80 nucleobases, or any range herein). It is also understood that antisense target segments may be represented by DNA or RNA sequences that comprise at least 8 consecutive nucleobases from an internal portion of the sequence of an illustrative target segment, and may extend in either or both directions until the oligonucleotide contains about 8 to about 80 nucleobases, or any range herein. One having skill in the art armed with the suitable target segments illustrated herein will be able, without undue experimentation, to identify further suitable target segments.

Once one or more target regions, segments or sites have been identified, antisense compounds are chosen which are sufficiently complementary to the target, i.e., hybridize sufficiently well and with sufficient specificity, to give the desired effect.

The oligomeric compounds can also be targeted to regions of a target nucleobase sequence, such as those disclosed herein (e.g. in Example 13). All regions of a nucleobase sequence to which an oligomeric compound can be targeted, wherein the regions are greater than or equal to 8 and less than or equal to 80 nucleobases, are described as follows:

Let $R(n, n+m-1)$ be a region from a target nucleobase sequence, where "n" is the 5'-most nucleobase position of the region, where "n+m-1" is the 3'-most nucleobase position of the region and where "m" is the length of the region. A set "$S(m)$", of regions of length "m" is defined as the regions where n ranges from 1 to L−m+1, where L is the length of the target nucleobase sequence and L>m. A set, "A", of all regions can be constructed as a union of the sets of regions for each length from where m is greater than or equal to 8 and is less than or equal to 80, or any other range described herein.

This set of regions can be represented using the following mathematical notation:

$$A = \bigcup_m S(m) \text{ where } m \in N \mid 8 \leq m \leq 80$$

and $$S(m) = \{R_{n,n+m-1} \mid n \in \{1, 2, 3, \ldots, L-m+1\}\}$$

where the mathematical operator | indicates "such that", where the mathematical operator $\epsilon$ indicates "a member of a set" (e.g. y∈Z indicates that element y is a member of set Z), where x is a variable, where N indicates all natural numbers, defined as positive integers, and where the mathematical operator ∪ indicates "the union of sets".

For example, the set of regions for m equal to 8, 9 and 80 can be constructed in the following manner. The set of regions, each 8 nucleobases in length, $S(m=8)$, in a target nucleobase sequence 100 nucleobases in length (L=100), beginning at position 1 (n=1) of the target nucleobase sequence, can be created using the following expression:

$$S(8) = \{R_{1,8} \mid n \in \{1, 2, 3, \ldots, 93\}\}$$

and describes the set of regions comprising nucleobases 1-8, 2-9, 3-10, 4-11, 5-12, 6-13, 7-14, 8-15, 9-16, 10-17, 11-18, 12-19, 13-20, 14-21, 15-22, 16-23, 17-24, 18-25, 19-26, 20-27, 21-28, 22-29, 23-30, 24-31, 25-32, 26-33, 27-34, 28-35, 29-36, 30-37, 31-38, 32-39, 33-40, 34-41, 35-42, 36-43, 37-44, 38-45, 39-46, 40-47, 41-48, 42-49, 43-50, 44-51, 45-52, 46-53, 47-54, 48-55, 49-56, 50-57, 51-58, 52-59, 53-60, 54-61, 55-62, 56-63, 57-64, 58-65, 59-66, 60-67, 61-68, 62-69, 63-70, 64-71, 65-72, 66-73, 67-74, 68-75, 69-76, 70-77, 71-78, 72-79, 73-80, 74-81, 75-82, 76-83, 77-84, 78-85, 79-86, 80-87, 81-88, 82-89, 83-90, 84-91, 85-92, 86-93, 87-94, 88-95, 89-96, 90-97, 91-98, 92-99, 93-100.

An additional set for regions 20 nucleobases in length, in a target sequence 100 nucleobases in length, beginning at position 1 of the target nucleobase sequence, can be described using the following expression:

$$S(20) = \{R_{1,20} \mid n \in \{1, 2, 3, \ldots, 81\}\}$$

and describes the set of regions comprising nucleobases 1-20, 2-21, 3-22, 4-23, 5-24, 6-25, 7-26, 8-27, 9-28, 10-29, 11-30, 12-31, 13-32, 14-33, 15-34, 16-35, 17-36, 18-37, 19-38, 20-39, 21-40, 22-41, 23-42, 24-43, 25-44, 26-45, 27-46, 28-47, 29-48, 30-49, 31-50, 32-51, 33-52, 34-53, 35-54, 36-55, 37-56, 38-57, 39-58, 40-59, 41-60, 42-61, 43-62, 44-63, 45-64, 46-65, 47-66, 48-67, 49-68, 50-69, 51-70, 52-71, 53-72, 54-73, 55-74, 56-75, 57-76, 58-77, 59-78, 60-79, 61-80, 62-81, 63-82, 64-83, 65-84, 66-85, 67-86, 68-87, 69-88, 70-89, 71-90, 72-91, 73-92, 74-93, 75-94, 76-95, 77-96, 78-97, 79-98, 80-99, 81-100.

An additional set for regions 80 nucleobases in length, in a target sequence 100 nucleobases in length, beginning at position 1 of the target nucleobase sequence, can be described using the following expression:

$$S(80) = \{R_{1,80} \mid n \in \{1, 2, 3, \ldots, 21\}\}$$

and describes the set of regions comprising nucleobases 1-80, 2-81, 3-82, 4-83, 5-84, 6-85, 7-86, 8-87, 9-88, 10-89, 11-90, 12-91, 13-92, 14-93, 15-94, 16-95, 17-96, 18-97, 19-98, 20-99, 21-100.

Thus, in this example, A would include regions 1-8, 2-9, 3-10 . . . 93-100, 1-20, 2-21, 3-22 . . . 81-100, 1-80, 2-81, 3-82 . . . 21-100.

The union of these aforementioned example sets and other sets for lengths from 10 to 19 and 21 to 79 can be described using the mathematical expression $$A = \bigcup_m S(m)$$

where ∪ represents the union of the sets obtained by combining all members of all sets.

The mathematical expressions described herein defines all possible target regions in a target nucleobase sequence of any length L, where the region is of length m, and where m is greater than or equal to 8 and less than or equal to 80 nucleobases and, and where m is less than L, and where n is less than L−m+1.

In a further embodiment, the "suitable target segments" identified herein may be employed in a screen for additional compounds that modulate the expression of exportin 5. "Modulators" are those compounds that decrease or increase the expression of a nucleic acid molecule encoding exportin 5 and which comprise at least an 8-nucleobase portion which is complementary to a suitable target segment. The screening method comprises the steps of contacting a suitable target segment of a nucleic acid molecule encoding exportin 5 with one or more candidate modulators, and selecting for one or more candidate modulators which decrease or increase the expression of a nucleic acid molecule encoding exportin 5. Once it is shown that the candidate modulator or modulators are capable of modulating (e.g. either decreasing or increasing) the expression of a nucleic acid molecule encoding exportin 5, the modulator may then be employed in further investigative studies of the function of exportin 5, or for use as a research, diagnostic, or therapeutic agent in accordance with the present invention.

In some embodiments of the invention, the oligomeric compound is 13 to 50 nucleobases in length and is hybridizable under physiological conditions to a region within nucleotides 44000 to 44500 of SEQ ID NO:11 or to a region within nucleotides 1956 to 4527 of SEQ ID NO:4. As used herein, the term "within" is inclusive of the two terminal nucleotides of the range, and also includes those oligomeric compounds that overlap with any of the nucleobases within the indicated nucleotides. The compound may comprise at least one modified nucleobase, sugar, or internucleoside linkage. In some embodiments, the compound is hybridizable under physiological conditions to a region within nucleotides 44379 to 44398 of SEQ ID NO:11. In some embodiments, the compound is hybridizable under physiological conditions to a region within nucleotides 1956 to 2642 of SEQ ID NO:4. In other embodiments, the compound is hybridizable under physiological conditions to a region within nucleotides 3532 to 3829 of SEQ ID NO:4. In some embodiments, the compound is hybridizable under physiological conditions to a region within nucleotides 4006 to 4527 of SEQ ID NO:4. In some embodiments, the compound is hybridizable under physiological conditions to a region within nucleotides 4006 to 4025 of SEQ ID NO:4. In some embodiments, the compound is hybridizable under physiological conditions to a region within nucleotides 4294 to 4313 of SEQ ID NO:4. In some embodiments, the compound is hybridizable under physiological conditions to a region within nucleotides 4304 to 4323 of SEQ ID NO:4.

The suitable target segments of the present invention may be also be combined with their respective complementary oligomeric compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons et al., Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The compounds of the present invention can also be applied in the areas of drug discovery and target validation. The present invention comprehends the use of the compounds and suitable target segments identified herein in drug discovery efforts to elucidate relationships that exist between exportin 5 and a disease state, phenotype, or condition. These methods include detecting or modulating exportin 5 comprising contacting a sample, tissue, cell, or organism with the compounds of the present invention, measuring the nucleic acid or protein level of exportin 5 and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

The compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on a stimulated or unstimulated cell and in the presence or absence of other compounds which affect expression patterns.

Examples of methods of gene expression analysis known in the art include DNA arrays or microarrays (Brazma et al., FEBS Lett., 2000, 480, 17-24; Celis et al., FEBS Lett., 2000, 480, 2-16), SAGE (serial analysis of gene expression) (Madden et al., Drug Discov. Today, 2000, 5, 415-425), READS (restriction enzyme amplification of digested cDNAs) (Prashar et al., Methods Enzymol., 1999, 303, 258-72), TOGA (total gene expression analysis) (Sutcliffe et al., Proc. Natl. Acad. Sci. U.S.A., 2000, 97, 1976-81), protein arrays and proteomics (Celis et al., FEBS Lett., 2000, 480, 2-16; Jungblut et al., Electrophoresis, 1999, 20, 2100-10), expressed sequence tag (EST) sequencing (Celis et al., FEBS Lett., 2000, 480, 2-16; Larsson et al., J. Biotechnol., 2000, 80, 143-57), subtractive RNA fingerprinting (SuRF) (Fuchs et al., Anal. Biochem., 2000, 286, 91-98; Larson et al., Cytometry, 2000, 41, 203-208), subtractive cloning, differential display (DD) (Jurecic et al., Curr. Opin. Microbiol., 2000, 3, 316-21), comparative genomic hybridization (Carulli et al., J. Cell Biochem. Suppl., 1998, 31, 286-96), FISH (fluorescent in situ hybridization) techniques (Going et al., Eur. J. Cancer, 1999, 35, 1895-904) and mass spectrometry methods (To, Comb. Chem. High Throughput Screen, 2000, 3, 235-41).

The compounds of the invention are useful for, for example, research and diagnostics, because these compounds hybridize to nucleic acids encoding exportin 5. For example, the primers and probes disclosed herein are useful in methods requiring the specific detection of nucleic acid molecules encoding exportin 5 and in the amplification of said nucleic acid molecules for detection or for use in further studies of exportin 5. Hybridization of the primers and probes with a nucleic acid encoding exportin 5 can be detected by means known in the art. Such means may include conjugation of an enzyme to the primer or probe, radiolabelling of the primer or probe or any other suitable detection means. Kits using such detection means for detecting the level of exportin 5 in a sample may also be prepared.

The specificity and sensitivity of antisense is also harnessed by those of skill in the art for therapeutic uses. Oligomeric compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of a cell, tissue and animal, especially a human.

For therapeutics, an animal, such as a human, suspected of having a disease or disorder which can be treated by modulating the expression of exportin 5 is treated by administering a compound in accordance with this invention. For example, in one non-limiting embodiment, the methods comprise administering to the animal a therapeutically effective amount of a exportin 5 inhibitor. In some embodiments, the animal is identified as being in need of treatment. The exportin 5 inhibitors of the present invention effectively inhibit the activity of the exportin 5 protein or inhibit the expression of the exportin 5 protein. In one embodiment, the activity or expression of exportin 5 in an animal is inhibited by at least about 10%, by at least about 20%, by at least about 30%, by at least about 40%, by at least about 50%, by at least about 60%, by at least about 70%, by at least about 80%, by at least about 90%, by at least about 92%, by at least about 94%, by at least about 95%, by at least about 96%, by at least about 98%, or by 100%. In some embodiments, phenotypic change(s) are determined or measured after administering a compound of the invention.

For example, the reduction of the expression of exportin 5 may be measured in serum, adipose tissue, liver or any other body fluid, tissue or organ of the animal. The cells contained within said fluids, tissues or organs being analyzed can contain a nucleic acid molecule encoding exportin 5 protein and/or the exportin 5 protein itself.

The compounds of the invention can be utilized in compositions, such as pharmaceutical compositions, by adding an effective amount of a compound to a suitable pharmaceutically acceptable diluent or carrier. Use of the compounds and methods of the invention may also be useful prophylactically.

As is known in the art, a nucleoside is a base-sugar combination. The base portion of the nucleoside is normally a heterocyclic base sometimes referred to as a "nucleobase" or simply a "base." The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally desired. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Suitable modified oligonucleotide backbones containing a phosphorus atom therein include, for example, phosphorothioates, chiral phosphorothioates, phosphorodithioates, phosphotriesters, aminoalkylphosphotriaminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. Patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

Suitable modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones;

sulfamate backbones; methyleneimino and methylenehydrazino backbones; sulfonate and sulfonamide backbones; amide backbones; and others having mixed N, O, S and $CH_2$ component parts.

Representative U.S. Patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Modified Sugar and Internucleoside Linkages-Mimetics

In other compounds, e.g., oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative U.S. Patents that teach the preparation of PNA compounds include, but are not limited to, U.S. Pat. Nos. 5,539,082; 5,714,331; and 5,719,262. Further teaching of PNA compounds can be found in Nielsen et al., Science, 1991, 254, 1497-1500.

Further embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester backbone is represented as —O—P—O—$CH_2$—) of the above referenced U.S. Pat. No. 5,489,677, and the amide backbones of the above referenced U.S. Pat. No. 5,602,240. Also suitable are oligonucleotides having morpholino backbone structures of the above-referenced U.S. Pat. No. 5,034,506.

Modified Sugars

Modified compounds may also contain one or more substituted sugar moieties. The compounds of the invention can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Also suitable are O(($CH_2$)$_n$O)$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON(($CH_2$)$_n$$CH_3$)$_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, S$CH_3$, OCN, Cl, Br, CN, $CF_3$, O$CF_3$, SO$CH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Another modification includes 2'-O-methoxyethyl (2'-O—$CH_2CH_2OCH_3$, also known as 2'-O-(2-methoxyethyl) or 2'-methoxyethoxy or 2'-MOE) (Martin et al., Helv. Chim. Acta, 1995, 78, 486-504) i.e., an alkoxyalkoxy group. Another modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylamino-ethoxy-ethyl or 2'-DMAEOE), i.e., 2'-O—$CH_2$—O—$CH_2$—N($CH_3$)$_2$, also described in examples hereinbelow.

Other modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A suitable 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligomeric compounds may also have sugar mimetics such as cyclobutyl moieties in place of the pentofuranosyl sugar. Representative U.S. Patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920.

A further modification of the sugar includes Locked Nucleic Acids (LNAs) in which the 2'-hydroxyl group is linked to the 3' or 4' carbon atom of the sugar ring, thereby forming a bicyclic sugar moiety. The linkage can be a methylene (—$CH_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

The compounds may also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-b)(1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687, 808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Some of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently suitable base substitutions, even more particularly when combined with 2'-O-methoxyethyl sugar modifications.

Representative U.S. Patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941; and 5,750,692.

Conjugates

Another modification of the compounds of the invention involves chemically linking to the compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmaco-dynamic properties, in the context of this invention, include, but are not limited to, groups that improve uptake, enhance resistance to degradation, and/or strengthen sequence-specific hybridization with the target nucleic acid. Groups that enhance the pharmacokinetic properties, in the context of this invention, include, but are not limited to, groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

The compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999).

Representative U.S. Patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270).

Suitable 3'-cap structures of the present invention include, for example, 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925).

Additional 3' and 5'-stabilizing groups that can be used to cap one or both ends of an oligomeric compound to impart nuclease stability include those disclosed in WO 03/004602 published on Jan. 16, 2003.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are oligomeric compounds, particularly oligonucleotides, which contain two or more chemically distinct regions, each made up of at least one monomer unit, i.e., a nucleotide in the case of an oligonucleotide compound. Chimeric antisense oligonucleotides are thus a form of antisense compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric compounds of the invention may be formed as composite structures of two or more oligonucleotides, modified oligonucleotides, oligonucleosides and/or oligonucleotide mimetics as described above. Chimeric antisense compounds can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers."

Such compounds have also been referred to in the art as hybrids. In a gapmer that is 20 nucleotides in length, a gap or wing can be 1, 2, 3, 4, 5, 6, 7, 8, 9, 10, 11, 12, 13, 14, 15, 16, 17 or 18 nucleotides in length. In one embodiment, a 20-nucleotide gapmer is comprised of a gap 8 nucleotides in length, flanked on both the 5' and 3' sides by wings 6 nucleotides in length. In another embodiment, a 20-nucleotide gapmer is comprised of a gap 10 nucleotides in length, flanked on both the 5' and 3' sides by wings 5 nucleotides in length. In another embodiment, a 20-nucleotide gapmer is comprised of a gap 12 nucleotides in length flanked on both the 5' and 3' sides by wings 4 nucleotides in length. In a further embodiment, a 20-nucleotide gapmer is comprised of a gap 14 nucleotides in length flanked on both the 5' and 3' sides by wings 3 nucleotides in length. In another embodiment, a 20-nucleotide gapmer is comprised of a gap 16 nucleotides in length flanked on both the 5' and 3' sides by wings 2 nucleotides in length. In a further embodiment, a 20-nucleotide gapmer is comprised of a gap 18 nucleotides in length flanked on both the 5' and 3' ends by wings 1 nucleotide in length. Alternatively, the wings are of different lengths, for example, a 20-nucleotide gapmer may be comprised of a gap 10 nucleotides in length, flanked by a 6-nucleotide wing on one side (5' or 3') and a 4-nucleotide wing on the other side (5' or 3').

In a hemimer, an "open end" chimeric antisense compound, 20 nucleotides in length, a gap segment, located at either the 5' or 3' terminus of the oligomeric compound, can be 1, 2, 3, 4, 5, 6, 7, 8, 9, 10, 11, 12, 13, 14, 15, 16, 17, 18 or 19 nucleotides in length. For example, a 20-nucleotide hemimer can have a gap segment of 10 nucleotides at the 5' end and a second segment of 10 nucleotides at the 3' end. Alternatively, a 20-nucleotide hemimer can have a gap segment of 10 nucleotides at the 3' end and a second segment of 10 nucleotides at the 5' end.

Representative U.S. Patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative U.S. patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The oligomeric compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, suitable examples of pharmaceutically acceptable salts and their uses are further described in U.S. Pat. No. 6,287,860. Sodium and potassium salts are suitable.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860.

One of skill in the art will recognize that formulations are routinely designed according to their intended use, i.e. route of administration.

Suitable formulations for topical administration include those in which the oligonucleotides of the invention are in admixture with a topical delivery agent such as lipids, liposomes, fatty acids, fatty acid esters, steroids, chelating agents and surfactants. Suitable lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Suitable fatty acids and esters, pharmaceutically acceptable salts thereof, and their uses are further described in U.S. Pat. No. 6,287,860. Topical formulations are described in detail in U.S. patent application Ser. No. 09/315,298 filed on May 20, 1999.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Suitable oral formulations are those in which oligonucleotides of the invention are administered in conjunction with one or more penetration enhancers surfactants and chelators. Suitable surfactants include fatty acids and/or esters or salts thereof, bile acids and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. A particularly suitable combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860. Oral formulations for oligonucleotides and their preparation are described in detail in U.S. application Ser. Nos. 09/108,673 (filed Jul. 1, 1998), 09/315,298 (filed May 20, 1999) and 10/071,822, filed Feb. 8, 2002.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Oligonucleotides may be formulated for delivery in vivo in an acceptable dosage form, e.g. as parenteral or non-parenteral formulations. Parenteral formulations include intravenous (IV), subcutaneous (SC), intraperitoneal (IP), intravitreal and intramuscular (IM) formulations, as well as formulations for delivery via pulmonary inhalation, intranasal administration, topical administration, etc. Non-parenteral formulations include formulations for delivery via the alimentary canal, e.g. oral administration, rectal administration, intrajejunal instillation, etc. Rectal administration includes administration as an enema or a suppository. Oral administration includes administration as a capsule, a gel capsule, a pill, an elixir, etc.

In some embodiments, an oligonucleotide may be administered to a subject via an oral route of administration. The subject may be an animal or a human (man). An animal subject may be a mammal, such as a mouse, a rat, a dog, a guinea pig, a monkey, a non-human primate, a cat or a pig. Non-human primates include monkeys and chimpanzees. A suitable animal subject may be an experimental animal, such as a mouse, rat, mouse, a rat, a dog, a monkey, a non-human primate, a cat or a pig.

In some embodiments, the subject may be a human. In certain embodiments, the subject may be a human patient in need of therapeutic treatment as discussed in more detail herein. In certain embodiments, the subject may be in need of modulation of expression of one or more genes as discussed in more detail herein. In some particular embodiments, the subject may be in need of inhibition of expression of one or more genes as discussed in more detail herein. In particular embodiments, the subject may be in need of modulation, i.e. inhibition or enhancement, of Tudor-SN in order to obtain therapeutic indications discussed in more detail herein.

In some embodiments, non-parenteral (e.g. oral) oligonucleotide formulations according to the present invention result in enhanced bioavailability of the oligonucleotide. In this context, the term "bioavailability" refers to a measurement of that portion of an administered drug which reaches the circulatory system (e.g. blood, especially blood plasma) when a particular mode of administration is used to deliver the drug. Enhanced bioavailability refers to a particular mode of administration's ability to deliver oligonucleotide to the peripheral blood plasma of a subject relative to another mode of administration. For example, when a non-parenteral mode of administration (e.g. an oral mode) is used to introduce the drug into a subject, the bioavailability for that mode of administration may be compared to a different mode of administration, e.g. an IV mode of administration. In some embodiments, the area under a compound's blood plasma concentration curve ($AUC_0$) after non-parenteral (e.g. oral, rectal, intrajejunal) administration may be divided by the area under the drug's plasma concentration curve after intravenous (i.v.) administration ($AUC_{iv}$) to provide a dimensionless quotient (relative bioavailability, RB) that represents fraction of compound absorbed via the non-parenteral route as compared to the IV route. A composition's bioavailability is said to be enhanced in comparison to another composition's bioavailability when the first composition's relative bioavailability ($RB_1$) is greater than the second composition's relative bioavailability ($RB_2$).

In general, bioavailability correlates with therapeutic efficacy when a compound's therapeutic efficacy is related to the blood concentration achieved, even if the drug's ultimate site of action is intracellular (van Berge-Henegouwen et al., Gastroenterol., 1977, 73, 300). Bioavailability studies have been used to determine the degree of intestinal absorption of a drug by measuring the change in peripheral blood levels of the drug after an oral dose (DiSanto, Chapter 76 In: Remington's Pharmaceutical Sciences, 18th Ed., Gennaro, ed., Mack Publishing Co., Easton, Pa., 1990, pages 1451-1458).

In general, an oral composition's bioavailability is said to be "enhanced" when its relative bioavailability is greater than the bioavailability of a composition substantially consisting of pure oligonucleotide, i.e. oligonucleotide in the absence of a penetration enhancer.

Organ bioavailability refers to the concentration of compound in an organ. Organ bioavailability may be measured in test subjects by a number of means, such as by whole-body radiography. Organ bioavailability may be modified, e.g. enhanced, by one or more modifications to the oligonucleotide, by use of one or more carrier compounds or excipients, etc. as discussed in more detail herein. In general, an increase in bioavailability will result in an increase in organ bioavailability.

Oral oligonucleotide compositions according to the present invention may comprise one or more "mucosal penetration enhancers," also known as "absorption enhancers" or simply as "penetration enhancers." Accordingly, some embodiments of the invention comprise at least one oligonucleotide in combination with at least one penetration enhancer. In general, a penetration enhancer is a substance that facilitates the transport of a drug across mucous membrane(s) associated with the desired mode of administration, e.g. intestinal epithelial membranes. Accordingly it is desirable to select one or more penetration enhancers that facilitate the uptake of an oligonucleotide, without interfering with the activity of the oligonucleotide, and in a such a manner the oligonucleotide can be introduced into the body of an animal without unacceptable side-effects such as toxicity, irritation or allergic response.

Embodiments of the present invention provide compositions comprising one or more pharmaceutically acceptable penetration enhancers, and methods of using such compositions, which result in the improved bioavailability of oligonucleotides administered via non-parenteral modes of administration. Heretofore, certain penetration enhancers have been used to improve the bioavailability of certain drugs. See Muranishi, Crit. Rev. Ther. Drug Carrier Systems, 1990, 7, 1 and Lee et al., Crit. Rev. Ther. Drug Carrier Systems, 1991, 8, 91. It has been found that the uptake and delivery of oligonucleotides, relatively complex molecules which are known to be difficult to administer to animals and man, can be greatly improved even when administered by non-parenteral means through the use of a number of different classes of penetration enhancers.

In some embodiments, compositions for non-parenteral administration include one or more modifications from naturally-occurring oligonucleotides (i.e. full-phosphodiester deoxyribosyl or full-phosphodiester ribosyl oligonucleotides). Such modifications may increase binding affinity, nuclease stability, cell or tissue permeability, tissue distribution, or other biological or pharmacokinetic property. Modifications may be made to the base, the linker, or the sugar, in general, as discussed in more detail herein with regards to oligonucleotide chemistry. In some embodiments of the invention, compositions for administration to a subject, and in particular oral compositions for administration to an animal or human subject, will comprise modified oligonucleotides having one or more modifications for enhancing affinity, stability, tissue distribution, or other biological property.

Suitable modified linkers include phosphorothioate linkers. In some embodiments according to the invention, the oligonucleotide has at least one phosphorothioate linker. Phosphorothioate linkers provide nuclease stability as well as plasma protein binding characteristics to the oligonucleotide. Nuclease stability is useful for increasing the in vivo lifetime of oligonucleotides, while plasma protein binding decreases the rate of first pass clearance of oligonucleotide via renal excretion. In some embodiments, the oligonucleotide has at least two phosphorothioate linkers. In some embodiments, wherein the oligonucleotide has exactly n nucleosides, the oligonucleotide has from one to n−1 phosphorothioate linkages. In some embodiments, wherein the oligonucleotide has exactly n nucleosides, the oligonucleotide has n−1 phosphorothioate linkages. In other embodiments wherein the oligonucleotide has exactly n nucleoside, and n is even, the oligonucleotide has from 1 to n/2 phosphorothioate linkages, or, when n is odd, from 1 to (n−1)/2 phosphorothioate linkages. In some embodiments, the oligonucleotide has alternating phosphodiester (PO) and phosphorothioate (PS) linkages. In other embodiments, the oligonucleotide has at least one stretch of two or more consecutive PO linkages and at least one stretch of two or more PS linkages. In other embodiments, the oligonucleotide has at least two stretches of PO linkages interrupted by at least on PS linkage.

In some embodiments, at least one of the nucleosides is modified on the ribosyl sugar unit by a modification that imparts nuclease stability, binding affinity or some other beneficial biological property to the sugar. In some cases, the sugar modification includes a 2'-modification, e.g. the 2'-OH of the ribosyl sugar is replaced or substituted. Suitable replacements for 2'-OH include 2'-F and 2'-arabino-F. Suitable substitutions for OH include 2'-O-alkyl, e.g. 2'-O-methyl, and 2'-O-substituted alkyl, e.g. 2'-O-methoxyethyl, 2'-O-aminopropyl, etc. In some embodiments, the oligonucleotide contains at least one 2'-modification. In some embodiments, the oligonucleotide contains at least 2 2'-modifications. In some embodiments, the oligonucleotide has at least one 2'-modification at each of the termini (i.e. the 3'- and 5'-terminal nucleosides each have the same or different 2'-modifications). In some embodiments, the oligonucleotide has at least two sequential 2'-modifications at each end of the oligonucleotide. In some embodiments, oligonucleotides further comprise at least one deoxynucleoside. In particular embodiments, oligonucleotides comprise a stretch of deoxynucleosides such that the stretch is capable of activating RNase (e.g. RNase H) cleavage of an RNA to which the oligonucleotide is capable of hybridizing. In some embodiments, a stretch of deoxynucleosides capable of activating RNase-mediated cleavage of RNA comprises about 6 to about 16, e.g. about 8 to about 16 consecutive deoxynucleosides. In further embodiments, oligonucleotides are capable of eliciting cleavage by dsRNAse enzymes.

Oral compositions for administration of non-parenteral oligonucleotide compositions of the present invention may be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. A common requirement for these modes of administration is absorption over some portion or all of the alimentary tract and a need for efficient mucosal penetration of the nucleic acid(s) so administered.

Delivery of a drug via the oral mucosa, as in the case of buccal and sublingual administration, has several desirable features, including, in many instances, a more rapid rise in plasma concentration of the drug than via oral delivery (Harvey, Chapter 35 In: Remington's Pharmaceutical Sciences, 18th Ed., Gennaro, ed., Mack Publishing Co., Easton, Pa., 1990, page 711).

Endoscopy may be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., Gan To Kagaku Ryoho, 1992, 19 (10 Suppl.), 1591). Pharmaceutical compositions, including liposomal formulations, can be delivered directly into portions of the alimentary canal, such as, e.g., the duodenum (Somogyi et al., Pharm. Res., 1995, 12, 149) or the gastric submucosa (Akamo et al., Japanese J. Cancer Res., 1994, 85, 652) via endoscopic means. Gastric lavage devices (Inoue et al., Artif. Organs, 1997, 21, 28) and percutaneous endoscopic feeding devices (Pennington et al., Ailment Pharmacol. Ther., 1995, 9, 471) can also be used for direct alimentary delivery of pharmaceutical compositions.

In some embodiments, oligonucleotide formulations may be administered through the anus into the rectum or lower intestine. Rectal suppositories, retention enemas or rectal catheters can be used for this purpose and may be desired when patient compliance might otherwise be difficult to achieve (e.g., in pediatric and geriatric applications, or when the patient is vomiting or unconscious). Rectal administration can result in more prompt and higher blood levels than the oral route. (Harvey, Chapter 35 In: Remington's Pharmaceutical Sciences, 18th Ed., Gennaro, ed., Mack Publishing Co., Easton, Pa., 1990, page 711). Because about 50% of the drug that is absorbed from the rectum will bypass the liver, administration by this route significantly reduces the potential for first-pass metabolism (Benet et al., Chapter 1 In: Goodman & Gilman's The Pharmacological Basis of Therapeutics, 9th Ed., Hardman et al., eds., McGraw-Hill, New York, N.Y., 1996).

One advantageous method of non-parenteral administration oligonucleotide compositions is oral delivery. Some embodiments employ various penetration enhancers in order to effect transport of oligonucleotides and other nucleic acids across mucosal and epithelial membranes. Penetration enhancers may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Accordingly, some embodiments comprise oral oligonucleotide compositions comprising at least one member of the group consisting of surfactants, fatty acids, bile salts, chelating agents, and non-chelating surfactants. Further embodiments comprise oral oligonucleotide comprising at least one fatty acid, e.g. capric or lauric acid, or combinations or salts thereof. Other embodiments comprise methods of enhancing the oral bioavailability of an oligonucleotide, the method comprising co-administering the oligonucleotide and at least one penetration enhancer.

Other excipients that may be added to oral oligonucleotide compositions include surfactants (or "surface-active agents"), which are chemical entities which, when dissolved in an aqueous solution, reduce the surface tension of the solution or the interfacial tension between the aqueous solution and another liquid, with the result that absorption of oligonucleotides through the alimentary mucosa and other epithelial membranes is enhanced. In addition to bile salts and fatty acids, surfactants include, for example, sodium lauryl sulfate, polyoxyethylene-9-lauryl ether and polyoxyethylene-20-cetyl ether (Lee et al., Critical Reviews in Therapeutic Drug Carrier Systems, 1991, page 92); and perfluorohemical emulsions, such as FC-43 (Takahashi et al., J. Pharm. Phamacol., 1988, 40, 252).

Fatty acids and their derivatives which act as penetration enhancers and may be used in compositions of the present invention include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glyceryl 1-monocaprate, 1-dodecylazacycloheptan-2-one, acylcarnitines, acylcholines and mono- and di-glycerides thereof and/or physiologically acceptable salts thereof (i.e., oleate, laurate, caprate, myristate, palmitate, stearate, linoleate, etc.) (Lee et al., Critical Reviews in Therapeutic Drug Carrier Systems, 1991, page 92; Muranishi, Critical Reviews in Therapeutic Drug Carrier Systems, 1990, 7, 1; El-Hariri et al., J. Pharm. Pharmacol., 1992, 44, 651).

In some embodiments, oligonucleotide compositions for oral delivery comprise at least two discrete phases, which phases may comprise particles, capsules, gel-capsules, microspheres, etc. Each phase may contain one or more oligonucleotides, penetration enhancers, surfactants, bioadhesives, effervescent agents, or other adjuvant, excipient or diluent. In some embodiments, one phase comprises at least one oligonucleotide and at lease one penetration enhancer. In some embodiments, a first phase comprises at least one oligonucleotide and at least one penetration enhancer, while a second phase comprises at least one penetration enhancer. In some embodiments, a first phase comprises at least one oligonucleotide and at least one penetration enhancer, while a second phase comprises at least one penetration enhancer and substantially no oligonucleotide. In some embodiments, at least one phase is compounded with at least one degradation retardant, such as a coating or a matrix, which delays release of the contents of that phase. In some embodiments, a first phase comprises at least one oligonucleotide, at least one penetration enhancer, while a second phase comprises at least one penetration enhancer and a release-retardant. In particular embodiments, an oral oligonucleotide comprises a first phase comprising particles containing an oligonucleotide and a penetration enhancer, and a second phase comprising particles coated with a release-retarding agent and containing penetration enhancer.

A variety of bile salts also function as penetration enhancers to facilitate the uptake and bioavailability of drugs. The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (CDCA, sodium chenodeoxycholate), ursodeoxycholic acid (UDCA), sodium tauro-24,25-dihydrofusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1; Yamamoto et al., J. Pharm. Exp. Ther., 1992, 263, 25; Yamashita et al., J. Pharm. Sci., 1990, 79, 579).

In some embodiments, penetration enhancers useful in some embodiments of present invention are mixtures of penetration enhancing compounds. One such penetration enhancer is a mixture of UDCA (and/or CDCA) with capric and/or lauric acids or salts thereof e.g. sodium. Such mixtures are useful for enhancing the delivery of biologically active substances across mucosal membranes, in particular intestinal mucosa. Other penetration enhancer mixtures comprise about 5-95% of bile acid or salt(s) UDCA and/or CDCA with 5-95% capric and/or lauric acid. Particular penetration enhancers are mixtures of the sodium salts of UDCA, capric acid and lauric acid in a ratio of about 1:2:2 respectively. Another such penetration enhancer is a mixture of capric and lauric acid (or salts thereof) in a 0.01:1 to 1:0.01 ratio (mole basis). In particular embodiments capric acid and lauric acid are present in molar ratios of e.g. about 0.1:1 to about 1:0.1, in particular about 0.5:1 to about 1:0.5.

Other excipients include chelating agents, i.e. compounds that remove metallic ions from solution by forming complexes therewith, with the result that absorption of oligonucleotides through the alimentary and other mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315). Chelating agents of the invention include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., Critical Reviews in Therapeutic Drug Carrier Systems, 1991, page 92; Muranishi, Critical Reviews in Therapeutic Drug Carrier Systems, 1990, 7, 1; Buur et al., J. Control Rel., 1990, 14, 43).

As used herein, non-chelating non-surfactant penetration enhancers may be defined as compounds that demonstrate insignificant activity as chelating agents or as surfactants but that nonetheless enhance absorption of oligonucleotides through the alimentary and other mucosal membranes (Muranishi, Critical Reviews in Therapeutic Drug Carrier Systems, 1990, 7, 1). This class of penetration enhancers includes, but is not limited to, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621).

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (PCT Application WO 97/30731), can be used.

Some oral oligonucleotide compositions also incorporate carrier compounds in the formulation. As used herein, "carrier compound" or "carrier" can refer to a nucleic acid, or analog thereof, which may be inert (i.e., does not possess biological activity per se) or may be necessary for transport, recognition or pathway activation or mediation, or is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'-isothiocyano-stilbene-2,2'-disulfonic acid (Miyao et al., Antisense Res. Dev., 1995, 5, 115; Takakura et al., Antisense & Nucl. Acid Drug Dev., 1996, 6, 177).

A "pharmaceutical carrier" or "excipient" may be a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB); and wetting agents (e.g., sodium lauryl sulphate, etc.).

Oral oligonucleotide compositions may additionally contain other adjunct components conventionally found in pharmaceutical compositions, at their art-established usage levels. Thus, for example, the compositions may contain additional, compatible, pharmaceutically-active materials such as, for example, antipuritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the present invention.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, from 0.1 µg to 10 g per kg of body weight, from 1.0 µg to 1 g per kg of body weight, from 10.0 µg to 100 mg per kg of body weight, from 100 µg to 10 mg per kg of body weight, or from 1 mg to 5 mg per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

The effects of treatments with therapeutic compositions can be assessed following collection of tissues or fluids from a patient or subject receiving said treatments. It is known in the art that a biopsy sample can be procured from certain tissues without resulting in detrimental effects to a patient or subject. In certain embodiments, a tissue and its constituent cells comprise, but are not limited to, blood (e.g., hematopoietic cells, such as human hematopoietic progenitor cells, human hematopoietic stem cells, $CD34^+$ cells $CD4^+$ cells), lymphocytes and other blood lineage cells, bone marrow, breast, cervix, colon, esophagus, lymph node, muscle, peripheral blood, oral mucosa and skin. In other embodiments, a fluid and its constituent cells comprise, but are not limited to, blood, urine, semen, synovial fluid, lymphatic fluid and cerebro-spinal fluid. Tissues or fluids procured from patients can be evaluated for expression levels of the target mRNA or protein. Additionally, the mRNA or protein expression levels of other genes known or suspected to be associated with the specific disease state, condition or phenotype can be assessed. mRNA levels can be measured or evaluated by real-time PCR, Northern blot, in situ hybridization or DNA array analysis. Protein levels can be measured or evaluated by ELISA, immunoblotting, quantitative protein assays, protein activity assays (for example, caspase activity assays) immunohistochemistry or immunocytochemistry. Furthermore, the effects of treatment can be assessed by measuring biomarkers associated with the disease or condition in the aforementioned tissues and fluids, collected from a patient or subject receiving treatment, by routine clinical methods known in the art. These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, (5'-O-(4,4'-Dimethoxytriphenylmethyl)-2'-deoxy-$N^4$-benzoyl-5-methylcytidin-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, (5'-O-(4,4'-Dimethoxytriphenylmethyl)-2'-O-(2-methoxyethyl)-$N^4$-benzoyl-5-methylcytidin-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-$N^6$-benzoyladenosin-3'-O-yl)-2-cyanoethyl-N,N-diisopropylphosphoramidite (MOE A amdite), (5'-O-(4,4'-Dimethoxytriphenylmethyl)-2'-O-(2-methoxyethyl)-$N^4$-isobutyrylguanosin-3'-O-yl)-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O—(N,N dimethylaminooxyethyl)-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy (2'-DMAEOE) nucleoside amidites, 2'-O-(2-N,N-dimethylaminoethoxy)ethyl)-5-methyl uridine, 5'-O-dimethoxytrityl-2'-O-(2-N,N-dimethylaminoethoxy)-ethyl))-5-methyl uridine and 5'-O-Dimethoxytrityl-2'-O-(2-N,N-dimethylaminoethoxy)-ethyl))-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270.

Alkyl phosphonate oligonucleotides are prepared as described in U.S. Pat. No. 4,469,863.

3'-Deoxy-3'-methylene phosphonate oligonucleotides are prepared as described in U.S. Pat. No. 5,610,289 or 5,625,050.

Phosphoramidite oligonucleotides are prepared as described in U.S. Pat. No. 5,256,775 or U.S. Pat. No. 5,366,878.

Alkylphosphonothioate oligonucleotides are prepared as described in published PCT applications PCT/US94/00902 and PCT/US93/06976 (published as WO 94/17093 and WO 94/02499, respectively).

3'-Deoxy-3'-amino phosphoramidate oligonucleotides are prepared as described in U.S. Pat. No. 5,476,925.

Phosphotriester oligonucleotides are prepared as described in U.S. Pat. No. 5,023,243.

Borano phosphate oligonucleotides are prepared as described in U.S. Pat. Nos. 5,130,302 and 5,177,198.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289.

Formacetal and thioformacetal linked oligonucleosides are prepared as described in U.S. Pat. Nos. 5,264,562 and 5,264,564.

Ethylene oxide linked oligonucleosides are prepared as described in U.S. Pat. No. 5,223,618.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleotide at the 3'-end of the chain is covalently attached to a solid support. The nucleotide precursor, a ribonucleoside phosphoramidite, and activator are added, coupling the second base onto the 5'-end of the first nucleotide. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe et al., J. Am. Chem. Soc., 1998, 120, 11820-11821; Matteucci et al., J. Am. Chem. Soc., 1981, 103, 3185-3191; Beaucage et al., Tetrahedron Lett., 1981, 22, 1859-1862; Dahl et al., Acta Chem. Scand,. 1990, 44, 639-641; Reddy et al., Tetrahedrom Lett., 1994, 25, 4311-4314; Wincott et al., Nucleic Acids Res., 1995, 23, 2677-2684; Griffin et al., Tetrahedron, 1967, 23, 2301-2313; Griffin et al., Tetrahedron, 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 300 of each of the complementary strands of RNA oligonucleotides (50 uM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid, or for diagnostic or therapeutic purposes.

Example 4

Synthesis of Chimeric Compounds

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers."

(2'-O-Me)-(2'-deoxy)-(2'-O-Me) Chimeric Phosphorothioate Oligonucleotides

Chimeric oligonucleotides having phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH$_4$OH) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

target exportin 5. The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. These overhangs can range from 2 to 6 nucleobases and these nucleobases may or may not be complementary to the target nucleic acid. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO:142) and having a two-nucleobase overhang of deoxythymidine (dT) would have the following structure:

```
cgagaggcggacgggaccgTT  Antisense Strand (SEQ ID NO: 143)
|||||||||||||||||||
                TTgctctccgcctgccctggc  Complement (SEQ ID NO: 144)
```

(2'-O-(2-Methoxyethyl))-(2'-deoxy)-(2'-O-(Methoxyethyl)) Chimeric Phosphorothioate Oligonucleotides (2'-O-(2-methoxyethyl))-(2'-deoxy)-(-2'-O-(methoxyethyl)) chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

Overhangs can range from 2 to 6 nucleobases and these nucleobases may or may not be complementary to the target nucleic acid. In another embodiment, the duplexes may have an overhang on only one terminus.

In another embodiment, a duplex comprising an antisense strand having the same sequence CGAGAGGCGGACGG-GACCG (SEQ ID NO:142) may be prepared with blunt ends (no single stranded overhang) as shown:

```
cgagaggcggacgggaccg  Antisense Strand (SEQ ID NO: 145)
|||||||||||||||||||
gctctccgcctgccctggc  Complement (SEQ ID NO: 146)
```

(2'-O-(2-Methoxyethyl)Phosphodiester)-(2'-deoxy Phosphorothioate)-(2'-O-(2-Methoxyethyl)Phosphodiester) Chimeric Oligonucleotides (2'-O-(2-methoxyethyl phosphodiester)-(2'-deoxy phosphorothioate)-(2'-O-(methoxyethyl)phosphodiester) chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065.

Example 5

Design and Screening of Duplexed Antisense Compounds Targeting Exportin 5

In accordance with the present invention, a series of nucleic acid duplexes comprising the antisense compounds of the present invention and their complements can be designed to The RNA duplex can be unimolecular or bimolecular; i.e, the two strands can be part of a single molecule or may be separate molecules.

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 μM. Once diluted, 30 μL of each strand is combined with 15 μL of a 5× solution of annealing buffer. The final concentration of said buffer is 100 mM potassium acetate, 30 mM HEPES-KOH pH 7.4, and 2 mM magnesium acetate. The final volume is 75 μL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate exportin 5 expression. When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., J. Biol. Chem. 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment with Antisense Compounds:

When cells reached 65-75% confluency, they were treated with oligonucleotide. For cells grown in 96-well plates, wells were washed once with 100 µL OPTI-MEM™-1 reduced-serum medium (Invitrogen Corporation, Carlsbad, Calif.) and then treated with 130 µL of OPTI-MEM™-1 containing 3.75 µg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS13920 (TCCGTCATCGCTCCT-CAGGG, SEQ ID NO:1) which is targeted to human H-ras, or ISIS18078, (GTGCGCGCGAGCCCGAAATC, SEQ ID NO:2) which is targeted to human Jun-N-terminal kinase-2 (JNK2). Both controls are 2'-O-methoxyethyl gapmers (2'-O-methoxyethyl shown in bold) with a phosphorothioate backbone. For mouse or rat cells the positive control oligonucleotide is ISIS15770, ATGCATTCTGCCCCCAAGGA, SEQ ID NO:3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS13920), JNK2 (for ISIS18078) or c-raf (for ISIS15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of Exportin 5 Expression

Antisense modulation of exportin 5 expression can be assayed in a variety of ways known in the art. For example, exportin 5 mRNA levels can be quantitated by, e.g., Northern blot analysis, competitive polymerase chain reaction (PCR), or real-time PCR (RT-PCR). Real-time quantitative PCR is presently desired. RNA analysis can be performed on total cellular RNA or poly(A)+ mRNA. One method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of exportin 5 can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to exportin 5 can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays for the Use of Exportin 5 Inhibitors

Once exportin 5 inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of exportin 5 in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with exportin 5 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the exportin 5 inhibitors. Hallmark genes, or those genes suspected to be associated with a specific disease state, condition, or phenotype, are measured in both treated and untreated cells.

Example 12

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 μL cold PBS. 150 μL Buffer RLT was added to each well and the plate vigorously agitated for 20 seconds. 150 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 μL of Buffer RW1 was added to each well of the RNEASY 96™ plate and incubated for 15 minutes and the vacuum was again applied for 1 minute. An additional 500 μL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of Exportin 5 mRNA Levels

Quantitation of exportin 5 mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

Gene target quantities are obtained by real-time PCR. Prior to the real-time PCR, isolated RNA is subjected to a reverse transcriptase (RT) reaction, for the purpose of generating complementary DNA (cDNA). Reverse transcriptase and PCR reagents were obtained from Invitrogen Corporation, (Carlsbad, Calif.). RT-PCR reactions were carried out by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension). The method of obtaining gene target quantities by RT, real-time PCR is herein referred to as real-time PCR.

Gene target quantities obtained by real time real time PCR are normalized using either the expression level of GAPDH, a gene whose expression is constant, or by quantifying total RNA using RiboGreen™ (Molecular Probes, Inc. Eugene, Oreg.). GAPDH expression was quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and primers to human exportin 5 were designed to hybridize to a human exportin 5 sequence, using published sequence information (GenBank accession number NM_020750.1; SEQ ID NO:4). For human exportin 5 the PCR primers were:

forward primer: CACCATCTTTGAACCCTGAATCA (SEQ ID NO:5)
reverse primer: TAGAGATCGGCTACAAAGGGAAA (SEQ ID NO:6)
and the PCR probe was:
FAM-CTTTTGGGCATCCTTCCTCGGCC-TAMRA (SEQ ID NO:7)
where FAM is the fluorescent dye and TAMRA is the quencher dye. For human GAPDH the PCR primers were:
forward primer: GAAGGTGAAGGTCGGAGTC (SEQ ID NO:8)
reverse primer: GAAGATGGTGATGGGATTTC (SEQ ID NO:9)
and the PCR probe was:
5' JOE-CAAGCTTCCCGTTCTCAGCC-TAMRA 3' (SEQ ID NO:10)
where JOE is the fluorescent reporter dye and TAMRA is the quencher dye.

Example 14

Northern Blot Analysis of Exportin 5 mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human exportin 5, a human exportin 5 specific probe was prepared by PCR using the forward primer CACCATCTTTGAACCCTGAATCA (SEQ ID NO:5) and the reverse primer TAGAGATCGGCTACAAAGGGAAA (SEQ ID NO:6). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Exportin 5 Expression by Chimeric Phosphorothioate Oligonucleotides Having 2'-MOE Wings and a Deoxy Gap In accordance with the present invention, a series of antisense compounds was designed to target different regions of the human exportin 5 RNA, using published sequences (GenBank accession number NM_020750.1; SEQ ID NO:4, nucleotides 34286799 to 34341191 of the sequence with Genbank accession number NT 007592.13, the complement of which is SEQ ID NO:11, and GenBank accession number BM833885.1; SEQ ID NO:12). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-O-methoxyethyl nucleotides, also known as 2'-MOE nucleotides. The internucleoside (backbone) linkages are phosphorothioate (P=S) throughout the oligonucleotide. All cytidine residues are 5-methylcytidines. The compounds were analyzed for their effect on human exportin 5 mRNA levels by quantitative real-time PCR as described in other examples herein. Data are averages from two experiments in which T-24 cells were treated with 40 nM of the antisense oligonucleotides of the present invention. The control oligonucleotide ISIS18078 (SEQ ID NO: 2) was used for this assay. If present, "N.D." indicates "no data".

TABLE 1

Inhibition of human exportin 5 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 350493 | Intron 4: Exon 5 junction | 11 | 5627 | ttcctacaccaatagaaata | 0 | 13 |
| 350494 | Intron 7 | 11 | 9355 | caagaaccatgcagcctgat | 41 | 14 |
| 350495 | Exon 9: Intron 9 junction | 11 | 14072 | actagctcaccagcaatgca | 13 | 15 |
| 350496 | Intron 11 | 11 | 16751 | ttggaatcttcctgactcaa | 45 | 16 |
| 350497 | Intron 14: Exon 15 junction | 11 | 24865 | caggaatttcctgtaacaaa | 0 | 17 |
| 350498 | Intron 18: Exon 19 junction | 11 | 28611 | tgacagcactctgaaggttg | 25 | 18 |
| 350499 | Intron 21 | 11 | 44379 | cactaagatgtgtagcagct | 76 | 19 |
| 350500 | Exon 31: Intron 31 junction | 11 | 51847 | catgacctacccaatgcaa | 0 | 20 |

TABLE 1-continued

Inhibition of human exportin 5 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 350501 | 5'UTR | 4 | 19 | acaccactgcagtcccggga | 54 | 21 |
| 350502 | Start Codon | 4 | 56 | atccatcgccatgcctagcg | 57 | 22 |
| 350503 | Coding | 4 | 103 | atgaccgtcaccgctttcac | 36 | 23 |
| 350504 | Coding | 4 | 108 | ccatcatgaccgtcaccgct | 53 | 24 |
| 350505 | Coding | 4 | 144 | gggcttccagccggtagcgc | 32 | 25 |
| 350506 | Coding | 4 | 149 | cttgagggcttccagccggt | 59 | 26 |
| 350507 | Coding | 4 | 154 | caaaacttgagggcttccag | 31 | 27 |
| 350508 | Coding | 4 | 242 | aaaatgtctgacgatggcaa | 64 | 28 |
| 350509 | Coding | 4 | 247 | aggccaaaatgtctgacgat | 50 | 29 |
| 350510 | Coding | 4 | 252 | tctgaaggccaaaatgtctg | 31 | 30 |
| 350511 | Coding | 4 | 257 | caggatctgaaggccaaaat | 54 | 31 |
| 350512 | Coding | 4 | 328 | atgacactgttcttcagata | 13 | 32 |
| 350513 | Coding | 4 | 333 | gctccatgacactgttcttc | 37 | 33 |
| 350514 | Coding | 4 | 877 | tttctgctgactgcaatgag | 58 | 34 |
| 350515 | Coding | 4 | 882 | tgccttttctgctgactgca | 70 | 35 |
| 350516 | Coding | 4 | 1065 | aatctgcacccagcaatgca | 43 | 36 |
| 350517 | Coding | 4 | 1117 | gcaagaaaagattccaggta | 55 | 37 |
| 350518 | Coding | 4 | 1127 | ggttgtgaaagcaagaaaag | 33 | 38 |
| 350519 | Coding | 4 | 1186 | tgcctgaagagggctcccca | 59 | 39 |
| 350520 | Coding | 4 | 1241 | acgaagatattttggtatta | 41 | 40 |
| 350521 | Coding | 4 | 1246 | gaagcacgaagatattttgg | 42 | 41 |
| 350522 | Coding | 4 | 1273 | aagcccatcttgaccaagtt | 0 | 42 |
| 350523 | Coding | 4 | 1278 | aaggaaagcccatcttgacc | 24 | 43 |
| 350524 | Coding | 4 | 1283 | tttagaaggaaagcccatct | 19 | 44 |
| 350525 | Coding | 4 | 1288 | tctgttttagaaggaaagcc | 46 | 45 |
| 350526 | Coding | 4 | 1348 | aaagcattgaagtcctcatc | 27 | 46 |
| 350527 | Coding | 4 | 1353 | tgaagaaagcattgaagtcc | 0 | 47 |
| 350528 | Coding | 4 | 1358 | ggagttgaagaaagcattga | 26 | 48 |
| 350529 | Coding | 4 | 1363 | cgggaggagttgaagaaagc | 12 | 49 |
| 350530 | Coding | 4 | 1921 | agcatgtcaaaattgggcag | 68 | 50 |
| 350531 | Coding | 4 | 1926 | tataaagcatgtcaaaattg | 0 | 51 |
| 350532 | Coding | 4 | 1951 | ttggagaggagttgcttcac | 53 | 52 |
| 350533 | Coding | 4 | 1956 | gctcattggagaggagttgc | 71 | 53 |
| 350534 | Coding | 4 | 2065 | gccatcagctcctctaggaa | 63 | 54 |
| 350535 | Coding | 4 | 2212 | aagctcattcgtgcacggtt | 73 | 55 |
| 350536 | Coding | 4 | 2217 | cacaaaagctcattcgtgca | 60 | 56 |
| 350537 | Coding | 4 | 2455 | tccagagccttggtgaaagg | 12 | 57 |
| 350538 | Coding | 4 | 2608 | cctgccttccctaggatatg | 29 | 58 |
| 350539 | Coding | 4 | 2613 | aagggcctgccttccctagg | 52 | 59 |
| 350540 | Coding | 4 | 2618 | catggaagggcctgccttcc | 28 | 60 |
| 350541 | Coding | 4 | 2623 | tgctgcatggaagggcctgc | 74 | 61 |
| 350542 | Coding | 4 | 2695 | ggaatattgttcaagttgac | 39 | 62 |
| 350543 | Coding | 4 | 2700 | agtcaggaatattgttcaag | 52 | 63 |
| 350544 | Coding | 4 | 3274 | agcacactggtgaaaagcca | 55 | 64 |
| 350545 | Coding | 4 | 3279 | ctttcagcacactggtgaaa | 5 | 65 |
| 350546 | Coding | 4 | 3304 | tcgtgctgcccgtgcatctg | 69 | 66 |
| 350547 | Coding | 4 | 3325 | accagggaagccatgcaccc | 64 | 67 |
| 350548 | Coding | 4 | 3448 | tttaaaagcttgcagtcaaa | 29 | 68 |
| 350549 | Coding | 4 | 3532 | cccaagggtttcccaatgca | 71 | 69 |
| 350550 | Coding | 4 | 3556 | tgaacttcttttcggaactg | 55 | 70 |
| 350551 | Coding | 4 | 3561 | taatgtgaacttcttttcgg | 54 | 71 |
| 350552 | Coding | 4 | 3655 | ggttcaaagatggtggccag | 56 | 72 |
| 350553 | Stop Codon | 4 | 3660 | ttcagggttcaaagatggtg | 37 | 73 |
| 350554 | Stop Codon | 4 | 3665 | cttgattcagggttcaaaga | 40 | 74 |
| 350555 | Stop Codon | 4 | 3670 | aaaagcttgattcagggttc | 41 | 75 |
| 350556 | Stop Codon | 4 | 3675 | tgcccaaaagcttgattcag | 60 | 76 |
| 350557 | 3'UTR | 4 | 3680 | aaggatgcccaaaagcttga | 67 | 77 |
| 350558 | 3'UTR | 4 | 3810 | ggcctgttctctccagctcc | 68 | 78 |
| 350559 | 3'UTR | 4 | 3858 | aactcccttcttgatactt | 4 | 79 |
| 350560 | 3'UTR | 4 | 4006 | gttaccattctgtacaggta | 87 | 80 |
| 350561 | 3'UTR | 4 | 4091 | ccaagagaaactctggcaca | 74 | 81 |
| 350562 | 3'UTR | 4 | 4229 | tcttgcccaaagcaaagttg | 62 | 82 |
| 350563 | 3'UTR | 4 | 4294 | ctatacttgatactgtgcca | 87 | 83 |
| 350564 | 3'UTR | 4 | 4304 | cttggaggtactatacttga | 82 | 84 |
| 350565 | 3'UTR | 4 | 4508 | gctgctcatcacagatgtag | 76 | 85 |
| 350566 | 3'UTR | 4 | 4698 | ccgtatccatgtcctctctt | 43 | 86 |
| 350567 | 3'UTR | 4 | 4854 | aaactgtagcttcagtccac | 33 | 87 |
| 350568 | 3'UTR | 4 | 4892 | ttctcaatctgaccctgcct | 18 | 88 |
| 350569 | 3'UTR | 4 | 5158 | gatgtgctttagagttaatg | 63 | 89 |
| 350570 | 5'UTR | 12 | 12 | ctcgcgctgggaagaagctg | 22 | 90 |

As shown in Table 1, SEQ ID NOs 14, 16, 19, 21, 22, 23, 24, 26, 28, 29, 31, 33, 34, 35, 36, 37, 39, 40, 41, 45, 50, 52, 53, 54, 55, 56, 59, 61, 62, 63, 64, 66, 67, 69, 70, 71, 72, 73, 74, 75, 76, 77, 78, 80, 81, 82, 83, 84, 85, 86 and 89 demonstrated at least 36% inhibition of human exportin 5 expression in this assay and are therefore suitable. SEQ ID NOs 80, 83, 84, and 19 are also suitable. The target regions to which these suitable sequences are complementary are herein referred to as "suitable target segments" and are therefore suitable for targeting by compounds of the present invention. These suitable target segments are shown in Table 2. These sequences are shown to contain thymine (T) but one of skill in the art will appreciate that thymine (T) is generally replaced by uracil (U) in RNA sequences. The sequences represent the reverse complement of the suitable antisense compounds shown in Table 1. "Target site" indicates the first (5'-most) nucleotide number on the particular target nucleic acid to which the oligonucleotide binds. Also shown in Table 2 is the species in which each of the suitable target segments was found.

TABLE 2

Sequence and position of suitable target segments identified in exportin 5.

| SITE ID | TARGET SEQ ID NO | TARGET SITE | SEQUENCE | REV COMP OF SEQ ID | ACTIVE IN | SEQ ID NO |
|---|---|---|---|---|---|---|
| 263408 | 4 | 9355 | atcaggctgcatggttcttg | 14 | H. sapiens | 91 |
| 263410 | 4 | 16751 | ttgagtcaggaagattccaa | 16 | H. sapiens | 92 |
| 263413 | 4 | 44379 | agctgctacacatcttagtg | 19 | H. sapiens | 93 |
| 263415 | 11 | 19 | tcccgggactgcagtggtgt | 21 | H. sapiens | 94 |
| 263416 | 11 | 56 | cgctaggcatggcgatggat | 22 | H. sapiens | 95 |
| 263417 | 11 | 103 | gtgaaagcggtgacggtcat | 23 | H. sapiens | 96 |
| 263418 | 11 | 108 | agcggtgacggtcatgatgg | 24 | H. sapiens | 97 |
| 263420 | 11 | 149 | accggctggaagccctcaag | 26 | H. sapiens | 98 |
| 263422 | 11 | 242 | ttgccatcgtcagacatttt | 28 | H. sapiens | 99 |
| 263423 | 11 | 247 | atcgtcagacattttggcct | 29 | H. sapiens | 100 |
| 263425 | 11 | 257 | attttggccttcagatcctg | 31 | H. sapiens | 101 |
| 263427 | 11 | 333 | gaagaacagtgtcatggagc | 33 | H. sapiens | 102 |
| 263428 | 11 | 877 | ctcattgcagtcagcagaaa | 34 | H. sapiens | 103 |
| 263429 | 11 | 882 | tgcagtcagcagaaaaggca | 35 | H. sapiens | 104 |
| 263430 | 11 | 1065 | tgcattgctgggtgcagatt | 36 | H. sapiens | 105 |
| 263431 | 11 | 1117 | tacctggaatcttttcttgc | 37 | H. sapiens | 106 |
| 263433 | 11 | 1186 | tggggagccctcttcaggca | 39 | H. sapiens | 107 |
| 263434 | 11 | 1241 | taataccaaaatatcttcgt | 40 | H. sapiens | 108 |
| 263435 | 11 | 1246 | ccaaaatatcttcgtgcttc | 41 | H. sapiens | 109 |
| 263439 | 11 | 1288 | ggctttccttctaaaacaga | 45 | H. sapiens | 110 |
| 263444 | 11 | 1921 | ctgcccaattttgacatgct | 50 | H. sapiens | 111 |
| 263446 | 11 | 1951 | gtgaagcaactcctctccaa | 52 | H. sapiens | 112 |
| 263447 | 11 | 1956 | gcaactcctctccaatgagc | 53 | H. sapiens | 113 |
| 263448 | 11 | 2065 | ttcctagaggagctgatggc | 54 | H. sapiens | 114 |
| 263449 | 11 | 2212 | aaccgtgcacgaatgagctt | 55 | H. sapiens | 115 |
| 263450 | 11 | 2217 | tgcacgaatgagcttttgtg | 56 | H. sapiens | 116 |
| 263453 | 11 | 2613 | cctagggaaggcaggccctt | 59 | H. sapiens | 117 |
| 263455 | 11 | 2623 | gcaggcccttccatgcagca | 61 | H. sapiens | 118 |
| 263456 | 11 | 2695 | gtcaacttgaacaatattcc | 62 | H. sapiens | 119 |
| 263457 | 11 | 2700 | cttgaacaatattcctgact | 63 | H. sapiens | 120 |
| 263458 | 11 | 3274 | tggcttttcaccagtgtgct | 64 | H. sapiens | 121 |
| 263460 | 11 | 3304 | cagatgcacgggcagcacga | 66 | H. sapiens | 122 |
| 263461 | 11 | 3325 | gggtgcatggcttccctggt | 67 | H. sapiens | 123 |
| 263463 | 11 | 3532 | tgcattgggaaacccttggg | 69 | H. sapiens | 124 |
| 263464 | 11 | 3556 | cagttccgaaaagaagttca | 70 | H. sapiens | 125 |
| 263465 | 11 | 3561 | ccgaaaagaagttcacatta | 71 | H. sapiens | 126 |
| 263466 | 11 | 3655 | ctggccaccatctttgaacc | 72 | H. sapiens | 127 |
| 263467 | 11 | 3660 | caccatctttgaaccctgaa | 73 | H. sapiens | 128 |
| 263468 | 11 | 3665 | tctttgaaccctgaatcaag | 74 | H. sapiens | 129 |
| 263469 | 11 | 3670 | gaaccctgaatcaagcttt | 75 | H. sapiens | 130 |
| 263470 | 11 | 3675 | ctgaatcaagcttttgggca | 76 | H. sapiens | 131 |
| 263471 | 11 | 3680 | tcaagcttttgggcatcctt | 77 | H. sapiens | 132 |
| 263472 | 11 | 3810 | ggagctggagagaacaggcc | 78 | H. sapiens | 133 |
| 263474 | 11 | 4006 | tacctgtacagaatggtaac | 80 | H. sapiens | 134 |
| 263475 | 11 | 4091 | tgtgccagagtttctcttgg | 81 | H. sapiens | 135 |
| 263476 | 11 | 4229 | caactttgcttgggcaaga | 82 | H. sapiens | 136 |
| 263477 | 11 | 4294 | tggcacagtatcaagtatag | 83 | H. sapiens | 137 |
| 263478 | 11 | 4304 | tcaagtatagtacctccaag | 84 | H. sapiens | 138 |
| 263479 | 11 | 4508 | ctacatctgtgatgagcagc | 85 | H. sapiens | 139 |
| 263480 | 11 | 4698 | aagagaggacatggatacgg | 86 | H. sapiens | 140 |
| 263483 | 11 | 5158 | cattaactctaaagcacatc | 89 | H. sapiens | 141 |

As these "suitable target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these suitable target segments and consequently inhibit the expression of exportin 5.

According to the present invention, antisense compounds include antisense oligomeric compounds, antisense oligonucleotides, siRNAs, external guide sequence (EGS) oligonucleotides, alternate splicers, and other short oligomeric compounds which hybridize to at least a portion of the target nucleic acid.

Example 16

Western Blot Analysis of Exportin 5 Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to exportin 5 is used, with a radiolabeled or fluorescently labeled secondary antibody directed against the primary antibody species. Bands are visualized using a PHOSPHORIMAGER™ (Molecular Dynamics, Sunnyvale Calif.).

What is claimed is:

1. A method of inhibiting expression of exportin 5 in a cell comprising:
 contacting said cell with an antisense compound comprising an oligonucleotide consisting of 20 linked nucleosides, wherein the oligonucleotide has a nucleobase sequence comprising at least 12 contiguous nucleobases of SEQ ID NO:83, wherein nucleosides 1-5 are 2'-O-methoxyethyl modified nucleosides, nucleosides 6-10 are 2'-deoxyribonucleosides, nucleosides 11-20 are 2'-O-methoxyethyl modified nucleosides, wherein each of the internucleoside linkages is a phosphorothioate.

2. The method of claim 1 wherein said oligonucleotide is 100% complementary to the nucleic acid molecule encoding exportin 5.

3. The method of claim 1, wherein the antisense compound inhibits exportin 5 by at least 40% as compared to saline.

4. The method of claim 1, wherein the antisense compound inhibits exportin 5 by at least 50% as compared to saline.

5. The method of claim 1, wherein the antisense compound inhibits exportin 5 by at least 60% as compared to saline.

6. The method of claim 1, wherein the nucleic acid encoding exportin 5 has the nucleobase sequence described in SEQ ID NO: 4.

* * * * *

SEQUENCE LISTING

<160> NUMBER OF SEQ ID NOS: 146

<210> SEQ ID NO 1
<211> LENGTH: 20
<212> TYPE: DNA
<213> ORGANISM: Artificial Sequence
<220> FEATURE:

<223> OTHER INFORMATION: Antisense Compound

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Compound

<400> SEQUENCE: 2
gtgcgcgcga gcccgaaatc                                              20

<210> SEQ ID NO 3
<211> LENGTH: 20
<212> TYPE: DNA
<213> ORGANISM: Artificial Sequence
<220> FEATURE:
<223> OTHER INFORMATION: Antisense Compound

<400> SEQUENCE: 3
atgcattctg cccccaagga                                              20

<210> SEQ ID NO 4
<211> LENGTH: 5231
<212> TYPE: DNA
<213> ORGANISM: H. sapiens
<220> FEATURE:
<221> NAME/KEY: CDS
<222> LOCATION: (64)...(3678)

<400> SEQUENCE: 4
agctgtcgtg cctcgtggtc ccgggactgc agtggtgtgc gctctcggcg cgtggcgcta     60 ggc atg gcg atg gat caa gta aac gcg ctg tgc gag cag ctg gtg aaa    108
    Met Ala Met Asp Gln Val Asn Ala Leu Cys Glu Gln Leu Val Lys
    1               5                   10                  15 gcg gtg acg gtc atg atg gac ccc aac tcc acc cag cgc tac cgg ctg    156
Ala Val Thr Val Met Met Asp Pro Asn Ser Thr Gln Arg Tyr Arg Leu
                20                  25                  30 gaa gcc ctc aag ttt tgt gag gag ttt aaa gaa aag tgt cct atc tgt    204
Glu Ala Leu Lys Phe Cys Glu Glu Phe Lys Glu Lys Cys Pro Ile Cys
            35                  40                  45 gtc ccc tgt ggc ttg agg ttg gct gag aaa aca caa gtt gcc atc gtc    252
Val Pro Cys Gly Leu Arg Leu Ala Glu Lys Thr Gln Val Ala Ile Val
        50                  55                  60 aga cat ttt ggc ctt cag atc ctg gaa cac gtt gtc aag ttt cgg tgg    300
Arg His Phe Gly Leu Gln Ile Leu Glu His Val Val Lys Phe Arg Trp
    65                  70                  75 aac ggc atg tct cga ttg gag aag gta tat ctg aag aac agt gtc atg    348
Asn Gly Met Ser Arg Leu Glu Lys Val Tyr Leu Lys Asn Ser Val Met
80                  85                  90                  95 gag ctg att gca aat gga aca ttg aac att ttg gaa gag gag aac cat    396
Glu Leu Ile Ala Asn Gly Thr Leu Asn Ile Leu Glu Glu Glu Asn His
                100                 105                 110 att aaa gat gct ctg tct cga att gta gtg gaa atg atc aag cga gag    444
Ile Lys Asp Ala Leu Ser Arg Ile Val Val Glu Met Ile Lys Arg Glu
            115                 120                 125 tgg cca cag cat tgg cct gac atg cta ata gaa ttg gac act ctt tcc    492
Trp Pro Gln His Trp Pro Asp Met Leu Ile Glu Leu Asp Thr Leu Ser
        130                 135                 140 aaa caa ggg gaa aca cag aca gaa ttg gtg atg ttt atc ctt ttg cga    540

```
Lys Gln Gly Glu Thr Gln Thr Glu Leu Val Met Phe Ile Leu Leu Arg
    145                 150                 155 ctg gca gag gat gta gtg act ttt cag aca ctt ccc cct caa aga aga      588
Leu Ala Glu Asp Val Val Thr Phe Gln Thr Leu Pro Pro Gln Arg Arg
160                 165                 170                 175 agg gac atc cag caa aca tta acc cag aac atg gaa agg atc ttc agt      636
Arg Asp Ile Gln Gln Thr Leu Thr Gln Asn Met Glu Arg Ile Phe Ser
                180                 185                 190 ttt ctg ctt aac aca ctt caa gaa aat gta aac aag tat cag caa gtg      684
Phe Leu Leu Asn Thr Leu Gln Glu Asn Val Asn Lys Tyr Gln Gln Val
            195                 200                 205 aag aca gat act tct cag gag tca aag gcg caa gca aac tgt cga gta      732
Lys Thr Asp Thr Ser Gln Glu Ser Lys Ala Gln Ala Asn Cys Arg Val
        210                 215                 220 gga gtt gca gca ctg aat act cta gca ggc tat att gac tgg gtg tct      780
Gly Val Ala Ala Leu Asn Thr Leu Ala Gly Tyr Ile Asp Trp Val Ser
    225                 230                 235 atg agt cac atc act gct gaa aac tgt aaa ctc ctg gag ata ctg tgt      828
Met Ser His Ile Thr Ala Glu Asn Cys Lys Leu Leu Glu Ile Leu Cys
240                 245                 250                 255 ttg ctg ttg aat gaa cag gaa ctt cag ttg gga gcc gct gag tgt ctt      876
Leu Leu Leu Asn Glu Gln Glu Leu Gln Leu Gly Ala Ala Glu Cys Leu
                260                 265                 270 ctc att gca gtc agc aga aaa ggc aag ttg gaa gac cgg aag ccc ttg      924
Leu Ile Ala Val Ser Arg Lys Gly Lys Leu Glu Asp Arg Lys Pro Leu
            275                 280                 285 atg gtc tta ttt gga gat gtt gcc atg cat tat ata ctc tcc gcc gca      972
Met Val Leu Phe Gly Asp Val Ala Met His Tyr Ile Leu Ser Ala Ala
        290                 295                 300 cag act gct gat gga gga ggt ttg gta gaa aaa cac tac gtc ttt ctg     1020
Gln Thr Ala Asp Gly Gly Gly Leu Val Glu Lys His Tyr Val Phe Leu
    305                 310                 315 aag agg ctc tgt cag gtg ttg tgt gcg ctg ggc aat cag ctg tgt gca     1068
Lys Arg Leu Cys Gln Val Leu Cys Ala Leu Gly Asn Gln Leu Cys Ala
320                 325                 330                 335 ttg ctg ggt gca gat tct gat gta gaa aca cca tca aac ttt gga aaa     1116
Leu Leu Gly Ala Asp Ser Asp Val Glu Thr Pro Ser Asn Phe Gly Lys
                340                 345                 350 tac ctg gaa tct ttt ctt gct ttc aca acc cat cca agt cag ttt cta     1164
Tyr Leu Glu Ser Phe Leu Ala Phe Thr Thr His Pro Ser Gln Phe Leu
            355                 360                 365 cgc tct tca act cag atg act tgg gga gcc ctc ttc agg cat gaa atc     1212
Arg Ser Ser Thr Gln Met Thr Trp Gly Ala Leu Phe Arg His Glu Ile
        370                 375                 380 ctg tcc cgt gat cct ttg cta tta gca ata ata cca aaa tat ctt cgt     1260
Leu Ser Arg Asp Pro Leu Leu Leu Ala Ile Ile Pro Lys Tyr Leu Arg
    385                 390                 395 gct tcc atg act aac ttg gtc aag atg ggc ttt cct tct aaa aca gac     1308
Ala Ser Met Thr Asn Leu Val Lys Met Gly Phe Pro Ser Lys Thr Asp
400                 405                 410                 415 agc cct agc tgt gaa tat tct cgg ttt gat ttt gat agc gat gag gac     1356
Ser Pro Ser Cys Glu Tyr Ser Arg Phe Asp Phe Asp Ser Asp Glu Asp
                420                 425                 430 ttc aat gct ttc ttc aac tcc tcc cga gca caa caa gga gag gtg atg     1404
Phe Asn Ala Phe Phe Asn Ser Ser Arg Ala Gln Gln Gly Glu Val Met
            435                 440                 445 agg ttg gca tgt cgt ttg gat ccc aaa act agc ttc cag atg gct ggg     1452
Arg Leu Ala Cys Arg Leu Asp Pro Lys Thr Ser Phe Gln Met Ala Gly
        450                 455                 460 gag tgg cta aag tat caa cta tca act ttt ctt gat gct ggt tct gtg     1500
Glu Trp Leu Lys Tyr Gln Leu Ser Thr Phe Leu Asp Ala Gly Ser Val
```

-continued

| | | | | | | | | | | | | | | | | |
|---|---|---|---|---|---|---|---|---|---|---|---|---|---|---|---|---|
| Glu | Trp | Leu | Lys | Tyr | Gln | Leu | Ser | Thr | Phe | Leu | Asp | Ala | Gly | Ser | Val | |
| | 465 | | | | 470 | | | | 475 | | | | | | | |

```
aat tct tgt tct gca gtt gga act gga gaa gga agc ctc tgt tcc gtc     1548
Asn Ser Cys Ser Ala Val Gly Thr Gly Glu Gly Ser Leu Cys Ser Val
480             485                 490                 495 ttc tca cct tca ttc gtg cag tgg gaa gcc atg act ctt ttt ttg gaa     1596
Phe Ser Pro Ser Phe Val Gln Trp Glu Ala Met Thr Leu Phe Leu Glu
            500                 505                 510 agt gtt atc acc cag atg ttt cga aca cta aat aga gaa gaa att cct     1644
Ser Val Ile Thr Gln Met Phe Arg Thr Leu Asn Arg Glu Glu Ile Pro
        515                 520                 525 gtt aat gat gga ata gag cta ttg cag atg gtt ctg aac ttt gat acc     1692
Val Asn Asp Gly Ile Glu Leu Leu Gln Met Val Leu Asn Phe Asp Thr
    530                 535                 540 aag gat ccc ctc atc ctg tcc tgc gtc ctt act aat gtc tct gca ctc     1740
Lys Asp Pro Leu Ile Leu Ser Cys Val Leu Thr Asn Val Ser Ala Leu
545                 550                 555 ttt cca ttt gtc acc tac aga cca gag ttc ctg ccc cag gtc ttc tct     1788
Phe Pro Phe Val Thr Tyr Arg Pro Glu Phe Leu Pro Gln Val Phe Ser
560                 565                 570                 575 aag cta ttt tca tct gtc act ttt gaa act gtt gaa gaa agt aag gcc     1836
Lys Leu Phe Ser Ser Val Thr Phe Glu Thr Val Glu Glu Ser Lys Ala
            580                 585                 590 ccc aga acc cgg gca gtg agg aat gtg agg agg cat gct tgt tcc tcc     1884
Pro Arg Thr Arg Ala Val Arg Asn Val Arg Arg His Ala Cys Ser Ser
        595                 600                 605 atc atc aag atg tgt cgt gac tac ccc cag ctt gtg ctg ccc aat ttt     1932
Ile Ile Lys Met Cys Arg Asp Tyr Pro Gln Leu Val Leu Pro Asn Phe
    610                 615                 620 gac atg ctt tat aac cat gtg aag caa ctc ctc tcc aat gag cta ctc     1980
Asp Met Leu Tyr Asn His Val Lys Gln Leu Leu Ser Asn Glu Leu Leu
625                 630                 635 ctg aca caa atg gag aag tgt gcc ctc atg gaa gcc ctg gtt ctc att     2028
Leu Thr Gln Met Glu Lys Cys Ala Leu Met Glu Ala Leu Val Leu Ile
640                 645                 650                 655 agc aac caa ttt aag aac tac gag cgt cag aag gtg ttc cta gag gag     2076
Ser Asn Gln Phe Lys Asn Tyr Glu Arg Gln Lys Val Phe Leu Glu Glu
            660                 665                 670 ctg atg gca cca gtg gcc agc atc tgg ctt tct caa gac atg cac aga     2124
Leu Met Ala Pro Val Ala Ser Ile Trp Leu Ser Gln Asp Met His Arg
        675                 680                 685 gtg ctg tca gat gtt gat gct ttc att gcg tat gtg ggt aca gat cag     2172
Val Leu Ser Asp Val Asp Ala Phe Ile Ala Tyr Val Gly Thr Asp Gln
    690                 695                 700 aag agc tgt gac cca ggc ctg gag gat ccg tgt ggc tta aac cgt gca     2220
Lys Ser Cys Asp Pro Gly Leu Glu Asp Pro Cys Gly Leu Asn Arg Ala
705                 710                 715 cga atg agc ttt tgt gta tac agc att ctg ggt gtg gtg aaa cga act     2268
Arg Met Ser Phe Cys Val Tyr Ser Ile Leu Gly Val Val Lys Arg Thr
720                 725                 730                 735 tgc tgg ccc act gac cta gaa gag gcc aaa gct ggg gga ttt gtg gtg     2316
Cys Trp Pro Thr Asp Leu Glu Glu Ala Lys Ala Gly Gly Phe Val Val
            740                 745                 750 ggt tat aca tcc agt gga aat cca atc ttc cgt aac ccc tgc aca gag     2364
Gly Tyr Thr Ser Ser Gly Asn Pro Ile Phe Arg Asn Pro Cys Thr Glu
        755                 760                 765 cag att ctg aaa ctt ctt gac aat ttg ctt gcg ctt ata aga acc cac     2412
Gln Ile Leu Lys Leu Leu Asp Asn Leu Leu Ala Leu Ile Arg Thr His
    770                 775                 780 aat aca tta tat gca cca gaa atg cta gcc aaa atg gca gag cct ttc     2460
```

```
                Asn Thr Leu Tyr Ala Pro Glu Met Leu Ala Lys Met Ala Glu Pro Phe
                            785                 790                 795 acc aag gct ctg gat atg ctt gac gcg gaa aaa tct gct ata tta gga          2508
Thr Lys Ala Leu Asp Met Leu Asp Ala Glu Lys Ser Ala Ile Leu Gly
800                 805                 810                 815 tta cct caa cct ctc ttg gaa ctc aat gac tct cct gtc ttc aaa acc          2556
Leu Pro Gln Pro Leu Leu Glu Leu Asn Asp Ser Pro Val Phe Lys Thr
                820                 825                 830 gtc ttg gaa aga atg cag cgt ttc ttc tct acc ctc tat gaa aac tgt          2604
Val Leu Glu Arg Met Gln Arg Phe Phe Ser Thr Leu Tyr Glu Asn Cys
        835                 840                 845 ttt cat atc cta ggg aag gca ggc cct tcc atg cag caa gac ttc tat          2652
Phe His Ile Leu Gly Lys Ala Gly Pro Ser Met Gln Gln Asp Phe Tyr
    850                 855                 860 act gtg gag gac ctt gct acc cag ctt ctc agc tca gcc ttt gtc aac          2700
Thr Val Glu Asp Leu Ala Thr Gln Leu Leu Ser Ser Ala Phe Val Asn
865                 870                 875 ttg aac aat att cct gac tac cga ctc aga ccc atg ctt cgt gtc ttt          2748
Leu Asn Asn Ile Pro Asp Tyr Arg Leu Arg Pro Met Leu Arg Val Phe
880                 885                 890                 895 gta aag cct ctg gtg ctc ttc tgt ccc cca gag cac tat gaa gcc ctg          2796
Val Lys Pro Leu Val Leu Phe Cys Pro Pro Glu His Tyr Glu Ala Leu
                900                 905                 910 gta tcc ccc atc ctc gga cct ctt ttc acc tac ctc cat atg agg ctt          2844
Val Ser Pro Ile Leu Gly Pro Leu Phe Thr Tyr Leu His Met Arg Leu
            915                 920                 925 tct cag aaa tgg caa gtt atc aac caa agg agc ctg ctg tgt gga gaa          2892
Ser Gln Lys Trp Gln Val Ile Asn Gln Arg Ser Leu Leu Cys Gly Glu
        930                 935                 940 gat gag gct gca gat gaa aac cca gag tct caa gag atg ctg gag gag          2940
Asp Glu Ala Ala Asp Glu Asn Pro Glu Ser Gln Glu Met Leu Glu Glu
    945                 950                 955 caa ctg gtg agg atg tta acc cga gaa gtc atg gac cta atc acg gtt          2988
Gln Leu Val Arg Met Leu Thr Arg Glu Val Met Asp Leu Ile Thr Val
960                 965                 970                 975 tgc tgt gtt tca aag aag ggt gct gac cac agt agt gct ccc cca gca          3036
Cys Cys Val Ser Lys Lys Gly Ala Asp His Ser Ser Ala Pro Pro Ala
                980                 985                 990 gat gga gac gat gaa gaa atg atg gcc aca gag gtc acc ccc tca gct          3084
Asp Gly Asp Asp Glu Glu Met Met Ala Thr Glu Val Thr Pro Ser Ala
            995                 1000                1005 atg gca gag ctt aca gac ctg ggc aaa tgt ctg atg aag cat gag gat          3132
Met Ala Glu Leu Thr Asp Leu Gly Lys Cys Leu Met Lys His Glu Asp
        1010                1015                1020 gtt tgt aca gcg cta tta att aca gcc ttc aat tcc ctg gcc tgg aaa          3180
Val Cys Thr Ala Leu Leu Ile Thr Ala Phe Asn Ser Leu Ala Trp Lys
    1025                1030                1035 gat act ctg tcc tgc cag agg aca acc tca cag ctc tgc tgg cct ctc          3228
Asp Thr Leu Ser Cys Gln Arg Thr Thr Ser Gln Leu Cys Trp Pro Leu
1040                1045                1050                1055 ctc aaa caa gtg ctg tca ggg aca ctg ctc gca gat gca gtt acg tgg          3276
Leu Lys Gln Val Leu Ser Gly Thr Leu Leu Ala Asp Ala Val Thr Trp
                1060                1065                1070 ctt ttc acc agt gtg ctg aaa ggc tta cag atg cac ggg cag cac gac          3324
Leu Phe Thr Ser Val Leu Lys Gly Leu Gln Met His Gly Gln His Asp
            1075                1080                1085 ggg tgc atg gct tcc ctg gtc cat ctg gcc ttc cag ata tat gag gca          3372
Gly Cys Met Ala Ser Leu Val His Leu Ala Phe Gln Ile Tyr Glu Ala
        1090                1095                1100 ctg cgc ccc agg tac ctg gag ata aga gct gta atg gag caa atc cct          3420
```

```
                Leu Arg Pro Arg Tyr Leu Glu Ile Arg Ala Val Met Glu Gln Ile Pro
                    1105                1110                1115 gaa ata cag aag gac tca ctg gac cag ttt gac tgc aag ctt tta aac          3468
Glu Ile Gln Lys Asp Ser Leu Asp Gln Phe Asp Cys Lys Leu Leu Asn
1120                1125                1130                1135 ccc tcc ctg cag aaa gtg gct gac aag cgc cga aag gac caa ttc aaa          3516
Pro Ser Leu Gln Lys Val Ala Asp Lys Arg Arg Lys Asp Gln Phe Lys
                1140                1145                1150 cgc ctc att gct ggt tgc att ggg aaa ccc ttg gga gag cag ttc cga          3564
Arg Leu Ile Ala Gly Cys Ile Gly Lys Pro Leu Gly Glu Gln Phe Arg
            1155                1160                1165 aaa gaa gtt cac att aag aat ctt ccc tca ctt ttc aaa aaa aca aag          3612
Lys Glu Val His Ile Lys Asn Leu Pro Ser Leu Phe Lys Lys Thr Lys
                1170                1175                1180 cca atg ctg gag acg gag gtg ctg gac aat gat ggg ggt ggc ctg gcc          3660
Pro Met Leu Glu Thr Glu Val Leu Asp Asn Asp Gly Gly Gly Leu Ala
        1185                1190                1195 acc atc ttt gaa ccc tga atcaagcttt tgggcatcct tcctcggcct                 3708
Thr Ile Phe Glu Pro  *
1200 ttcttgtcat ctcttctttc cctttgtagc cgatctctag gcccttcttg cactgccacc        3768
tcactttcca ccactgtcag cctggaaaga gatccaggtc tggagctgga gagaacaggc        3828
cctgtgcagg accagaagta attatactaa agtatcaaga aagggagtta gggcttaaac        3888
tattctgtct agatgtccca gatagttccc attctacttg agatttggc ttttccaaga         3948
aaagctagag cagagcagcc cttctcccac aagccctccc accccgtgc agccacatac         4008
ctgtacagaa tggtaactaa gggtgctgtg cccaaccctg cgactagcaa ggctcgcagc        4068
aagagcacag ccctcaacta cttgtgccag agtttctctt ggaccactcc aactcccact        4128
gagcccttt gctgctgggc tggcaggaaa ctttccccac tccctaaggg gcatgtctgg         4188
gttaggtgct aagtgctgaa gagaacttgg tcagttctct caactttgct tgggcaagaa       4248
atctggtcac ctgatgggat ccatggtaca ggctactgct aaacttggca cagtatcaag       4308
tatagtacct ccaaggacca gggctgggaa gtctttagtg ctaacatccc ctttagagtt       4368
cacacatctt gcccttccat gaatgacccc tcagtctggc ctccccagcc tcaaggtcca       4428
ctcaggcaca agagccacag taccctagat agtgtcacat gacaccgttg tcatccaagg      4488
ataatacaga ccaactaggc tacatctgtg atgagcagct agcaaagccg ctggtcttct      4548
cctaggacta agtccaggtg ccttccacaa tctcatggtc tttcaggtcc ctggttactt      4608
ttctcaaagg ccatttccaa aagaatacat gccttcacat cacaacctgt actgtgagtc     4668
cattctagag gtcactgaaa ggccctgtaa agagaggaca tggatacggg acctggccct     4728
gaggttatta ctggccgtaa ggcagagtta atccatacag aaaccagtgt gtccatgtgc     4788
tctgcacaaa aacagacctg ttgtccatcc agtccactga caagagggtt tccccgagag     4848
ccgaagtgga ctgaagctac agtttttagc tggtgcgggc cacaggcagg gtcagattga     4908
gaagaagcaa agctgggaa gcagaagttg ggagtcttgt gttgctccct cttcctgtgt      4968
ggtgctctgg gtttctgtgg atcgtgaagg cgatctcaag agtgtttccc tccaaacctg    5028
atagctgcct attcctgtct ggttggggct gtggaggatg tagttgtatt tattgcattg    5088
taatatttt aacatcctgt gacttcatgc tagaaatttt ctattgttta tagaaacttt      5148
ttgtagaaac attaactcta aagcacatct gcatgtcagt aaaaatctca gtttcgtaca    5208
gaaaaaaaa aaaaaaaaa aaa                                               5231
```

<210> SEQ ID NO 5
<211> LENGTH: 23
<212> TYPE: DNA
<213> ORGANISM: Artificial Sequence
<220> FEATURE:
<223> OTHER INFORMATION: PCR Primer

<400> SEQUENCE: 5
caccatcttt gaaccctgaa tca                                           23

<210> SEQ ID NO 6
<211> LENGTH: 23
<212> TYPE: DNA
<213> ORGANISM: Artificial Sequence
<220> FEATURE:
<223> OTHER INFORMATION: PCR Primer

<400> SEQUENCE: 6
tagagatcgg ctacaaaggg aaa                                           23

<210> SEQ ID NO 7
<211> LENGTH: 23
<212> TYPE: DNA
<213> ORGANISM: Artificial Sequence
<220> FEATURE:
<223> OTHER INFORMATION: PCR Probe

<400> SEQUENCE: 7
cttttgggca tccttcctcg gcc                                           23

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                                19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                               20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                               20

<210> SEQ ID NO 11
<211> LENGTH: 54393
<212> TYPE: DNA
<213> ORGANISM: H. sapiens

<400> SEQUENCE: 11
agcggtccag tgagtttcga gcgagattta ttccctgtga cgacggagaa accgagaagg    60

```
gatcgtaaag gatcctgccc gggcaaccgt ccccagcagg gatcagacga gagcggcgcg      120
cccagcaatg cagccgccag actgaggtct gacagcgcgc ccgctgcgaa gggccgttga      180
cgcggctgcg caccgcggcc cttccgcctc ccgccccgcc cacctaggct caacctgcac      240
acgggagccg ccacttccgc gggcgcgtgc gcagtggcgg gccgggcgcg tgcgcagcgc      300
cggcttcttc ccagcgcgag ttgctgctaa cgctcctcct ccagcttccc accccgccg       360 cccgccgcgg cccggtacca acgggtggtc tcgccgaggg agctgtcgtg cctcgtggtc      420
ccgggactgc agtggtgtgc gctctcggcg cgtggcgcta ggcatggcga tggatcaagt      480
aaacgcgctg tgcgagcagc tggtgaaagc ggtgacggtc atgatggacc ccaactccac      540
ccagcgctac cggctggaag ccctcaaggt agctggggtc ctggcgtcct gggccggtcc      600
cgacaccctc tcccagcccc agcagctccg gcgccgcctg taactggggt agtctcccgc      660
ccacgcggcc cctggacctc ctttcccaac tccccgggac cttccccctcg cggccctccg     720 cgcctctccc aaatcgccgc cttctctact cgccgctcct gtcctttgcc tgggacactc      780
cggtccctat gctgcttctc atctcgccgc agcttcccac agccctctcc tccccctttc      840
ctcgcttctg tgcactcttg tccgcaacat gaccctcgcc cattttcatt ccccaagccc      900
gacatcccct cgccttcccg aggcgcacgt gtagatcccg cccccaacac cagcttcgtt      960
ctttatggtc tctcctgcac taaacgtttt cctgctggcc cactccctg gcctgaccg      1020 agctccagcc cctctggtac ccttatgctt atatgcttta acatctcgct aactttcgtt     1080
tgtgtcttgg acattttccg gggaaattct cgcaccccta cttctcccat gtttttgagt     1140
gtaatatttt taggctattt tgcgcaaaga taacttctac cacttacttt gcattttaac     1200
aagggcactt tggtttcctg aaagtagttt gcgtgagacc cgaatgctct gctcttggga     1260
ctgacttatg ttgcagtttg ggggtgttaa tacaattcaa gcttacttgc ccataaaaca     1320
acgtgtgtgg gctgtgagaa atggccattt aggagaaaat acttgtgctg tacatttta     1380 aagtgatgtt aacttcaaaa agagagtga ccaccacttg gaggaaatgt tacaatatgt      1440
agatgtctgc cacagggttt ggaatcagaa acaattgggt tccattagtt tggtttttat     1500
tattaatatt taaaatagac acaaaagtgg agagaatacg acagtgattc tgcatgttcc     1560
tgtcacctaa attcagcaat caaagatttt accgcattta cttttttccac cgcctatcct    1620 ctctccctgc ctcgaaggtt tttaaaagaa accctagaaa ttgttatttc acccctatgt     1680
acgtcagggg gatgtctcta acaaataatt tcttattcct ttgtgtccat tttttttccaa    1740 cactagtagg gctactgttg gccgtagcat ggaaaaaatc tggaaccatc acgctggaag     1800
gaatgtttat cagttcttta ttcataatat atatataata tatacacata aaatagagtg     1860
aacaccactt ggaggaaatg ttatatatgt gtaacttta tatattttat atttttattt      1920
ttatattaaa tatatatttt taaagcaact gtgcttggag atccacataa tattgatcta     1980
ggttttgcaa ctttaaacat atagcttagg ttggagtttc tttttgagta gggtctcact     2040
ctggttgtcc aggctggcgt gcagtggtga gatctcggct cacttcagcc ttgatttctc     2100
gagctcaagt gattctccta ccacttcagc ctcctgagta gctgggatta caggcacctg     2160
ccaccatgcc cggctaattt aaaaaaatat ttttagtggg ccgggcacag tggctcacgc     2220
ctgtaatccc agcactttgg gaggccaagg caggtgggtc acctgaggtc aggagttcaa     2280
gaccagcctg gtcaacatga tgaaaccttg tttctactaa aaatacaaaa attagctggg    2340
tgtggtggcg tgcacttgta gtcccagcta catgggctca ggaggctgag gcaggagaac     2400
tgcttgaacc tgggaagcag aggttgcagt gagccgagat catgccattg cattccagcc     2460
```

```
tgggcgacag agtgagactc cgtctcaaaa aaaaaaaaaa aaaatatata tatatatata   2520
tatttaatag agatggggtt tcgccatgtt gcctaggcta gtctcagact cctagactca   2580
agtagtccac ccatctcagc ctcccagagt gctgggacag gtgtgagcca ccgcacccgg   2640
ccctggttgg agtttcttaa gatgaaattc ttttagtccc tattctctca gccctcgaaa   2700
ggaaacacta acttttcttc tttcagtttt gtgaggagtt taaagaaaag tgtcctatct   2760
gtgtcccctg tggcttgagg ttggctgaga aaacacaagt tgccatcgtc agacattttg   2820
gccttcagat cctggaacac gttgtcaagt aaggagctct tggacattac cactgaagtc   2880
tgagagaaca gatctttata tcttatataa cctatagaga tgctgtttag gtgagtagag   2940
aagagcaatc tccaagaaga gaggaatgat cccctagatg ttatcagaac ctcacaggag   3000
ctctcattca agatttaacc tttcttttct tcagtttctt catccatgta aagtgtgtgg   3060
tacatattac ccattcaaca aatattacct gccatttagc caatacttac tgagctctga   3120
ctatatgtca ttagccctcg aagccttttt agagtaatgc aatgtatagg tcaatgaatc   3180
tctgattagg cactgtggct ttcttttttc tctctgtctt tctgagtttg tgtgccttct   3240
ctgggtggta catccaaagc aggattgtat gagaataact gaaaacccat cctaacttga   3300
ttgtcctacc ctcaacacct atcagaagag gtagccttta agacttagcc atagtttttc   3360
cagaattgtt ttgtaagcca gcacagaaaa tgactgatgt caaaactgca ttttctgaaa   3420
agcaagtaca ttgttgcagt tgacctagat gtatattcac ttttggccca tcaataaaat   3480
catgaggcaa agctgacgtg tggtacaaat cttgtgcgga ttccagttaa tggaccactg   3540
catatataaa acctttccc aagaattttt gtgttagtat tttggttaaa tgtagatcat    3600
ttttgcccat tcattgacag gtacaaaatc aaaagtataa tttcttaatg aaatctccag   3660
tgtaatcaaa tgtagaaatc catgctattc tcttgtaaag acaagacttc taaagtggtt   3720
ctattgactt tatgcatttt ggtggtcagg tttcggtgga acggcatgtc tcgattggag   3780
aaggtgtatc tgaagaacag tgtcatggag ctgattgcaa atgtaaggaa tgggtggttg   3840
ggagacatgt ttccaaggta gtttaggcaa agcgtgactt cttcaatagg agtttgtgt    3900 aaaaattcac tgcttctaaa taggtcagac agcacaagaa atcataattt aggccaggca   3960
cagtgactca cacctgtaat tctagcgctt tgggaagcca aggtaagagg atcacctgca   4020
tctaagaatt cgagagcagc ttgggcaatg cagtgagacc ccatctctac caaaaatgca   4080
aaaattagct gagcgtggtg gcgcatgcct gtggcccagc tactcaggag gctgaggtgg   4140
gaggattttc tgagcccagg aggtccaggc tgcagtgagc tgtgatggtg ccatggcact   4200
ccagcctgtg caacagagca agaccctatc tcaaaaacaa aacaaaacaa aagcagaaag   4260
cataattcag catatgtctc ttactaggtt taattaatca tgcttatgta ttgacttcta   4320
ttttttaaat tataaagaca gggcagaggg gattaaatat tttcaacaaa tcaataagat   4380
tcttagatct aaattagatt gaaacactat tttctttat tccaaacaac tactatgtga    4440
tactaatgat gaaaaacatg cagaattta agtatgcaga atgaatttgt ttcaagtatt    4500
agaatatgac tttttttttt ttttgagaca gagtctctgt tgctccggct ggattgcatt   4560
agcatgatca tagctcactg cagcctcgaa ctcctgggct caagtgatct tctcgcctta   4620
gcctcccaag tagctgggat tataggcatg tggtaccatg cccagctaat tttgttttg    4680 gttttagag agacagggtc tcactgtgtt tcccaggcta gtctggtctc aaacccctgg    4740
cctcaagcaa tcctcccacc ttggcttcc aaaatgctga gattacaggt gtgatgactg     4800
gatgactgtc tctttaaaca caaaacagaa tatgacttta aacatgttca aaattgtagc   4860
```

```
cttttttctt tcttggtttt ttttaaataa cagacatgag agatgggatc ttctaatact      4920
tctgcgtctt ctagtgttag aactattggt aaaatattca tttgcccctt cataccettc      4980 cattttacca gctactcact atactcctta tttctatact cttcctccct ggccttctgc      5040
aaactgaaac aatcaatatg agaatctttt cattttgtaa agaataatga tgtcatccta      5100
gctctcgata tgacagcctt ttaggtgatg caaccctcac ttaagcttta agcggaagag      5160
tgattagcaa gaatgcagga caagtgactc aggctgaaga acaggttcat ttgttctgtt      5220
tggtttaaaa gtaggcctgc tgataaattt tttacaactc tacagcccag cttttttctg      5280
gaagtctgga atccagtctt gcatatctct taatatctct tgttcttttt cagggaacat      5340
tgaacatttt ggaagaggag aaccatatta aagatgctct gtctcgaatt gtagtggaaa      5400
tgatcaagcg agagtggcca cagcattggc ctgacatgct aatagaattg gacactcttt      5460
ccaaacaagg ggtatgaaac acagctatat cagtttggta acttttcct tggaacaaac       5520 ttcagggttt gttgtttgat tttgtttgtg ggtttttttt tttggcaaca gaaaatagcc      5580
tttggatata cataaaatga aaagatattt tagtttttaa ctagcttatt tctattggtg      5640
taggaaacac agacagaatt ggtgatgttt atccttttgc gactggcaga ggatgtagtg      5700
acttttcaga cacttccccc tcaaagaaga agggacatcc agcaaacatt aacccagaac      5760
atggaaagga tcttcagttt tctgcttaac acacttcaag aaaatgtaaa caagtatcag      5820
caagtggtaa gggatacccc tacctataac atttctattt tccaatatga gtgttttga      5880 ttaatcttac agtaaggaac tagggtgtct aggtcagcaa aatgaaatcc tattttataa      5940
gcaaaaaaat aaaaaactag gaaatgacag aaaaactgga gctcattttc tttcttttt      6000 tttttttttt tttttttgaga cggaggctcg ctctgtcacc taggctggag tgcagtggtg      6060
tgatcccggc tcactgcaac ctctgcctcc caggttcaag cgattctcct gcctcaacct      6120
cccaagtagc tgggactaca ggcgcccgcc accaggcccg gctgattttt tgtatttcta      6180
gtagagacgg ggtttcacta tgttagccag gaaggtcttg atctcctgac ctcatgatcc      6240
gcccgcctcc caaagtgctg ggattatagg tgtgagccac ggcacctggc ctttttaaa      6300 aaaaaaaaa aaaaaaaaa aaaagatagg gatctcggct tactgcagcc tccacctcct      6360
gggattacag gcatgtgcca ccacacctgg ctaattttg tattttagt agagatggag       6420 tttcgctgtg ttagcaaggc tagtctcaaa ctcctgacct caggtggtct acccaccttg     6480
ctctcccaaa gtgctgagat tataggtgtg agccaccgag cccagccta ggtgttattc      6540 ttaattttat tttcagaagt tctttaggaa aatactaatt ttttttttt ttttggagag      6600 ggagtctcac tctgtcaccc atgctggagt gcagtggcac aatctcggct cactgcaacc      6660
tccgcctcct gggttcaagc gattctcctg cctcagcctc ccgggtagct gagattaccg      6720
gtgcctgcca ccatgcccgt ctaattttg tattttagta gagatggtgt ttcaccatgt       6780
tggtcaggct ggtcttgaac tcctgacctc aaataatccg cctgcttgg tcttccaaag      6840 tgctgggatg gtaggcgtga gccaccgcgc ctggcctaat tttgtatgct tgtaagttaa      6900
cattatgtgc ctttgtatgg atttgaaata taaggataaa aatcaaccat atttgtatat      6960
tcactgaata gccactattc tgatgtattt aacatcatat atatatgtat ttttttttgt      7020 tgttttttt ttttgagac ggagtttcac ttttgttgcc caggctggag tgcagtagtg        7080
caatcttggt tcactgcaac ctctgcctcc cgggttcgag tgattcttct gcctcagctt      7140
cccaagtagc tgggattaca ggcatgcgcc agcacaccgg ctaattttg taattttagt      7200 agagatgggg tttcaccatg ttggccagac tggtctcaaa ctcctgacct caggtgatcc      7260
```

```
acctgccttg gcctcccaga ctgctgggat tacaggcgtg agccaccacg cctggccaac    7320
atccagtatt tttgagtaca tggttttcat atacttaggc tatacataca tgttcatgaa    7380
ttgtattcat ttaattatgc ttctgacttt acttgttctc cctagggaa tatcagttat     7440 gcgtgcttag taaagttgtg ttattttcca agatgaaaaa ttgcatatat ttaagaatca    7500
ttattcaagg gcattgattt gtgggggta gaaagttatt atgtggcctt ttgctcatta     7560
aaaacactgg atctttatac ttcctttcag aagacagata cttctcagga gtcaaaggta    7620
agagctcttt ataaagtttg aaggagacct ttgaaccttt caggtgaggg gatacgtgcc    7680
cctagtggat ggtgacctca gccttgcttg tgttgtattg ttttggagac aggtcttact    7740
gttgcccagg ctggagtgca gttgtgtggt ctcagctcac tgcagccatg acctccccag    7800
ctcaagtgat cctctcacct caacttcatg agtagctggg aatataggtg cgcaccacca    7860
tgcccagcta atactttcta tagaaacagg gtctcagtgt gttgcctagg ccggtgtcaa    7920 accccctggct tcaagtgatc ctccagcctc gacctcctga agtgactgtg ggccactgca   7980
tctgtcgttt gttttttttg tttgttttg ttttgtttt tgagacggag tctcgctcac      8040
ttgcccaggc tggagtgcag tggcgcgatc tcggctcact gcaagctctg cctcctgggt    8100
tcacgccatt ctcctgcctg gcctcccgag tagctgggac tacaggtgcc gccaccaca    8160 cccagctaat tttttgtatt tttagtagag acggggtttc accatgttag ccaggatagt   8220
ctcaatctcc tgacctcatc atccgccctc ctcagcttcc caaagtgctg ggattacagg   8280
tgtgagccac catgcccagc ctgtcctttg ttctgttttt gatcactgag ctatggttga    8340
agggaagtaa aaaaaaaaa caaaaacaga cttacttttt tttttttttt ttgacacagg     8400
gtcttacttt gtcacccagg ctagagtaca gtgacgcaaa cgtggctcac tgcagcttca    8460
gcctccaggc ttcaagtgag ccttacctca acctcatgag tagctgggac tatagatgca    8520
caccatcatg cctggctaat ttttgtattt ttttggttag ggtattttt ttatttatt      8580 ttatttttg tttttttggt agacactagt tttgccatgt tgcccaggct gttgttttaa      8640
ctcctgggct cagttgattc acccaccttg gcctcccaaa gtgctggtat tgcaggtgtg    8700
tgccactgca cccagccttg ggaagtaaaa tgataagatt tggggttttg tgaaaaagat    8760
aaaatggcca cacatgccag tatggtcttg ttgttggatg ttgagaatgt cattgtttga    8820
gaagtgattg tgttccctac ctgtgactgt tacatgagta tattcttaaa aaataatttt    8880
cttagaatta gaaaatggga gttcagttat aaccactgat tccttacctg ttaccgagga    8940
cttcatggtc caaagttact tcttttctgg taggcgcaag caaactgtcg agtaggagtt    9000
gcagcactga atactctagc aggctatatt gactgggtgt ctatgagtca catcactgct    9060
gaaaactgta aactcctgga gatactgtgt ttgctgttga atgaacagga acttcagttg    9120
ggagccgctg agtgtcttct cattgcagtc agcagaaaag taagttacca cttcaaactg    9180
acttatcctc agtctctgaa gtaggctgtg tatgtgttta attgcatgtt gtggcagaaa    9240
gtcatttaaa ggtttgggtt tttttccttg gggccaactt actgcctgct tccaaccccc    9300
ttggacagga gtttgccaat attcaaggga tcctttggca gaatgtggag atttatcagg    9360
ctgcatggtt cttgaaatag ccatgatact tggcaattta cagttaacag ataaaagtaa    9420
atgtttaagt ttaaagctca cttaatgaat gtcaaggaat cttggatggt ggctacagta    9480
ggtttatatc tgtcttttt ttttttttt tttttaatt gaaacagtct tgctctgtca       9540
cccaggctgg agtgcagtgg cgtgatgttg gctcactgca acgtccgcct tccgggttca    9600
agcgattctc ctgcctcagc ttcccgagta gctaggacta taggcacacg ccaccatgcc    9660
```

```
cgactgattt ttgtattttt tagtagagat gaggttttgc catgttagcc aggctcttct   9720
cgaactcctg agctcaagtg atctgccctc ctcagcctcc taaagtgctg ggattacagg   9780
cgtgagccac tgcgccaagc ctatgtctgt cttggctaac caatggaact gtgactcttt   9840
tctccatagg aatattatct acaaatgtaa tttactttgc tgtcatatca gcattattgc   9900
ccaacacatt tatttattta tttatttatt ttttgagatg gagtctcgtt ctgttgtcta   9960
ggctggagtg cagtggcgca atctcagctc agtgcaacct ctgcctcccg ggttcaagca  10020
attctcctgc ctcagcctcc tgagtatctg ggattacagg cgtgtgccac cacacccagc  10080 taattttttgt atttttttagt agagatgggg tttcactatg ttggccaggc tggtctcgaa  10140
cttttgacct caagtgatcc acctgctttg acctcccaaa gtgctaggat tacaggtgtg  10200
agccacggca cctggcctaa ttttttgtatt tttagtagag acagggtttc accatgttga  10260
ccaggctggt ctcgaactcc tgatctcagt tgttccgcct gcctcgtcct cccaaagtgc  10320
tgggattaca ggcatgagcc accgcactcg gcctgccgaa cacatttaaa aatgtaagtt  10380
tatgcttttt cactaaactg atagttttga gaaaaatat gtagtttatc cagatttggt  10440
tttaaagagt tgggcttctt tctagtgttt cactaaaccc tggggtatat aagaaattat  10500
gaagtcaata tatttgatta tatacttaca gaagatgtcg gtactttgaa gtatagttta  10560
tatgactatg tttccctaaa attgggtcta ggcaagttg gaagaccgga agcccttgat  10620
ggtcttattt ggagatgttg ccatgcatta tatactctcc gccgcacagt gagtatcttt  10680
acttttcagt gtgttttcta atttctttgt cattttctta tcttatttgg atttatctga  10740
agttcttttt ttttttttta ttttgagatg gatctcgctc tgtcacccag gctggagtgc  10800
agtggcgcga tcttggctca ccacaacctc cgtctcctgg gatcaagcga ttctcctgcc  10860
tcagcctccc gagtagctgg gattacaggc gcaccaccat gcctggctaa ttttttctatt  10920 tttagtagag acagggtttt gccgtgctga ccgctctggt ctcaaactct tgacctcagg  10980
tggtctacct gcctcagcct cccaaagtgc tgggattaca ggagtgagcc cctgtgccca  11040
cctgaagttc ttacttaaat gctagctgtc aatcgacagt gttttggat aagaaaatga  11100 ggcattggcc agatgtggtg gctcacacct gtaattccag cactttggga gtccaaggca  11160
agtggatcac ttgaggccag gagtttgaga ccagcctggc caacacggtg aaaccccatc  11220
tctactaaaa tacaaaaatt agccagacct ggtggcgcac gcctgtaatc ccagctactc  11280
aggaggctga ggcaggagag tatcttgaac ctgggaggca gaggttgctg tgagctgaga  11340
tcacaccact ctactccaga ctgggcaaca aagtgagact ctgtctcaaa aaaaaaaaaa  11400
aaagagagaa aatgaggcag tcatggctga atgtgctagc taacatttgt aacctcagca  11460
cctggggagg ccaaggcggg aggattgatt gagtcaggag tttgagacca acctgagcaa  11520
catggcaaga gtccatctct acaaaaaaat acagaaatta gtcgggtgtg gtggtatgtg  11580
tacttgtagt cccagctact cagaaggctg aggtgggagg gtcactagag ctgggaagtc  11640
caggcaatcg tgaaccatga tcatgccact acactccagc ctgggcaaca gactgagacc  11700
ttgtctcaaa aaaatagttt ttaaaagttt ataaagttaa aaagttacag taagctaaag  11760
ttaattcatt attgaagaaa ggaagttttt ttttttttga gatggagttt cgctcttatt  11820
gcccaggctg gggtgcaatg atgcgatctc agctcactgc aacctctgcc tcccgggttc  11880
aagcgattct cctgcctcac cctcccagga agctgggatt acaggcatgc accaccatgg  11940
ccagctaatt ttgtattttt agtagaaaca gggtttctcc ctgttggtca ggctggtctt  12000
gaattcctga tctcaggtga tccacccacc tcagcctccc aaagtactgg gattataggc  12060
```

```
atgagccacc gtgcccggct ggaaaatttt ttaaataaat ttagcgggcc aggtacgctg    12120
ggtcatgctt gtgatcacag cactttagga ggccaaggca gatggaccac ctgaggtcag    12180
gagttcaaga ccagcctggc caacatggtg aaaccccatc tctactaaaa gtacaaaaat    12240
tagccgggcg tggtggtgca tgtgtgtatt cttagctact gggaggctg aggcaggaga     12300 tcgcttgaac ctgggaggcg aaagttgcag tgagccagga ttgtgcccct gcactccagc    12360
ttaggcaaca gagtgagact ccatctctaa ataaataaat aagtttagtt tagcctaagg    12420
gtacagaatt tataaagtct acagtagggt ccagtaatgt cctaggcttc cacattcact    12480
caccactcac tctggaccca cccagtacag ttttctgtcc tgcagtcatt catggtaagt    12540
gccttctaca ggtataccat cttttatcat ttataccata ttttactgt accttttctg     12600 tatttagata cacaaatact taccattgtg ttacagttgc ctgcagtatt ggctacggta    12660
acatgctata gaggtttgta gcctaggagc aataggctat gctatatagc ctagatgtgt    12720
aataggctat tcctgttgtg taagtttgtg taagtacact ctatcatgtt caaatggtga    12780
taaaatcact taacgatgca tttctcagta cacatcccca gtcgttaagt gatgcatgac    12840
tgtaagggct tccatgtact ttcttccagt tgctctagaa aatactaaag caaggccggg    12900
cccaatggct catgcctgta atccccatat tttgggaggc caagccgtga agattgcttg    12960
gacccagaag ttcaagacca gtctgggcaa catggcaaga cctcatccct acaaaaaatc    13020
aaaatgaaaa taaattagct gcgtatggtg gcatgcgctt tatagtccca gctacttggg    13080
aggctgcagt gagaggatcc cttgaagccc attagtttga ggcttcagtg agccatattt    13140
gagccactgt actccagcct aggtgtgaca gcgagatcgt gtctcaaaaa aaaagaaaaa    13200
atattaaagc atttcttgat aacatgtttc ttaccaggaa gtcaggcaga actatatatt    13260
ataagtagtt gaatctgttg caacaccatc ttttgatac tctttacttt tggtcccaag     13320
gagaaatgaa aaggtatgag gcacatgtgt tttacttaaa atctcttact acccattcta    13380
atacacattt ttcatggctt ccttccctgt agagactgca gcactgtttt aagggatcct    13440
gttaattaaa tgaataacgt tttttgggta gttactattt ttaggtccaa ttcttagttc    13500
catagacatc atgacactca tactaagtgg tgtcccgttt ctgtttgtgc tgtgggtgcc    13560
ataccacaac catggttcat aaagcggtga ttccaaccca ggtagtcaaa ctccagagat    13620
tgcattggac accataatac catcctgtcc ttcaatgttc ctaaagccta ggcctcgttt    13680
accccaaggt ccttgccttt tatgtgatac tgtcctcctc cagaagacag ctaatatagt    13740 tgctttcac actcatagtt attaattgct gtttgtgtga atagtcctat atcatttag     13800 gtcaggtttt gccaccaaat aagttaaaaa gattttaaaa aatttttaat ttagcaaagc    13860
tattggaatt ctgctgaatt acagacctaa ctaaatgact tggagaaatg agacacaaag    13920
tgatgttttt attacagcct ttttaatttt gttggtgata taaggaattc tcatcttaca    13980
ggactgctga tggaggaggt ttggtagaaa aacactacgt ctttctgaag aggctctgtc    14040
aggtgttgtg tgcgctgggc aatcagctgt gtgcattgct ggtgagctag tgtttgctt     14100 ctggagagct tcaagcccat ttgggaagag catttagaaa cttatgtttc aatgaggggt    14160
tgcaaatgtc attgatttta gcctgatggg gcagtgccat acaagttatt gcatgattct    14220
atagattaaa ttatcttaat agaatagtgt ttgagtgatc taaatttctt ttaacaataa    14280
aatagttata ccaacgtcag atatccacgt ctattattcc ataaagtcaa cgttggtttc    14340
ttgtgaattt tggtacttac agaacctcaa tctgctgagt gctttatgct tttacattct    14400
gttagcccac gaaacatgga cttgaataaa gaactctttt cccaatctaa gggatgtatt    14460
```

```
attggagcac aaaagaaaac ttgagtctga ttgacctgga aaacctgcca ttagagaaat   14520
atttaatact cagtcttata agttggaaga taggacattg aacagacat ttgcaattga    14580
tgttatatct ttttgtggtg gtttaaatgg ttagagagga tagtttcaga gataagcaac   14640
cattgagggg gccaggtgca atggctcatg cctgtaatcc cagcattttg ggagggtgag   14700
gtgggcagat cacctgaggt caagagtttg agactagcct ggccaacatg gtgaaaccct   14760
gtctctacta aaatacaaa aattagccag gcgtggtggt gcatgcctgt atcccagct    14820
actcgagagg ctgaggcagg agaattgctt gaaccctgga ggtagaggtt gcagtgagcc   14880
gagatcgtgc cactgctctc cagcctgagc aacagagtga gactccatct aaaagaaaaa   14940
aaaaagaaaa gaaactattg aagggattag gtaataggtt gggacacaga gatgtgaata   15000
ggtaaggtct gaggaagtaa tacagatttt ttttcttttct gtaatttctg aaatgagtgt   15060
tttttatttt actgtttgac cacagaatgg gttttaatga tgatgattga gtaggcaaag   15120
taatgatgat gattgagtag gcaaagtaac ctatatttta gcccttgaag tgatgccttt   15180
ctttagccaa aaggaaatac aaagtccttt tgaaacaaca ttttttgagg gtttaattta   15240
tctgttttta ttacttccct gcttttctcct ctcctgcttt tctcgatcaa caccgttaat   15300
atagtggtct tctcctacag ggtgcagatt ctgatgtaga aacaccatca aactttggaa   15360
aatacctgga atcttttctt gctttcacaa cccatccaag tcaggtaaac tttatacagg   15420
taacttctca aaagtttagt taggtgaacc aatgtcaagc actgtgtcct gaaatattat   15480
tgtagatcat gtataaaatg tgactcttca ggccttgggg aatgaccgta gtgtcatttc   15540
attaagagaa ttattggctc ttcttcctga gccaaacagt gcacttgtct aggtcagcag   15600
cttttcccctt taggtaatat tctgattgta ctcagtcaca tgtgaggtgt gtcccaggtg   15660
gtttagtact aaagttataa agatttttga acaaaagtc tgattaattg tattataaaa   15720
ttaatttcac tctgttcaaa attgtccttc taatatcact ctgagattcc agtatccttt   15780
tttgcaaaga agagaaagta gtaaaattca gctcacattc caggtaattt ccttgatcca   15840
cagcctgtct tactaacatg tggtccatag tgggtggtca ttactgataa attgcagtag   15900
agacagcttc aaagtattgt acagatttat ttctatgaaa aaatgtagtt gataactgct   15960
aagtaataat ctgggttata tagaatccaa atcctttgac gttttctttt ttttttctct   16020
ttagtttcta cgctcttcaa ctcagatgac ttggggagcc ctcttcaggc atgaaatcct   16080
gtcccgtgat ccttttgctat tagcaataat accaaaatat cttcgtgctt ccatgactaa   16140
cttggtcaag gtatataatg ggaatctaaa catgtggaat gtaggtgaat acacataata   16200
agactttgag gctgggtgcg gtggctcacg cctataatcc cagctctatg gaaggctgag   16260
gcgggaggat cgcttgagcc caggagttgg agaccagcct gtgcgacatg gcaaaacctc   16320
gtctctacta aaatacaaa aaattagca gggcatgttg gtatgcacct gtagacccag   16380
ctactgggga ggcttaaggt gggaggatca cctgagcttg ggaagttgaa gctgcattga   16440
gctgagatcg cagcactgca ctccagccta ggcaatgaga gtgagaccct gtctcggggg   16500
aaacataaaa aagactgatt ggcattatta acagcccttc ttcatcacta agattccttt   16560
actggacata ttttcttatt ccttaggaag aaatcagtcc ttactggtta ttataactgc   16620
tcttccatat gagagtactt aatatatcat aagtattggg ctaggtgcta gggcaagagc   16680
agtgaccata caatgtaata attgctattc aggggttaaa agcagaatgc tttggaagta   16740
cataggaggg ttgagtcagg aagattccaa gaggaggcaa tatctaagca ttgcttctgg   16800
aggccaagtg agagttacaa agggaaatga ggggagtgag agtggaagca aagattgctc   16860
```

```
actacctcag tagagagttg ctcatgaatt ccctgctaag agctcttgca gttgacagat    16920
tgttaatctc aatttgtaac atcagagaat ggtgcacatt caagggtccc cttattttct    16980
taaggaattt gcctagcaca tagcacacac tggtgttctg tgtttttttt tgagacggag    17040
tctcaccctg tcaccgaggc tggagtgcag tggcacgatc ttggctcact gcaacctctg    17100
cctcctgggt tcaagcaatt ctcctgcctc agcctcccaa gtagctggga ctacaggtgc    17160
ccaccaccac acttggctaa ttttttgtat tttagtagag acagggtttt actgtttttc    17220
ccaggctggt ctcaaactcc tgagctcagg caatccaccc gcctcggcct cccaaagtgc    17280
tgggattaca ggcgtgagcc accgcacccg gccacactgt gttcttattt tctgccatgg    17340
tcttcaattc ttttctgaat gaaacataca aagttctaca agtttattct cagtgttcag    17400
tatttgaggc aagtagctct cagttctttc ttccttacta catactgaat tgtcattttt    17460
tctggggacc ttaaaagaat tcaagaattt aattctccct gaggaacttg gaggatggta    17520
tcaactaaaa gtattctctt ttctaccact gaggaatact ggaactggga gcaaactgtg    17580
gacctgtgat agaactgaag tggatattta ccatacaata tctcatgcaa acgcttaact    17640
cttaaataaa ttaaaagtgc ttgaactcct gaagcttaaa aactcttttca gtgggtccac    17700 tttcatcccc taccccaatt acctttcttt ttccagatgg gctttccttc taaaacagac    17760
agccctagct gtgaatattc tcggtttgat tttgatagcg atgaggactt caatgctttc    17820
ttcaactgta agtgatgttg gccttggatt tctctcaaca gtctcagaat ggcatctagt    17880
attatgaatc atggtgcatg gtgtttgggg ttttttacgaa agatccccaa atctggatag    17940
cagcctactt attaggccct agtttcccat gcagaagag tgctggggct gtattccagg    18000
cataatattt tgttttacac cacaaacccc cacagcactt agacattgat gtttagggat    18060
ggtaaccata cttaagacgc tcttgacttt ttttcatact taggattaaa taccatctta    18120
ccttatggtt atttctttcc cccaaaaagt ggaaaaatcc atttattct aatattctag    18180 ttctgttctg tgttttctgt gccttatttc ctttttgttt gtttttttt ttgagatgga    18240 gtttcactct tgttgcccag gctggagtgc aatggcgcga tctcggctca ccacaacctc    18300
tgccttctgg gttcaagcga ttctcctgcc tcagcttccc aagtagctgg gattacaggc    18360
atgcaccacc atgcccagct aattttgcat ttttggtaga gatggggttt ctccatgttg    18420
gtcaggctgg tctcgaactc ccgacctcag gtcatctgcc cgcctcagtc tcccaaagtg    18480
ctgggattta caggtgcgaa ccaccgcgcc cagcctcctt tttttttttt tttttttttt    18540
ttttacagct ttattgagac aaaattcatt taccatacag ttcacccaca tacagtatat    18600
aatttaatgg ttttttagtat ttttacagag ttgtgcagcc atcaccacaa tcaattttag    18660
attatatttt catcaccccca aaaataaatc ctatatccac taggagtcat cccccaattc    18720
cctcatctct cccagtccta ggcaaccagt aatctacttt ctgtctctgt tttgcctatt    18780
ctgaacgttt catataaatt gaatcataca tggtctattg tgactgcctt ctttcacttg    18840
cataatgttt ttaaattcat ccaagttaca acatttatca gtacttgatt tcttttttttt    18900 ttgagatgga gtctcgctct gtcgcccagg ctggagtgca gtggcacaat ctcggctcac    18960
tgcaacctct gcctcccgga ttcaagcgat tctcctgcct cagcctcctg aatagctggg    19020
actacacaca cgtgccatca tacccagcca attttttgtg ttttttagtag agacagggt    19080 tcactgtgtt agccaggatg gtctcaatct cctgacctcg tgatccaccc gcctcggctt    19140
cccaaagtac taggattaca ggcgtaagcc accacaccca gcctttttt tttttttttt    19200 gagatggagt cttgctctgt cgcccaggct ggagtgcaat gacacactct cggctcactg    19260
```

```
caacctctgc ctctgaggtt caagcgattt ttctgcctca ccctcccaag taactgggat   19320
tataggcatg caccaccatg cccagctaat tgttttattt ttagtagaga ctgggtttca   19380
tcatgttggc caggctggtc tcgaactccc gacctcagct gattcacctg ccttggcgtc   19440
ccaaagtgct ggattatagg cgtgagccac cacacccggc cttcatttct ttttattgct   19500
aatatttcat tgtatggata taccacattt actcatttat tcatctgttg atggacattt   19560
gagttatttc cattttttgg ctattacaaa taatgctgct atgaacattt atatacaagg   19620
ttttgtttag atataagttt ttgtttatct tagatatata actaggagta gaattgctgg   19680
ataatatggc aattgcaagt ttaatatttt caggaactgc cagactattt tccacagcag   19740
ctgcaccatt ttttattacc accaacctga tttacttttt aaaaatttt ttttttttt    19800
ttttgagaca tggtctcact ctgttgtcca ggcaagagtg gtgctgcgat catggctcac   19860
tacaatcttc acctccctgg gctcagctga tcctcctacc tcactctccc aagttactgg   19920
gactatagga gcatgccacc acacctggct acttttttgta ttttttggta gagactgggt   19980
ctcactgtat tgcccaaact ggttttgaac tcttgggcac aagcagtctg cccaccttgg   20040
cctcctaaag tgctaggatt tcaggcgtga gctactgtgc ccaatcctga tttccttta   20100
attcaaacag aaatgggaga ctaagtttag tttgccactt acaggatcta gctggtaata   20160
cagtttccag agatcattta ttttcaaaaa cttctggatt cgttaataaa gttttattga   20220
gtgattatta catgcaaagc acaagtctgc aaaacagttc ctttgaatgc ttttcccta   20280
gggtggtaaa ttaataaaca ttaagtactt atttatacc agttattgat tcctgtcctt   20340
cccttggcat tttctcttgg cagcctcccg agcacaacaa ggagaggtga tgaggttggc   20400
atgtcgtttg gatcccaaaa ctagcttcca gatggctggg gagtggctaa agtatcaact   20460
atcaactttt cttgatgctg gttctgtgaa ttgtaagttt ttttcattac tgaatgttag   20520
tgaaatgtta ggacagtatc aaaactatat ataggaaatg agcctgagct atacacacat   20580
cagaacgata tacttatact attcaaaaat agctttgctc atcctggaga gggagcgttt   20640
tcattggctg acacaaagaa agcagatgac acattttaaa tttgttttaa attagggtaa   20700
aaccatgtcc ttatcagttt tgccatcatt ttccatttct aacagaatca accaattatt   20760
tattgttgat tttatttgct tcacttcagg caccagctta acaaatttca tgcgtagacc   20820
taactttaaa actttttcagc caaagtcttg catagcacta ttcctgaaat cagaaaggat   20880
ctcctgttag acataacagg aataatacag ggacttctca tatcactcag ccactccaaa   20940
gcttttgtga aattatactt tacataaatt cagaataatc cccctctacc gaatgcctca   21000
gccagttaac ttctctgtac tccaaatgtt ttgtctctca tcttaatgca tgctatatgt   21060
gtgtgacagt attaataaag caaaaaggct ggatgcagtg actcacgctt gtaatcccag   21120
cactttggga gcccaaggcg ggcagatcac ctgaggtcga gagtttgaca ccagcctgac   21180
caccttggag aaaccctgtc tctactaaaa acacaaaaaa ttagctgccg tggtggcgca   21240
tgcctgtgat cccagctact tgggaggctg aggtaggaga atcgcttgaa cccaggaggt   21300
gtaggttgcg gttagccgag atggcgccat tgtactccag cctgggcaac gagagcaaaa   21360
ctccatctca aaaaaaaaaa aaaaaaaag tgaattaact agtgcacgtc actgctttag   21420
aaaagcacca tactactggc tgacatttga gggacttaac attcagcttt atttacaatt   21480
gactctaaat tctctgatat ttggtaactt gaaaggttga ggaagcccaa atgtgttgca   21540
ctaagatgaa actagtaaat aggactacgc tgtatgtaag caagaaaagc aattggtaaa   21600
tcttaggcca ggcagggtgg ctcacgcctg taatcctagc acttcaggag gccgaggctg   21660
```

```
gggatcacct gaggtcagga gttcaagacc agcctggcca acatggcaaa accctgtctc   21720
tactaaaaac aaaaaattag ccaggcgtgg tggtgggccc ctttaatcct agctactcag   21780
gaggctgagg caggagaatc acttgaaccc aggaggtgga ggtttcagtg agccaagatc   21840
gtgccactgc actccagcct gggcaaagag cgggactcca tctcaaaaaa gaaaaaaaaa   21900
aaaaagaaaa gaaaagcggc tgggcacagt ggctcacgcc tgtaatccca gcagtttggg   21960
aggctgaggt gggtggatca caaggtcagg agtttaagac cagcctggcc aagatggtga   22020
aacctcgtct ctactaaaaa aaaaaaatac aaaaattagc cgggcatggt ggcaggtggc   22080
tgtaatccca gctacttggg aggctgaggc ggagaattgc ttcaacctgg gaggctaatg   22140
ttgcagtgag ccgagatctc gccactgccc tccagcctgg gtgacagagg agactccatc   22200
tcaaacaaac aaaaaagaa aagcagttgg taaatctttt tgcttgtgcc ttgctatttg   22260
agtgctgtgc tgtggtaata gttgtaaact tgaaggatgg cacccttctc tagacatagc   22320
ccttaaggct gtcatgaggc tattggatgt gaagcagtat tttgtatatt acattgtttc   22380
cttattggga agattcttta tggtctcaat tttaattatt tagattctca tggaaaagat   22440
tataaagggg gaggagggga gaaactaatt catgtttatc aagtgcctac taatgggcca   22500
ggcaatgttt ttgatgttca cctgcgtatt ctcattcatt actcaaaatg gttttactac   22560
aaggctcata gaggtgaatt cagaccgctc attgttagag gaggaggagg catggtagga   22620
accttcacct acctcattgc tttcagcaca catcatcttt tctttgcccc agctgagagg   22680
ggttagatta ccctgctcct tcaatcatga aattctcagg tgttctctaa ggctccattg   22740
tctctctgtg tcttctgcga tctttcaatg ctgataattg tgtgtgtgtg tgtgtgtgtg   22800
tatgtgtgtg tgtgtgtttt aaagcttgtt ctgcagttgg aactggagaa ggaagcctct   22860
gttccgtctt ctcaccttca ttcgtgcagt gggaagccat gactcttttt ttggaaagtg   22920
ttatcaccca gatgtttcga acactaaata gagaagtaag taattatttc ccatgctgac   22980
tgcatgatta ttttgacctt tttctttcct tttctctttc tattttggga cgctatatct   23040
ctctgttgct caggctgaaa tgcagtggca caatcatagc tctctgtaac ctccaactcc   23100
tgggctcaag caatcctcct acctcaggct cctgaggatc tagaactaca gttacttgcc   23160
accacacctg gctaatttat aataaaaatg gagtctgtgt tgcccaggct gatctcaaac   23220
tcctggcctc aagcgaccct cctgccttgg cctcccaaag tgctgagatt gcgggcatga   23280
cccactatgc ctggccagta aactggtagt agaataggaa aatctatgga tgtacatctt   23340
acagaagagg aaacagattt agagaggcta aatagcatac tcaagttcaa acagctaata   23400
aatggcaaaa tggggaccaa aactcaggtc tttctaactc taagcactac cacatttagt   23460
atacatttta agtaccacac tgctttagaa tactgtacgc caccagtata gtggccacct   23520
gtaggtctga aaaggagggt atgcacagag agcctcaact gtatcagtaa aatcatattt   23580
cttaaagtag gcagatgagg atttactaaa ttatagagaa atagacaaaa gatataatcc   23640
aataatgtat agaggagaac ctaaagtagc tgataagccg ggcgcagtag ctcatgcctg   23700
taatcgcagc actttgggag gccaaggctg gctgatcact tgagttcagg agttccagac   23760
caccctggcc aacatggtga aaccttgtct ctactaaaaa cacaaaaatt aactgggcat   23820
gctggtgcat gtctgtaatc ccagctactt gggaggctga ggtacaggaa tcgcttgaac   23880
ccaggaggca gaggctgcag tgagccaaaa tcacgccagt gcactccagc ctgtgtgaca   23940
gagtgggatt ctgtcttaaa aaaaagaaa agggtgggggc gcagtggctc aggcctgtaa   24000
tcctagcacg tggaggctaa ggtgggtgga tcacctgagg tcaggagctc aggaccagcc   24060
```

```
tggtcaacat ggcgaaaccc tgtctctact aaaaatacaa aaattagccg ggcatggtca    24120
tgggtgcctg taatcccagc tactcaggag gctgaggcag gagaatcact tgaacccagg    24180
aggtggaggt tgcagtgagc tgagatcgtg ccattgcact gggcaaccaa gagtgatata    24240
taaataaagt agctgataaa tatgaaaaac attcagcctc ttgatcagtt gaagaaatac    24300
aaaatttaag aggttttagg gaataataca ctgctgagaa gatggtaaga agggcacgca    24360
cagctgagta cggtggttca cacttgtaat cccaacactt tgggaggcca agatgggagg    24420
aatgcttgaa cccaggagtt tgagaccagc ctggacaata tagtgagacc tcatctctac    24480
taaaaattta aaaaattagc caggcatggt ggtgcgtgcc agtagtccca cctacttggg    24540
aggctgaggc cgtaggatca cttgaaacca ggagtttgag accagcctgg tcgacataac    24600
aacacttcta caacatctct acaaaaattt tagaaagtat ccaggcatgg tggtgcccgc    24660
ctgtagtcct agctactcag gaggctaagg caggaggatc ccttgagctc aagagtttga    24720
ggttacagtg agtgatgatt gtgccactgt gcactccagc ctaggtgaca gaatgagacc    24780
ctgtctcttt aaaagatgaa ataaaatgt agccaaaatg ttatttcta agtggaggca    24840 gccattgtca acctgtttta tgtctttgtt acaggaaatt cctgttaatg atggaataga    24900
gctattgcag atggttctga actttgatac caaggatccc ctcatcctgt cctgcgtcct    24960
tactaatgtc tctgcactct ttccatttgt cacctacaga ccagagttcc tgccccaggt    25020
cttctctaag gtataaagcc catctccttt gtaaatttta ttttgacatt tctaagttaa    25080
tttttattta ttttattttt ttggagacag gatcttgcta cattgcccag gctggactca    25140
aattactagt ctcaagggat cctcacacct cacccttctg agtagctgag actacaagca    25200
tgcacaacca tgcctggcct aggctaatta ttttgtaac tattttaaa attatgtgag    25260 gcaaactaat aaacacagct atttattcat ttattaaata tctactcagt acttactgtg    25320
gatcaggtac catgctagtg cctcactctt taggaacact ctgggaagaa aggcacaaaa    25380
acagttaatg ttacctatat ggcattgcaa tgaagacttg tataaaggag agtattagag    25440
tgtgctgtcg ggcagggagg ggatttatga gaggaaggaa cactttccag gtttccagtt    25500
cagttgacta ggtgggtgat agagccactc cctgagtcag aataccagat cacaaaggag    25560
aacgggacta aagaagagaa agcatgagta ttttggaata ctgtgtttga agaatatgta    25620
gaacatcttt atggagacat ctcacaataa attggctatt tgaggttgaa gatctagact    25680
ctagaaagta atgagataaa attaaagcat catcatcata gtagtcccac gactaaaagt    25740
gaagtcttac tgaagtgatt atgtatgtag agttaggaga catgtgagtc aagcgaggaa    25800
cctagtgaat caccatcatt ggaggagtgg agaaaaaaat gagaagcccc cacagaagga    25860
aaaagagcca gagaaatgaa gaaatgttg tgtcacaaga ccagtaggac ttcagaaaag    25920
tgggctcatt tgttgcaaat tatttgagtt ggagaatgcc cagtgagttt cttgactaca    25980
ctcttgtctg agtttaattc cataatagtg gccaagtaag cagccatatt tcattggaat    26040
gaggagtaaa tggaaataa tgaaatgaa tagaagggat agaccataca actttgata    26100 aaagaagaga gaggcgtttc catagccaag tgcttgggtg atggcatgaa ttgttctggg    26160
atcctattgt aaaatgtttt gatggtaaaa ttgtgactcc gatgactctt gtagaggtta    26220
tctgagaaaa tggacagtat gaataagctc atgcccgtag tcccagctac tcagaaggct    26280
aaagcaggag aatcagttga gcccaggaat tcaagtctag tctgggcaac atagcaagat    26340
ctcatctcta aaacaaataa acatgagtga ccttttttcc tcctctccct tagctatttt    26400
catctgtcac ttttgaaact gttgaagaaa gtaaggtaag accattaatt aaaccaatag    26460
```

```
attctaactt cttgagtaca aatgtatgaa tacctgatac tcagtttata ttttttatata  26520 aatgggaggg ggtagtaagg gtggtagatt atcatatatg ttgttttgcc actatagggc  26580
atacaagaaa catggattct tggtggctat aaatgttact ccattatact cttaggttg   26640 tgaaaaatca ttgtgaattt gccctgact gagatattca catgagtcta tgcagcacct   26700
gtatattata ttaaaagcag ctccgagttt gttgaatgtc tcttttcagg ccccagaac   26760 ccgggcagtg aggaatgtga ggaggcatgc ttgttcctcc atcatcaaga tgtgtcgtga  26820 ctaccccag cttgtgctgg taagctgctg gaccctggct gaagtagcca agtttggtta  26880
catttgtgtg taaatccagc tttcagtgta cctcacataa agaaaaaact agaaactata  26940
gctttgcatc atataagcat ccttggccgg gcatggtggc tcacacctgt aatcccaaca  27000
ctttgggaga ctgaggtggg tagatcacct gaggccaggg gttcgggacc agcctggaca  27060
acatggtgaa gtccggtctc tactaaaagt acaaaaaaat tagctgggca tggtggtgca  27120
tgcctgtaat cccagctagt caggaggctg aggcaggaga tcacttgaa ctcaggaggc   27180 ggaggttgca gtgagccaag atcacgccat tgctccagcc tgggcaacga gcgaaactcc  27240
atctcaaaaa taaataaata aacattcttg aattggtgtt ttcttagtat acttagtagt  27300
atagttagaa atgtgatggc aaatgtaatc tctcttcaaa atacaaatag ttctctgcca  27360
tatagattac taagttacc cctataattc tacaactctt tactatgtga tgatcttaat   27420
tactactgcc aaatgatgtg cctgatcttg agaaaagcag atgcaaatca caaccctttt  27480
tggggcatgg ggttataaga aatttaacat tactccagat tacaaattat ccagaaattt  27540
cttctctgaa tgcacagcag ttatctccat atatatatag atatacatat atatctatat  27600
atatatataa aacaagctga tcttttcaca gttgtagtat gggaaagtgc agttatccaa  27660
atactcaaga caagagctat cttccgccta aattgccttg cttatttagg caaaataaag  27720
acatataaca gaattaccaa ataataacct tataggcctg actttcctgg gactgctttg  27780
gttttcttct ttcttccttg agtaagccac ctctccttga aaatcagacc tttaccacct  27840
ctggcttttt ttcttttttga tctgtagccc aattttgaca tgcttataa ccatgtgaag   27900 caactcctct ccaatgagct actcctgaca caaatggaga agtgtgccct catggaagcc  27960
ctggttctca ttagcaacca atttaagaac tacgagcgtc agaaggtgtt cctagaggag  28020
ctgatggcac cagtggccag catctggctt tctcaagaca tgcacaggta aaggagatcc  28080
cttgccctga ctcttactat actcaagcac ccattttggt ttaagagcta ggcccagggt  28140
ggggtagggg ttaaggatat tgaagtgtga tggcattatc catgatatct gaagttctct   28200
aaaagcagtc ttttgtaatt taatctctgg ttcaattaga ttgtgggtgg ggagggcaca  28260
gagtgagact cctgtggtgt ctgcattgca gcaccagcac atttagaaaa atgagaacag  28320
ctaggaaggg ccatcaaacc acacagacac ttatctgtgc tcacacagta gagaaattat  28380
tttctttata ttttgaagat tatattcttg tttaattctt aaattgttac taataatatt  28440
tgggagtggg aagggaaatt taaaccttca aatgacaact gacaattagt atgattatac  28500
tcctctcact ataaaaactg ctcttaaggg ccaaataatg atagcctgtt aactcctgtg  28560
gaagaaactg tccttgttta aagtcatgat gtaacttgtt tttccccctc caaccttcag  28620
agtgctgtca gatgttgatg ctttcattgc gtatgtgggg acagatcaga agagctgtga  28680
cccaggcctg gaggatccgt gtggcttaaa ccgtgcacga gtaagacttt cctgggaatg  28740
ggaagtggca ttggccatgg gtaggagtag ggtgttgtct tttgtcaagt ttctcataga  28800
tttgtttttt ctatactggt gagaaacgtg ggagtctcca cttccctaag cttctccttt  28860
```

```
cttttcttct ttagtcttga attcttgagt tagttcccac agcagagcag atggtctttt   28920
ctatgaagtc attattttgg ctttaaggat ctctaaatag ctctgaagac tgaaggtgta   28980
atgaggaagt aggtcagaac ttggtcagca gggtgagtcc tccctgccat tgctctctgg   29040
catgtaaagt cttaagtgat ggcttaactt gcaaacctga gattttcag tgctttgcta    29100 tttaaataag cattgttcct ggctccatta tggcacaagt cccattaatt aacctggcaa   29160
gtagtaggtt gattcagagt accgtgaggg gggattagga cactagctgt caaggcccaa   29220
taagggtcaa ctcaaagaag atgaagtgat ggcatttaa acactttgtt ttggatcgta    29280
tctaagccac cttctcatca gggtcctgtg ggtgggtcac tgcagctcct agaaagacag   29340
cttactgcaa gggaagtttc cagagcctac cactggccct gaaaatggca gtgagaggat   29400
ccctcttgga cttcaccta aaggaaggga tgggggattg ccggggagca gaggattatt    29460
tcattctctc tggcctctgt gtcacttttg ccagaacctt gaatatatct aacagtattt   29520
ggtctttttt ttttttcct tttaatattt atctgtcatt cttattttc tatagatgag     29580 cttttgtgta tacagcattc tgggtgtggt gaaacgaact tgctggccca ctgacctaga   29640
agaggccaaa gctggggat ttgtggtggg ttatacatcc agtggaaatc caatcttccg    29700 taaccctgc acagagcaga ttctgaaact tcttgacaat ttgcttgcgc ttataaggtg    29760
agtcagaata atgcttttc tctgttgttt tctactttac cttaaaaatt tcaaaagttt    29820
agtctgttta catgtcttca tatcttagtg gtattaatga gggattgatt taagtcttat   29880
ttctttctag agggtgtctc agttttaaaa aaaataacat cagctctcac ttgcataaat   29940
cttaatttcc atgtgaaccc aaggggataa tcccaaaagg gcttttccca ttttgagcct   30000
cctctttgtt gttcttccat ttctttatac ttcatcccta ttttacttg taagttttat    30060 ttggtctaaa ttttttagta aaggaattgc tcattgggag cagggcagtt gccttctata   30120
atgatgcttg tctaggtggt attcatatga gctaatctga atttatcaat actgagtctg   30180
agctcagatg aaccaaacaa ccgctggctg aacatgctaa acaaggaat tataaatttt    30240 tcatctgagt ttgctagatc cttggttctc aaagctgagt cctaagacca gtagcattag   30300
catcacctga gagcttattt caaaggcaga atcaaggccc caccccagac atactaaatc   30360
agaatctgca ttttaactag atgcccagtg gtttatatac acattaaaca ttcagaatca   30420 ctgtttaga tcacatgagt taatatattc aagtggaagt aggccagtat aggcttatca    30480
gttactagat atagatattt gatgactcag ggatggtctc taaatgaaaa gataggtttt   30540
tttatataat tcagttattg gccaaagagt gcttttgta tctcacagga ttggtttttt    30600
ttttgtttgt ttgttttttt gagacagagt ctcactttgt cacccaggct gggagtgcag   30660
tggtgcaatc ttggctcact gcaacctccg cctcccaggc ttaagcgatt cttctgcctc   30720
agccacccaa gtagctggga ctacaggtgt gcaccaccac tcctggctaa ttttgtatt    30780 tttagtagag acagggcttc gccatgttag ccaggctggt ctcgaactcc tggccgcaag   30840
tgatcagtcc acctcggcct cccaaagtgc tgggactcca ggagtgagcc accacctg    30900 gcctctcaca ggatgtttaa attacattgt tagagctctg tttcagtact ttttggcccc   30960
ttctccaagg agtaaaagca gtctcaacgg ggcaaaccaa attattcatg tcgcagtgaa   31020
actctcctgg gaatagacac ccaagacctg aagcctgaga accaaagatt ttaagttaat   31080
gttgacaaat tggagggctg gagtgtctga taaagttgtc attgtggaca tgtctgtgga   31140
aatagacaat attttggcgg ggtgtggtgg ctcacacctg taatcccagc actttgggag   31200
gccaaggtgg gtcaatcact tgaggtcagg agtttcagac cagcctggcc aacatgatga   31260
```

```
aaccctgtct ctactaaaaa tacaaaaatt agctgggcat ggtggcacat gcctgtaatc   31320
ccagctactc gagaggctga ggcaggagaa tcgcttgaac ccgggaggcg gagattgcag   31380
tgagctaaga tcacgccact gcactccagc ctgggcgaca gagtgagact tccatctcaa   31440
aataaataaa taaataaata atattttctt ttgatttcta aaggaggaaa gagatctctg   31500
aaaagaagta ggacttgtac tgagagggtt aaacatttag tcaagaagag cttatttct   31560 atcgtgatgt ttttattaat agagatgggg ttttgccatg ttgcccaggc tggtctcgga   31620
cagctgagcc tgcttcagtc tcccaaagtg ctagcattac aagtgtgaac caccacaccc   31680
agccccatag tgatgttttt taaaaccaca aggttcttct gcagctagag aaacgtgaaa   31740
gtgatgaaaa tcatagggca agaagctaat cacctagacc ttttaggcc tgtggccaga   31800 atctatgtgg ccaacccaga cgtggaaaca gggttcattt ctggttgact ctagaggcca   31860
caagacaaca gtatgattat cttttttat ataattttct ttttttaaaa aagtataatc   31920
tcttttcaat ttctagtcac cttcctatca atcagtagag gaagattctc atgtgttcac   31980
tatgtctttc tccagttttt tcctctataa atttactact cctattttct atagaaagac   32040 aatgaaagt gtataattgc tgtcggtaga taagtaggtc ttgaatttat tttgcaaaca   32100
agacctgttc tgtctatcct ttcatttagg aggctaacag cagactcagc ttgactttaa   32160
ggactctatt ttcttagtct tcagatggtt atcattttga tacttttcta agagttcagt   32220
gcttttagag aattccaaaa atcaatcaaa aggcattttg aaaaatgcct agcatgtaat   32280
gatagagtag attgcttgaa tagtgtgtag ctggagctat taagagttttt gctttttag   32340 taaattttat tggctgggcg cggtagctca tgcctataat cccagcactg tgagaggcca   32400
aggcgcatgg atcacttaag gtcaacagtt cgagactagc caataaaca tggtgaaacc   32460 ccacctctac taaaaataca aaaattagcc aggcatggtg gcgggcgcct gtaatcccag   32520
ctactcggga ggctgaggca ggagaattgc ttgaacctgg gaggtggagg ttgcagtgag   32580
ccaagatcac agggaagagt cttccctgtc cctgggcaac agggaagact ccgtctcaaa   32640
aaagaaaaaa aaaattaaat aaattttatc ttgaagtgta acatttatgt agaaaagggc   32700
ttaacttgtg agtgtgtgta gatgaatttt cacaaagtgg acacattcat gtaatcagca   32760
ctcagatcaa gaagcaactt tacctaatac ctcttttcag taattacctg ccccctcaaag   32820 ataactacta ttctgatttg tatttattta tttatttact tacttactta cttttgaggc   32880
acgatcttat cctgtcgccc aggttggggt gcagtgttgc gatcacggct cactgcagcc   32940
tcgacctcat gggctcaagc agtcctccca cctcagcctc ctgagtagct aggactacag   33000
ccatgagcag ccatgcccag ctaattttta acttttggt agagataggt tctctctatg   33060
ttgctgaggc tagtcttgaa ctcatgggct caagagatcc tcccaaagtg ctgggataac   33120
agatgtgagc cacctcaccc agcccactat tctgactttt aacattttgt ccaggttttt   33180
gaactttgtg aaaatgaaat cagaagtatg cacctttgg tgtctgcctt cctttcgctc   33240
aatattttgt ttctgaggtt catccatgtt actgcatgaa tgtacttgtg tttttttgt   33300 tctccttgct tgtatgatac ttcattgtgt gaatatgctg taactattca gccttgatgg   33360
acctttgggt gatattttaa tattacatat catgctgctg ttgacattct tatgtcaaat   33420
acgttttgtg aacatatata tataattct gttggataca cacataggag tagaattcct   33480
agcttataag aaatgtgtat tttctgtttt tatagatgca acctgctttt taaagtggtt   33540
atactaattt atattcccac cagttatatg ctggagttgg gagttttaaa ttactatttt   33600
ttggctgggc acagtggctc acgcctgtaa tccaagcact ttgggaggcc gaagcaggtg   33660
```

```
aatcacttga ggtcatgagt ttgagaccag cctggccaac atggtgaaac cccgtctcta   33720
ctcaaaatac caccaccacc aacaaaaaaa attagctggg catggtggca ggtgcctgta   33780
atcccagcta ctcaggaggc tgaggtagga gaatcgcttg aacttgggag gcggaggttg   33840
cagtgagctg agatcatgtt accgtactcc agcctgggca acagggtaag actccatctc   33900
aaaaaaaaaa ttgaaaaata aataaattac tattttttta gtagagaaaa gtttgcttta   33960
agaatgtagc aaggtattca tagcacctcc tgcgtcaaat aatctgataa tagaaggtgt   34020
tgaagctgtg ctgtccagca tggaagccac ttgccacatg aaactattga gcacttgaag   34080
tattactagt caagtgttac agtactttca gaattggtct ggtaggcttt ccagttttct   34140
ctggaaagct ccttagagaa aaaaaataaa aattaaaaaa taaaaatgac tagcctgaat   34200
tgagatgaac tgtaagtata aatacacac tagatttcta aaatcggccg ggtgcggtgg   34260
ctcatgcatg taatcctagc actttgggag gctaaggcct taggcagatc acttgaggtc   34320
aagagttcaa gaccagtgtg ccaacatgg tgaaacccca tctctactaa aaatacagaa   34380
attagccagg cgtggtggtg tgcatgcttg taaccccagc tactcaaaag gttgatgcaa   34440
gagaatcact cgaacccagg agatggaggt tacagtgagc taagatcgtg ccactgcact   34500
ccagcctggg agaagaatg agactctatc tcaaaaaaga aaaaagaag tattggatta   34560 ctacagtact tacaaaatga agtactgata attactcacac tgtggatcaa ccttcaaaac   34620
attatgctaa gtgaaagaag ccagacacaa aaggccatat gttgtatgat ttcattttta   34680
tgaaatatct agagacagaa agtacattgg cgattgcctc aggttggaga ggagaagaaa   34740
gtgtagatca actgctactg cttaatgggc ctggcagtta ttttgggggc catggaaacg   34800
ttttggaacc aggtagaggt tacttatgca accctttgaa agtattaaat accactgaat   34860
tgtgaacttt aaaatggtta ggttttggtg gggatgtttt ttgttagttt tttaaagttt   34920
tgtgggtaca cagtacatac atatatttat ggggtacata agatgttttg acacaggcat   34980
gcaatgcata ataataatca catcaattaa aatggggtat ccatcccctc aagcatttat   35040
cctttgtgtt acaaacaatc cagttatagt caactgcagt tatgcttttt aaatgtacaa   35100
tcaaaattat tattgactat agtcacccta ttgtgctagg aaatactaga tcttattcat   35160
tctttgtggg tttttttgtac ccattaacaa tccctacctt accccctaacc caccactacc   35220 ctccccagcc cctctgctaa ccatccttac actctgtatg tccatgagtc gaattgttta   35280 aattttaga ttccacaaag agtgagaaca tgtgatgtgt cttctgtgc ctggcttatt   35340 tcatttagca taatgacctc cagtgctatc catattgttg caaatgacaa gatctctttt   35400
tttttttatg gctgaatagt actcctaaag tggttagttt tatgttatgt gaattatgcc   35460 tcaattttt aaaatcttaa taaaaataaa gctggttctt tgaaaatact agtgataaca   35520
tcagtaaatt caaaagctta agaaaaatgg ggctgggcat gttggctcat gcctgtaatc   35580
tcagcacttt gggaggccac agcaggaaca ttgctggaga ccagcctggg caacgtagca   35640 agacccata tcgattttt aatttatttt ttttgaaacg gagtgtcact cttgttgccc   35700
aggctggcat gcaaaggcat gatctcggct cacttcaacc tctacctccc aggttcaagc   35760
gcttctcctg tctcagcctc ctgagtagct gggattacag gtgtgtgcca ccatgcctgg   35820 ctaatttgt ttatttattt atttattttg agacggagtc ttgctctgtc gtccaggctg   35880
gagtgcagtg gcgccatctc ggctcactgc aagctctgcc tcccaggttc acggcattct   35940
cctgcttcag cctcccaagt agctgggact acaggtgccc gccacctcgc ctggctaatt   36000
ttttgtaatt ttagtagaga cagggtttca ccgtattagc caggatgatc ttgatctcct   36060
```

```
gacctcgtga tccgcccggc ctggctaatt ttgtatcttc agtagagaca gggtttcacc   36120
atgtttgcca gcctggtctt gaactcctga cctcaggtga tccccctcc ttggcctctc    36180 aaagtactgg ggttacaggc gtgcgccacc atgcccagct aattttgtat cttcagtaga   36240
gacagggttt catcatgttg gccaggctgg ttctcaaact cctgatctca ggtgatccgc   36300
ccatcttggc ctcccaaagt attgggatta taggcgtgag ccactgtgcc cagcccgtc    36360 ttctattttt aaaataaaa tatttaaaaa tggataattt ccagggaaaa tgtaacttat    36420
tctaactcaa caagatagaa aacctaaaga gatataactt catattaatt atattggtag   36480
tagttaaatt agaccaaaaa actccaggcc taaatgattt tacatgggag ttctcccaga   36540
ccttcaagga acagataatt tatctcttag acaaactatt cccaagaata gaaaaatgta   36600
gcttcttctc cgagaaaaca ccaaatggcg gatgacgccg gtgcagtggg ggggcctgga   36660
ggccctggtg gccctgggat ggggaaccgc ggtggcttcc gcagaggttt cgccagtggc   36720
atccggggcc ggggtcgcag ccgtggaccg ggccggggct gaggccgcgg agctcgcgga   36780
ggcaaggcca aagataagga gtggatgccc gtcaccaagc tgggccgctt ggtcaaggac   36840
atgaagatca agtccctgga ggagatctat ctcttctccc tgcccattaa ggaatcagag   36900
atcattgact ttttcctggg ggcctctctc aaggatgagg ttttgaagat tatgccagtg   36960
cagaagcaga cccgtgctgg ccagcgcacc aggttcaagg cgtttgttgc tatcggggac   37020
tacagtggcc acgtcggtct gggtgttaag tgctccaagg aggtggccac cgccacccgt   37080
ggggccatca tcctggccaa gctctccatt gtccccgtgc acagaggcta ctaggggaac   37140
aagatcggca agccccacac cgtccctgc aaggtgacag gccgccgtgg ctctgtgctg    37200
gtgcgcctca tccctgcacc caggggcact ggcattgtct ccgcacctgt gcccaagaag   37260
ctgctcatga tggctggtat cgatgactgc tacacctcag cccagggctg cactgccacc   37320
ctgggcaact tcgccaaggc caccttgat gccatttcta agacctacag ctacctgacc    37380
cccgacctct ggaaggagac tgtatttacc aagtctccct atcaggaatt cactgaccac   37440
ctcgtcaaga cccacaccag agtctctgtg cagcagaccc aggctccagc tgtggctaca   37500
acatagggtt tttatacaag aaaaataaag tgaattaagc gtgggaaaaa aaaaagaaa    37560 aatgtagtgc tccataactc attttatgag gcttatttat tttgatacca aaaccagaca   37620
ttaacagtac caaagaggaa aattataggc ctaaatcact tgtaaacata gagacgaaaa   37680
tcccaaatca aaagcaatat ggagctagta ataagtcttt taatataacc acatttccat   37740
tgttatatct caaaatacta ccagtaattc aatatccagt atacaatcag tattcaaata   37800
tcaccgaatg ttttccttt ttctgtttat ccacacaagg tttatatata tttaagatat    37860
ctcttagtca ctaaattagg cttagcgtgg tgcctcacgc ttgtgatctc agcagtttgg   37920
gaggccgagg caggcggatc cttgaggcta agagtttgag accaacctgg ccaacatgac   37980 aaaacccat ctctactaaa aatttaaaaa agtaaccagg tgtggtggtg cgcacctgta    38040
gtctcagcta cttgggaggc tgaggcacga gaatcacttg aacccagcag gcggaggttg   38100
cattgagctg agatcacgcc attgtactcc agcctgagcg acagagcaaa tctctgtttc   38160 aaaaaaaaa aaaaaaaaa aaaaaaaga tgtctcttag gctctaaatt tataagttcc     38220
ttgccttttt tttttttttt tttttgagac catcttgttc tgtcacccat gctggagtgc   38280
actggtgcta tctcagctca ctgcaccctc cgcctccgg gatcaagcaa ttctcctgcc    38340
tcagcctctc gactgcctca gcctctcgag tagctgggat tacaggtgtg cgccaccacg   38400
cctggctaat tttttgtatt tttagtagat acagggtttt gccatgttac ccaggctggt   38460
```

```
ctcaaactcc tgagctcaac tgatccacct gcctcagcct cccaaagtgc tgggattaca   38520
gccgtgagct accatgcctg gccctctttt tcttttcaat ttatttgttg aaaaatgtgg   38580
acttgtattt ccagagtttc ccctggtgaa attttgatga ttgcatctct ggagtattgt   38640
ttgatcttgt ctactttcct ttattttgt tattttgtta cacgtgaata tgtctagagg    38700
acatatggca ctctgcagcc tgaggaccaa atgtaagtct ccacatgttt gtaagtaaac   38760
ttccgttgga acataccttg gccattcatt tacctactgt ttatggctgc tattgcgctt   38820
caatgcagag ttgagttgtc gaggacagac accatattgc cggccaagct taaaacatgt   38880
atgaatgtga cctctggtct agaaaactga cctcatacca gttcagtttt ttagcagata   38940
atcctttgta gatgatgatg ggttcaacac aatagtaaag gtttagcctt taaaagactc   39000
ccaggtatgt attacaggtt gatctatgac agaagtaatg aaagttagaa aaagatggct   39060
gggaatagtg gctcatgcct ataatttcag cactttggga ggccagggca ggaggatctc   39120
ttggggccag gagtttgaga ccagcctggg caacacagac actttctcta caaaaaaaaa   39180
aaaaaaagtt ttaattattc acgtgtggtg gtgcacactt atagtcccag ctactcggga   39240
gcctgaggtg aagggccac ttgagcccag gagtttgagg ctgcagtgag ctatgaacac    39300
accactgcaa tccagcctgg gcagtagagt gagaccctgt ctcttaaaa aacaaaaaac    39360 aaaacaaaaa tcaattattc aatgctggga cagttggctt tctatgcaga gttgagttgt   39420
cgaggacaga caccatattg tctgtttcac cgtgttagaa aaacaatta gattcctacc    39480 agccaccaca cacagaaaaa attttcaggt gttttaaaac ccaaaaagta aagctgcttt   39540
tttttttttt tttttttttt tttttttta gatagagtct cactctgtcg tccaggctgg   39600
agtgcagtgg cgcgacccttg gctcactgca acctctgcct cccgggttca agcgattctc   39660
ctacctcagc ctcctgagta gctgggattt acaggcgtgt gccaccatgc ctggctaatt   39720
tctgtattct tagtagagac agggtttcac catgttggcc agagactggt cttgaactcc   39780
tgacctcgtg atccacccac ctcggcttcc taaagtgctg ggattacagg cataagccac   39840
cgcatctggc caaagtaaaa cttctagacc atatttacag catgaggtta gtgaatgact   39900
tttttttttt gtcgagttgg agtctcactg tgttgcgcag gctggagtgc agtggcacaa   39960
tctcggctca ctgcaatttc cgcctcctgg gttcaagcga ttcttatgcc ttgacctctc   40020
aagtagctgg gattataggc atgcaccacc acacccggct aattttttata tttttagtag   40080 agacagggtt tcaccatgtt ggccaggctg gtctcaaact cctgacctca ggtgatccgt   40140
ctgccttagc ctcccaaagt gctgggatta caggcatgag tcactgtgcc tggccagggt   40200
agcgaatgac ttttttttttt gagagggagt ctcgctctgt cacccaggct ggagtgcagt   40260
ggcacgatct tggctcacct ggattcaagt gattctcctg cctcagcctc cggagaagct   40320
gggattacag gcatgcaccg ccatactcgt ctaattttta tattttagt agagacaggg   40380 tttcaccatg ttggccaggc tggtcttgat ctcctggcct caggtgattc tccggccttg   40440
gcctccctaa gtgctgggat tacaggcgtg agccactgcg cccggcctag aatgactttt   40500
tttttttttt tttgagatg gagtctcgct ctgtcacaca ggctggagtg cagtggcgcg   40560
atttcagctc attgcaagct ccgcctcccg ggttcacgcc attctcccac ctcagccttc   40620
cgagtagctg gactacagg cgcccgccac catgtctggc taatttagct tttgtatttt    40680
tagtagagat ggggtttcac catgttaccc aggatggtct cgatctcctg acctcgtgat   40740
ccaccgcgcc cggcctctag aatgacttct taagcaagaa caaacagaac aaactatgga   40800
ggcttaaaca tggtctgaaa gatgttttca gtttgcatct taaacctgta gctaccatgc   40860
```

```
ccggcaccca ccaccacacc tggctaattt ttatattttt agtagagact gggttttacc   40920
atgttggcca ggctggtctt gaactcctga cctcagatga tccacccacc tcggcctccc   40980
aaagtgctgg gattacaagc gtgagccact gggcccagcc atagaaacac ttctgttttt   41040
tggggttttg ttgttgttgt tgttttttga cagagtctc cgctctgttg cccaggctgg   41100
agtgcagtgg cgcagtcttg gctcactgca agctcagcct cccgagtagc tgggaccaca   41160
ggcacccacc accacgtccg gctaattttt tgtattttta gtagagacag ggtttcactg   41220
tgttagccag gatagtctcg atctcatgac ctcgtgatcc acccacctca gcctcccaaa   41280
gtgctgggat tacaggcatg agccactgcg cctggccttt gggggttttt tttgagatgg   41340
agtctcactc tgttgcccag gctggagtgc agtggtatga tctcggctca ccacaacctc   41400
tgcctcgcaa gttcaagcaa ttctgcctta gcctcccaag taactgggat tacacgcatg   41460
caccaccaca cccatctaat tttatattt ttagtagaga cagggtttcc ctatgttggc   41520
caggctggtc ttgaactcct gacctcaggt aattcgccag cctcggcctc ccaaagtact   41580
gggattatag gcgtgagcca ccgagcccag cctagaatga cttcttaaga acaaaaagaa   41640
caaactatgg aggtttaaac atggtctaaa agatgttttc agtttgcatc ttaaacgtgt   41700
agccatcagt ttgttcagtg gggtcatttc tgtgagtagg taagagtgct gtggacagcg   41760
ggtatatcaa gttcacagtc cttgctcctt actcaaagcc tataattgct caggtaggtc   41820
attttggtgg gggacagcat gtgttgggaa ttgtgttcct ctatcaggtc caaacagctg   41880
ttgcaaggtc catgctcttg gaattaagac aaaacattga aaaatggggc aaattaccac   41940
ctcctctgtg ttcctacctg taaatccaca gtgttgcaca catttcattc cgtatcactg   42000
gtggtcaaaa aactcctggg accacctcag atttaaaaga attttgcttt ctagctttgg   42060
actctgatac tgtcctgtgt cttggggttt agttctcatg ttaatttatc ttaggtattg   42120
tatactaaga taattatatc tatacaagtc tgttccctcc tccagcgagc attcagatat   42180
ttataccttc ttttctttcc cctgccagga gttgatgggc agatctgtgt gaaactgtag   42240
tatcactgga ttacaagcaa aacccactct ttccttctgc atcagatgga aaagctcaat   42300
agcattcttg tttctttcag aacccacaat acattatatg caccagaaat gctagccaaa   42360
atggcagagc ctttcaccaa ggctctggat atgcttgacg cggaaaaatc tgctatatta   42420
ggtaagaaat gtaaccttt ttctcctaag gtttatctta tccctaatgg atgtcccctt   42480
ttttgttgtt tttaagagt catagtctct gtcacccagg ctagagtgca ctggtgcaac   42540
catagctcac tgtaggctca aactcttgga ctcaagcagt cttcctgcct cagcctcccg   42600
agtagttgga ccacaggcag atcacaacgc cagacgaact ttaaaatttt tttgttgaga   42660
cagagtcttg ctatgttgcc caggctggtc ttgaactctt atcatcaagc agtcctccca   42720
ccatggcctt taaagcacta gaatcctagt gattacaggc gttcttatgg gttccttgag   42780
cagcttcagc ctatcttgtg cttcttccat cttgtcttgc actgccttga ccatctatt   42840 gttcagaaat gcagaatgtg gagttcctat aagctctata tgaacaagtg tatttacttc   42900
attatcttag catacagaga aaatcgaagg caatttattt tttttcccg ttaacccctt   42960 cttcaattta gccagtaggt tgtggtgggt gttacagcca ttcaattata aataatcat   43020 ggcctttaac ctgaaggata tttgtatact ttcctgcctc ctcgtgtgtg tgtgtgtgtg   43080
tgtgtgtgtg tgtgtgtgtg tgtgtgtgtg tgtagatagg tatcaaagtt tttaaaggaa   43140 tagatttaa gccatttccc aattgttacc ttttttgttt tgttttgttt tcttgagaga   43200
gtctcactct gtcacccagg ctggtgtaca gtggtgcaat ctcagctcac tgcaacctct   43260
```

```
gccttccagg ttcaagtgat tctcccacag cctgctggga ctacaggcat gcaccatcac   43320
acccggctaa ttttttgtat ttttagtaga gacagggttt caccatgttg gctaggctgg   43380
tctcgaactc atgacctcaa gtgctctgcc tgccttggcc tcccaaagtg ccaggattat   43440
aggcatgagc caccacgcct ggccttccag ttgtgacctt gttaggatac tgctttaatt   43500
cattttccca ttgaaaataa gcatgaaaat aactgtgcag tcataattgt ggtatttgct   43560
gtgaaggaaa gtggcagggc tctgagtgtt tatcgggaga cctaacccag tctcagaggg   43620
aagtcagaag gctgactccc aatggggact tgaaggatga gtacgaacta gctaggttag   43680
gggcatgagg aaatgctggg cattctggac aaacagaatg gcaggtataa gatctgaggc   43740
aagagaaaaa ggccttggta tgtccagaac atagagatgg ttgaatcatg tggctggagc   43800
acagggagct agtctgggaa tgtgggatga agttagagct agaggcatca gttgtctaaa   43860
ccttgttccc atctcagaag cttcaggctg gctcaccatc acagccccca tagtttgtct   43920
ttgtcatcag ctataacctg tgtctgagcc cggctgtggt caagcaatcc aatggcattc   43980
ctcagctgtg aagttagcca aaggaaggat gttaatttgc ctttccagaa ctcatgtctg   44040
tctgtttcag cctagatagt cctgaatctt ttcctttgac accattccat ttaagggtta   44100
tgttgcagac accagtaaaa gtagaaattc caagaaatgt atagctatta atataaaaag   44160
taggtgttgc ttaccacaca cccccatgcc attattcaag ttaagtcagg aactcctgct   44220
atagaaataa gtggccaacc agaaatacta gaatggacaa acagttccca cagatagctt   44280
ctgactatag gactcgaaat gtaaaacctc tgattacact taaaaatata gatattttaa   44340
ggcagttttt aatactaagg taagtgggtt tcattttttag ctgctacaca tcttagtgtt   44400
ttgtgtaaga ttttgcttaa aaaagggggtt tcataactta attgtgggag catccccaga   44460
gctttatgga aaaatacttt tgagttgtca cttttttttgg tacaggttcc atctggggga   44520 aaaaaaaag cagataaaag agtacccggg tctaaagtcc tgggtcctta agtagctttc   44580
accttctcct accaaaagag tgcagcaaat cacgtagcca actgctttgc agtacagcac   44640
cagacatgca cacatcttca cccctgaaca acagcttcct gctgtagagt gttggccaat   44700
tgagactcct gacagtggag catcatgttc ttgacccgta tttccctgta ggattacctc   44760
aacctctctt ggaactcaat gactctcctg tcttcaaaac cgtcttggaa agaatgcagc   44820
gtttcttctc tacccctctat gaaaactggt aaggaaccaa tgctgcctct ccatattttc   44880
ttcctcgata tgtattgtat aggaatgtcc atgggttgga cttttcatct agtgtacagg   44940
taaggcgagg caagagtttg ataggaaact tatcattcta gtgttaaata gaaatgaaag   45000
cctgctttcc tgcatttgct ttttttgtaa ttgtcatatg agcctcacaa tcccagcctg   45060
cttcatgccc aacttgtctg tgtttctagt gtataaaatg atgaaaccca agtcgaagct   45120
aaaagtggtg gggattgctt agaccctaca ctgcttgcgg catacttctc ataggagtcg   45180
ggtggctgga tactggttgt gggttgggga ggtaactggc cctcatgggc tttggcctca   45240
ctaaccacta cactaatcag ccaagctaat gagatcgtcc attgtaagtc cacattaaat   45300
agtaatgaaa gctactgctg atctcggcca ccaacatctg tctttaaaaa gatgctgtat   45360
ctataagttc tcttaagtaa atacaactgc tcttctggct gaaaaacctt attgtaggct   45420
agaaatgaaa ttcatgggac agggctggca gtaacagatg ttggatttgt cattttcaat   45480 gctcttttttt tcccctttac agttttcata tcctagggaa ggcaggccct tccatgcagc   45540
aagacttcta tactgtggag gaccttgcta cccagcttct cagctcagcc tttgtcaact   45600
tgaacaatat tcctgactac cgactcagac ccatgcttca tatccttttca aaagtctcta   45660
```

```
cataacccaa aaggtcagaa aattagagag agaaacaaaa caggtcacag caaccagagg   45720
gaagaggcag aactggaagg aagagatgag attatgtatc taagtgtatc atgtcattaa   45780
aaacactggc agattgcagg gaaaacatga aggcagtcca gatggccata aacttttcct   45840
taggggtaaa ttttaccttt cccccttctc ggaattatta cagataaaac tttttttttt   45900
ttttgagaca gtcttgctca ctctgttgca caggctggag tgcagtggta tgatctcggc   45960
tcacagcttc tgcctctcag gttcaagcta ttcttgtgcc tcagcctcct aactagctgt   46020
gattacaggt gtgcaccatc acgcccagct gattttttatt cctattttt gagacagagt   46080 tttgctctat tgcccaggct ggagtgcagt ggcatgatct tgtcttactg caacttccac   46140
ctcctgggtt caagtgattc atgtgcctca gcctcccaag tagctgggat tacaggcgca   46200
tgctactacg cccagctaat tttttgtat ttttagtaga acaggttttt cgccatgttg   46260
gccaggctgg tctcaaactc ctgacctcaa gtaatccgcc tgcctcagcc tcccaaagtg   46320
ctggggttac aggtgtgagc caccatgccc agctgtgaaa gataaaactt ttatcccttt   46380
tctgtatttt tagaagcact tttttttttt tttttttgag acagggtctc agtgttaccc   46440
aggcaggaat gcagtggtgc catcaaagct cagtgcaggc tcaagtgatc ctcccacctc   46500
agcttcctga agagcctgga ctggaccaca gatgcgcacc accacaccca gctagttttt   46560
attattattt gtagagatgg gtctgtatta tgttccccag ggtggtctca aactcctggc   46620
tcaagtaatt ctcctgcctc agcctccaaa gtgctagaat tacaggcctg agccaccaca   46680
cccagccaga agcagcagtt ttaacacttc attctcattc agacccttat taatagttga   46740
atctctttct ttcttttctt tttttttttt tttgagacgg agtcttgctc tgttgcccag   46800
gctggagtgc agtggcgtga tctcggctca ctgcaagctt cgcctcccag gttcacacca   46860
ttctcttgcc ttagcttctc gagtagctgg gactacaggc gctcgccccc atgcccgact   46920 aattttttt tttttttttt tttttttag tagagacggg gtttcaccat gttagccagg   46980
atggtctcgc tctcttgacc ccgtgatcca ctcgccttgg cctcccaaag tgctgggatt   47040
acaggtgtga ccaccgcag ccagcaaatc tttcttacct gaaattataa ggagaatggt   47100
gaaggagagt ttgttacaag gatgtcctcc ttcctatttt tttattccta ctttttgggc   47160
cagtgaccat aatgtgcagc ctgacggaaa tgcagctaaa ctaagagtat aatggaattc   47220
aatatcagtg ccatttagga ttttaggaaa agaactttaa gatttttca ctgttaacac   47280 aggatatttt tgacatctgg caaatccttt agggattgat tctgcccagg ggtgcaaccc   47340
accacctggc aggtgagaga tgtgtgccta tgcactaaaa tttcttaact tgttgcagca   47400
cgtgtctttg taaagcctct ggtgctcttc tgtcccccag agcactatga agccctggta   47460
tcccccatcc tcggacctct tttcacctac ctccatatgg taagagataa gtcaggaaca   47520
ggaagcaaag agtactatta aggcctctgg ccatttctga gctttgcaag tcaggagctc   47580
ctagaagtgt tgtctactag ccctgccaga ctggctgggc agagcttcta ccccagctga   47640
ctatccttgc tgtaggatcg agcagccccc aaagaactaa actgatttaa ttgccacaag   47700
acagcttcag ttgcagattc tgctcctaac ctcctgttaa ctgaggagag gtaaaaagag   47760
gaatgcttgc tcacagaccc ttgccaggaa tgctgggtct gttatcctta ctctagaatt   47820 aagcagggg accagctggg tggagaacag gtatgtctag agacccagga attctaaaaa   47880
tgttgttaat tctttccaag caaagaggtg tttgagatac caccttcatc agggatgtgg   47940
gataggttac agaaaccata gatgtttttt ttaaccttgt ggtgtggagt ctacagaagt   48000
tgtcattgat gcctagaatc atccttggct aattttaatc atgaagtgga cttgactta   48060
```

```
gatattatgt gttccaatcc tttccccaat tctagcattt atttcctttg tgttttccca   48120
gaggctttct cagaaatggc aagttatcaa ccaaaggagc ctgctgtggt aagggatacc   48180
tacccactct tcttggtgga tgaactggca gccaggtttg gggtgggaaa aggaagcggg   48240
cagggattct gctgtcccag ggtagaagag cagtaggttg tagtcattct cagcctaggt   48300
gatacatggc ttgtctggac aggctgttac cagcaggcag actctgagat ccagccttca   48360 tagggctac tgttacctta ctcacttatt ttaattctgt aatgtctatc caactggaca    48420
gagtcactag taataatgtc cttcagtgga tcactgctgt ccattcccaa cttttgcata   48480
aaacgaagac ccaaaggaga agaaagtggt cagagagagt ctgattaggg tcgctgcttt   48540
ccttgtcctt cctttctgc actcctgtgg aacttggccc cctggttttc tgcagtggag     48600
aagatgaggc tgcagatgaa acccagagt ctcaagagat gctggaggag caactggtga     48660
ggatgttaac ccgagaagtc atggacctaa tcagtaagtg gcatgtcgaa actggggcta   48720
tagaggattt tcctggaaga agagctggtc gctcagccaa ctccatgaag gcctgactaa   48780
tgcaaaggat tcatgtttgc ggcgggcatg gtggattgcg aggtcaaaag atcaagacca   48840
tcctggccaa catggtgaaa ccctgtctct actaataata caaaaattag ctgggcgtag   48900
tggcgcgcag gcctgtagtc ccagctactc aggaggctga ggtaggagaa tcgcttgaac   48960 ccggaggcg gaggctgcag tgagccgaaa tcacgccact gcactccagc ctggcaaaag    49020
agtgaaactc cgtctcaaaa aaaaagttca tgtttgtagc aacactgaca gatccaaaag   49080
aaataactag atagaagcaa ggcagtcctt aagtcaacct aaggatactt tatgaattgc   49140
aagctgaata tggggaaaca aaaatagcag aaggaatttg gattcattag gaataacttc   49200
ctagttttgt caaaatagg aaatgtttta aattcttgga catggaggct gttaattttc    49260 ttttattt tactgtgtca ttttgtttgt ttgagattca aagtagacca gggatgtatc     49320
aagcatcctt tcctagtcac tcactctcag agaattctgt aatttctct cagctagttg    49380 aacttgaagg accaaaacag ttcggtcatc agaatgcctc tatttctatt ggtgaagcta   49440
attcttgtgc cttggacggt accccatct tcctccttcc tcacctggcc agagacaggt    49500
tgggatcagt gggcctgagg tggctgttgt ggtagtatat acccacccctt cacctagtaa  49560 ccctgctttc ttgctttagc ggtttgctgt gtttcaaaga agggtgctga ccacagtagt   49620
gctcccccag cagatggaga cggtaagtga gcctgtgaga ccttggagtt ctgctcttag   49680
cctcctaaat actgttcctt ctgaaccagg tcagtttcct tgcagtctgg tgaggagaag   49740
acaccttaca tgtagttatc atctctggac cagccctctt gctgtgtgcc tccatcatac   49800
tcccacctcc aagcctttgc acttgctgtt tcctctgtct cagatgattt cctcccaacc   49860
atatatgtga tctttctct tgctttattc caatgtcacc tcttcccaga gatcgtccat    49920
gaccaaccta tcaaaatgg caacccccagc tactctgtat tcctctgctt tattcttctt   49980
catagcagtt gtcactaccc aacattatgt ttttatttat gtattccttt cttacctatc   50040
tcccatgtta gaatgtaaac tcccatcagg gaagggacct attgtcctat acctttatc    50100 cccagtaact aaatcagtgt ctggtgctca aatatttgtc caacaacaaa gtaacttcag   50160
tatttgcagc attttgtgtt tctgcctaga agctcccatt tccctcatgt acagcttgag   50220
tgcatctcta aagatcagc catgggcatg gcattatgt ggaggtggga gggctcctag     50280
tactacttag ccaccactta gcctagaaca ctcagctttg ctttgttttt tgcgcttctg   50340
tcagaacaag atattcttct ctgttctgaa aggatggagc ttaacattct actctctgat   50400
aacagatgaa gaaatgatgg ccacagaggt cacccctca gctatggcag agcttacaga    50460
```

```
cctgggcaaa tgtctgatga agcatgaggt gggtagaagg agcaggtgat acctttactc   50520
cttgcccagg tggggagtca ccttttactt ttcttgctct atggtgctat caagagtttt   50580
ttgtaatact cctttgttac ataagttcct ggttccaaag gccccagaaa aaaccgaggg   50640
aaaaggtgca atgccatggt gtctcccata ccagcatagg caggagctct caggaaaaca   50700
catagtaggc acactgatgc agatccctgg tgtttagcct ccccaagcca ggcctgagct   50760
ttgtctccat cctacacata caggttttct cacattttga ttttttcttt ttgactggca   50820
atacacaaaa atagaggaag taaactcctt ttatttttcc tgcttagcta tttaaaactc   50880
cagctcctaa gccaggcatg gtggcacaca cctgtagtcc cagctattcg ggaggcttag   50940
atgggagaat agcttgagcc caggagttca ggaccagcct gggcaacaaa acaaacccat   51000
ctttagaggg ggggaggaaa aaaaaaaaac cctccggctc ctgatgtgta ataatcatca   51060
gagaaaactg tgcttctttt tccattgtaa ctcttcatct tttcctgttc aggatgtttg   51120
tacagcgcta ttaattacag ccttcaattc cctggcctgg aaagatactc tgtcctgcca   51180
gaggacaacc tcacagctct gctggcctct cctcaaacaa gtatggttat tcaccccttt   51240
tccctgcccc tcatgaagg tttgggtcat gcagactgac taaatcattc agaagaactg    51300
gggtgctgag gccttgagag aggcccctg tggccctaaa gcacagttgt ctccccaggt    51360
gctgtcaggg acactgctcg cagatgcagt tacgtggctt ttcaccagtg tgctgaaagg   51420
cttacagatg cacgggcagc acgacgggtg catggcttcc ctggtccatc tggccttcca   51480
gatatacgag gcactggtga gtggggaagg catgggggaa ggatggctgc agcttcatca   51540
ctcagtctgc tcctagtctc ttgggcctta tcctaaattc aggcacctgc caaattgctg   51600
gtgcaatctc tgagaaatgg gtgtggcagg aaatggggag ggtggcaata tccaaaccta   51660
catccagtaa gtttatccct gctgatatca gcgccccagg tacctggaga taagagctgt   51720
aatggagcaa atccctgaaa tacagaagga ctcactggac cagtttgact gcaagctttt   51780 aaaccctcc ctgcagaaag tggctgacaa gcgccgaaag gaccaattca aacgcctcat    51840
tgctggttgc attggggtag gtcatgcacc ttcaatagtg ctcccaaccc ccttcttaaa   51900
tcatgtgtat gggcaaacca taaaccagct gtagttattg accattatgg tgagattttt   51960
tttttttttt ttttgagatg gggtttcact cttgttgccc aggctggagt gcagtggtac   52020
gatctcagct caccacaacc tccgcctccc aggttcaaac gattctcctg cctcagcctc   52080
ccaagtagct gggattacag gcatgcacca ccacgtctgg ctacttttg tatttttagt    52140 agagacgggg tttctccatg tcggtcaggc tggtcttgaa ctcctgacct caggtgatcc   52200 acccgcttg gcctcccaaa agtgttggga ttacaggcgc gagccactgc gccgggccaa    52260
gagaatcttt taactactac tgagggccca gcattaattc tttctcattt gttttccaca   52320
gaaacccttg ggagagcagt tccgaaaaga agttcacatt aagaatcttc cctcactttt   52380
caaaaaaaca aagccaatgc tggagacgga ggtgctggac aatgatgggg gtggcctggc   52440
caccatcttt gaaccctgaa tcaagctttt gggcatcctt cctcggcctt tcttgtcatc   52500
tcttctttcc ctttgtagcc gatctctagg cccttcttgc actgccacct cactttccac   52560
cactgtcagc ctggaaagag atccaggtct ggagctggag agaacaggcc ctgtgcagga   52620
ccagaagtaa ttatactaaa gtatcaagaa agggagttag ggcttaaact attctgtcta   52680
gatgtcccag atagttccca ttctacttgg agatttggct tttccaagaa agctagagc   52740 agagcagccc ttctcccaca agccctccca cccccgtgca gccacatacc tgtacagaat   52800
ggtaactaag ggtgctgtgc ccaaccctgc gactagcaag gctcgcagca agagcacagc   52860
```

```
cctcaactac ttgtgccaga gtttctcttg gaccactcca actcccactg agcccttttg    52920
ctgctgggct ggcaggaaac tttccccact ccctaagggg catgtctggg ttaggtgcta    52980
agtgctgaag agaacttggt cagttctctc aactttgctt tgggcaagaa tctggtcacc    53040
tgatgggatc catggtacag gctactgcta aacttggcac agtatcaagt atagtacctc    53100
caaggaccag ggctgggaag tctttagtgc taacatcccc tttagagttc acacatcttg    53160
cccttccatg aatgacccct cagtctggcc tccccagcct caaggtccac tcaggcacaa    53220
gagccacagt accctagata gtgtcacatg acaccgttgt catccaagga taatacagac    53280
caactaggct acatctgtga tgagcagcta gcaaagccgc tggtcttctc ctaggactaa    53340
gtccaggtgc cttccacaat ctcatggtct ttcaggtccc tggttacttt tctcaaaggc    53400
catttccaaa agaatacatg ccttcacatc acaacctgta ctgtgagtcc attctagagg    53460
tcactgaaag gccctgtaaa gagaggacat ggatacggga cctggccctg aggttattac    53520
tggccgtaag gcagagttaa tccatacaga aaccagtgtg tccatgtgct ctgcacaaaa    53580
acagacctgt tgtccatcca gtccactgac aagagggttt ccccgagagc cgaagtggac    53640
tgaagctaca gttttagct ggtgcgggcc acaggcaggg tcagattgag aagaagcaaa    53700
gctggggaag cagaagttgg gagtcttgtg ttgctccctc ttcctgtgtg gtgctctggg    53760
tttctgtgga tcgtgaaggc gatctcaaga gtgtttccct ccaaacctga tagctgccta    53820
ttcctgtctg gttggggctg tggaggatgt agttgtattt attgcattgt aatattttta    53880
acatcctgtg acttcatgct agaaattttc tattgtttat agaaactttt tgtagaaaca    53940
ttaactctaa agcacatctg catgtcagta aaaatctcag tttcgtacag aaagggaccc    54000
atctgccttt ttcaacctag tcttaaaacc agtgacatac tccagggtta cttcatgagc    54060
acccgggact aaaacaggaa gaaatgtgac tgatgattct ggtctttcaa gctttctgaa    54120
atggtgtgcc agttagaaaa ggatttctat tcctgacata cccagactag gcagcccata    54180
ccattctcac agtgtctttc gtgtgtggct gctgggcctg gcccacagga attgctactg    54240
ttctttgttg gagctgtcaa tagcaacatg aacttccctg gtaaaccagg agataggtga    54300
agtggcacat tcactctagc ttgaatgttt ttctagggtt tggctgtgct cccagaaacc    54360
accttaattt gccaattctc aggaggtgtt ctt                                 54393
```

<210> SEQ ID NO 12
<211> LENGTH: 523
<212> TYPE: DNA
<213> ORGANISM: H. sapiens
<220> FEATURE:

<400> SEQUENCE: 12

```
gtgcgcagcg ccagcttctt cccagcgcga gttgctgcta acgctcctcc tccagcttcc        60 caccccgcc gcccgccgcg gcccggtacc aacgggtggt ctcgccgagg gagctgtcgt       120
gcctcgtggt cccgggactg cggtggtgtg cgctctcggc gcgtggcgct aggcatggcg       180
atggatcaag taaacgcgct gtgcgagcag ctggtgaaag cggtgacggt catgatggac       240
cccaactcca cccagcgcta ccggctggaa gccctcaagt tttgtgagga gtttaaagaa       300
aagtgtccta tctgtgtccc ctgtggcttg aggttggctg agaaaacaca agttgccatc       360
gtcagacatt ttggccttca gatcctggaa cacgttgtca gtttcggtg gaacggcatg        420 tctcgattgg agaaggtgta tctgaagaac agtgtcatgg agctgattgc aaatggaaca       480
ttgaacattt tggaagatga gaaccatatt aaagatgctc tgt                        523
```

```
<210> SEQ ID NO 13
<211> LENGTH: 20
<212> TYPE: DNA
<213> ORGANISM: Artificial Sequence
<220> FEATURE:
<223> OTHER INFORMATION: Antisense Compound

<400> SEQUENCE: 13
ttcctacacc aatagaaata                                              20

<210> SEQ ID NO 14
<211> LENGTH: 20
<212> TYPE: DNA
<213> ORGANISM: Artificial Sequence
<220> FEATURE:
<223> OTHER INFORMATION: Antisense Compound

<400> SEQUENCE: 14
caagaaccat gcagcctgat                                              20

<210> SEQ ID NO 15
<211> LENGTH: 20
<212> TYPE: DNA
<213> ORGANISM: Artificial Sequence
<220> FEATURE:
<223> OTHER INFORMATION: Antisense Compound

<400> SEQUENCE: 15
actagctcac cagcaatgca                                              20

<210> SEQ ID NO 16
<211> LENGTH: 20
<212> TYPE: DNA
<213> ORGANISM: Artificial Sequence
<220> FEATURE:
<223> OTHER INFORMATION: Antisense Compound

<400> SEQUENCE: 16
ttggaatctt cctgactcaa                                              20

<210> SEQ ID NO 17
<211> LENGTH: 20
<212> TYPE: DNA
<213> ORGANISM: Artificial Sequence
<220> FEATURE:
<223> OTHER INFORMATION: Antisense Compound

<400> SEQUENCE: 17
caggaatttc ctgtaacaaa                                              20

<210> SEQ ID NO 18
<211> LENGTH: 20
<212> TYPE: DNA
<213> ORGANISM: Artificial Sequence
<220> FEATURE:
<223> OTHER INFORMATION: Antisense Compound

<400> SEQUENCE: 18
tgacagcact ctgaaggttg                                              20

<210> SEQ ID NO 19
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 19
cactaagatg tgtagcagct                                                  20

<210> SEQ ID NO 20
<211> LENGTH: 20
<212> TYPE: DNA
<213> ORGANISM: Artificial Sequence
<220> FEATURE:
<223> OTHER INFORMATION: Antisense Compound

<400> SEQUENCE: 20
catgacctac cccaatgcaa                                                  20

<210> SEQ ID NO 21
<211> LENGTH: 20
<212> TYPE: DNA
<213> ORGANISM: Artificial Sequence
<220> FEATURE:
<223> OTHER INFORMATION: Antisense Compound

<400> SEQUENCE: 21
acaccactgc agtcccggga                                                  20

<210> SEQ ID NO 22
<211> LENGTH: 20
<212> TYPE: DNA
<213> ORGANISM: Artificial Sequence
<220> FEATURE:
<223> OTHER INFORMATION: Antisense Compound

<400> SEQUENCE: 22
atccatcgcc atgcctagcg                                                  20

<210> SEQ ID NO 23
<211> LENGTH: 20
<212> TYPE: DNA
<213> ORGANISM: Artificial Sequence
<220> FEATURE:
<223> OTHER INFORMATION: Antisense Compound

<400> SEQUENCE: 23
atgaccgtca ccgctttcac                                                  20

<210> SEQ ID NO 24
<211> LENGTH: 20
<212> TYPE: DNA
<213> ORGANISM: Artificial Sequence
<220> FEATURE:
<223> OTHER INFORMATION: Antisense Compound

<400> SEQUENCE: 24
ccatcatgac cgtcaccgct                                                  20

<210> SEQ ID NO 25
<211> LENGTH: 20
<212> TYPE: DNA
<213> ORGANISM: Artificial Sequence
<220> FEATURE:
<223> OTHER INFORMATION: Antisense Compound

<400> SEQUENCE: 25
gggcttccag ccggtagcgc                                                  20

<210> SEQ ID NO 26
<211> LENGTH: 20
<212> TYPE: DNA
```

```
<213> ORGANISM: Artificial Sequence
<220> FEATURE:
<223> OTHER INFORMATION: Antisense Compound

<400> SEQUENCE: 26
cttgagggct tccagccggt                                                    20

<210> SEQ ID NO 27
<211> LENGTH: 20
<212> TYPE: DNA
<213> ORGANISM: Artificial Sequence
<220> FEATURE:
<223> OTHER INFORMATION: Antisense Compound

<400> SEQUENCE: 27
caaaacttga gggcttccag                                                    20

<210> SEQ ID NO 28
<211> LENGTH: 20
<212> TYPE: DNA
<213> ORGANISM: Artificial Sequence
<220> FEATURE:
<223> OTHER INFORMATION: Antisense Compound

<400> SEQUENCE: 28
aaaatgtctg acgatggcaa                                                    20

<210> SEQ ID NO 29
<211> LENGTH: 20
<212> TYPE: DNA
<213> ORGANISM: Artificial Sequence
<220> FEATURE:
<223> OTHER INFORMATION: Antisense Compound

<400> SEQUENCE: 29
aggccaaaat gtctgacgat                                                    20

<210> SEQ ID NO 30
<211> LENGTH: 20
<212> TYPE: DNA
<213> ORGANISM: Artificial Sequence
<220> FEATURE:
<223> OTHER INFORMATION: Antisense Compound

<400> SEQUENCE: 30
tctgaaggcc aaaatgtctg                                                    20

<210> SEQ ID NO 31
<211> LENGTH: 20
<212> TYPE: DNA
<213> ORGANISM: Artificial Sequence
<220> FEATURE:
<223> OTHER INFORMATION: Antisense Compound

<400> SEQUENCE: 31
caggatctga aggccaaaat                                                    20

<210> SEQ ID NO 32
<211> LENGTH: 20
<212> TYPE: DNA
<213> ORGANISM: Artificial Sequence
<220> FEATURE:
<223> OTHER INFORMATION: Antisense Compound

<400> SEQUENCE: 32
atgacactgt tcttcagata                                                    20
```

```
<210> SEQ ID NO 33
<211> LENGTH: 20
<212> TYPE: DNA
<213> ORGANISM: Artificial Sequence
<220> FEATURE:
<223> OTHER INFORMATION: Antisense Compound

<400> SEQUENCE: 33
gctccatgac actgttcttc                                                    20

<210> SEQ ID NO 34
<211> LENGTH: 20
<212> TYPE: DNA
<213> ORGANISM: Artificial Sequence
<220> FEATURE:
<223> OTHER INFORMATION: Antisense Compound

<400> SEQUENCE: 34
tttctgctga ctgcaatgag                                                    20

<210> SEQ ID NO 35
<211> LENGTH: 20
<212> TYPE: DNA
<213> ORGANISM: Artificial Sequence
<220> FEATURE:
<223> OTHER INFORMATION: Antisense Compound

<400> SEQUENCE: 35
tgccttttct gctgactgca                                                    20

<210> SEQ ID NO 36
<211> LENGTH: 20
<212> TYPE: DNA
<213> ORGANISM: Artificial Sequence
<220> FEATURE:
<223> OTHER INFORMATION: Antisense Compound

<400> SEQUENCE: 36
aatctgcacc cagcaatgca                                                    20

<210> SEQ ID NO 37
<211> LENGTH: 20
<212> TYPE: DNA
<213> ORGANISM: Artificial Sequence
<220> FEATURE:
<223> OTHER INFORMATION: Antisense Compound

<400> SEQUENCE: 37
gcaagaaaag attccaggta                                                    20

<210> SEQ ID NO 38
<211> LENGTH: 20
<212> TYPE: DNA
<213> ORGANISM: Artificial Sequence
<220> FEATURE:
<223> OTHER INFORMATION: Antisense Compound

<400> SEQUENCE: 38
ggttgtgaaa gcaagaaaag                                                    20

<210> SEQ ID NO 39
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 39
tgcctgaaga gggctcccca                                                    20

<210> SEQ ID NO 40
<211> LENGTH: 20
<212> TYPE: DNA
<213> ORGANISM: Artificial Sequence
<220> FEATURE:
<223> OTHER INFORMATION: Antisense Compound

<400> SEQUENCE: 40
acgaagatat tttggtatta                                                    20

<210> SEQ ID NO 41
<211> LENGTH: 20
<212> TYPE: DNA
<213> ORGANISM: Artificial Sequence
<220> FEATURE:
<223> OTHER INFORMATION: Antisense Compound

<400> SEQUENCE: 41
gaagcacgaa gatattttgg                                                    20

<210> SEQ ID NO 42
<211> LENGTH: 20
<212> TYPE: DNA
<213> ORGANISM: Artificial Sequence
<220> FEATURE:
<223> OTHER INFORMATION: Antisense Compound

<400> SEQUENCE: 42
aagcccatct tgaccaagtt                                                    20

<210> SEQ ID NO 43
<211> LENGTH: 20
<212> TYPE: DNA
<213> ORGANISM: Artificial Sequence
<220> FEATURE:
<223> OTHER INFORMATION: Antisense Compound

<400> SEQUENCE: 43
aaggaaagcc catcttgacc                                                    20

<210> SEQ ID NO 44
<211> LENGTH: 20
<212> TYPE: DNA
<213> ORGANISM: Artificial Sequence
<220> FEATURE:
<223> OTHER INFORMATION: Antisense Compound

<400> SEQUENCE: 44
tttagaagga aagcccatct                                                    20

<210> SEQ ID NO 45
<211> LENGTH: 20
<212> TYPE: DNA
<213> ORGANISM: Artificial Sequence
<220> FEATURE:
<223> OTHER INFORMATION: Antisense Compound

<400> SEQUENCE: 45
tctgttttag aaggaaagcc                                                    20

<210> SEQ ID NO 46
<211> LENGTH: 20
<212> TYPE: DNA
```

```
<213> ORGANISM: Artificial Sequence
<220> FEATURE:
<223> OTHER INFORMATION: Antisense Compound

<400> SEQUENCE: 46
aaagcattga agtcctcatc                                              20

<210> SEQ ID NO 47
<211> LENGTH: 20
<212> TYPE: DNA
<213> ORGANISM: Artificial Sequence
<220> FEATURE:
<223> OTHER INFORMATION: Antisense Compound

<400> SEQUENCE: 47
tgaagaaagc attgaagtcc                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense Compound

<400> SEQUENCE: 48
ggagttgaag aaagcattga                                              20

<210> SEQ ID NO 49
<211> LENGTH: 20
<212> TYPE: DNA
<213> ORGANISM: Artificial Sequence
<220> FEATURE:
<223> OTHER INFORMATION: Antisense Compound

<400> SEQUENCE: 49
cgggaggagt tgaagaaagc                                              20

<210> SEQ ID NO 50
<211> LENGTH: 20
<212> TYPE: DNA
<213> ORGANISM: Artificial Sequence
<220> FEATURE:
<223> OTHER INFORMATION: Antisense Compound

<400> SEQUENCE: 50
agcatgtcaa aattgggcag                                              20

<210> SEQ ID NO 51
<211> LENGTH: 20
<212> TYPE: DNA
<213> ORGANISM: Artificial Sequence
<220> FEATURE:
<223> OTHER INFORMATION: Antisense Compound

<400> SEQUENCE: 51
tataaagcat gtcaaaattg                                              20

<210> SEQ ID NO 52
<211> LENGTH: 20
<212> TYPE: DNA
<213> ORGANISM: Artificial Sequence
<220> FEATURE:
<223> OTHER INFORMATION: Antisense Compound

<400> SEQUENCE: 52
ttggagagga gttgcttcac                                              20
```

```
<210> SEQ ID NO 53
<211> LENGTH: 20
<212> TYPE: DNA
<213> ORGANISM: Artificial Sequence
<220> FEATURE:
<223> OTHER INFORMATION: Antisense Compound

<400> SEQUENCE: 53
gctcattgga gaggagttgc                                                   20

<210> SEQ ID NO 54
<211> LENGTH: 20
<212> TYPE: DNA
<213> ORGANISM: Artificial Sequence
<220> FEATURE:
<223> OTHER INFORMATION: Antisense Compound

<400> SEQUENCE: 54
gccatcagct cctctaggaa                                                   20

<210> SEQ ID NO 55
<211> LENGTH: 20
<212> TYPE: DNA
<213> ORGANISM: Artificial Sequence
<220> FEATURE:
<223> OTHER INFORMATION: Antisense Compound

<400> SEQUENCE: 55
aagctcattc gtgcacggtt                                                   20

<210> SEQ ID NO 56
<211> LENGTH: 20
<212> TYPE: DNA
<213> ORGANISM: Artificial Sequence
<220> FEATURE:
<223> OTHER INFORMATION: Antisense Compound

<400> SEQUENCE: 56
cacaaaagct cattcgtgca                                                   20

<210> SEQ ID NO 57
<211> LENGTH: 20
<212> TYPE: DNA
<213> ORGANISM: Artificial Sequence
<220> FEATURE:
<223> OTHER INFORMATION: Antisense Compound

<400> SEQUENCE: 57
tccagagcct tggtgaaagg                                                   20

<210> SEQ ID NO 58
<211> LENGTH: 20
<212> TYPE: DNA
<213> ORGANISM: Artificial Sequence
<220> FEATURE:
<223> OTHER INFORMATION: Antisense Compound

<400> SEQUENCE: 58
cctgccttcc ctaggatatg                                                   20

<210> SEQ ID NO 59
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 59
aagggcctgc cttccctagg                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Compound

<400> SEQUENCE: 60
catggaaggg cctgccttcc                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Compound

<400> SEQUENCE: 61
tgctgcatgg aagggcctgc                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Compound

<400> SEQUENCE: 62
ggaatattgt tcaagttgac                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Compound

<400> SEQUENCE: 63
agtcaggaat attgttcaag                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Compound

<400> SEQUENCE: 64
agcacactgg tgaaaagcca                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Compound

<400> SEQUENCE: 65
ctttcagcac actggtgaaa                                              20

<210> SEQ ID NO 66
<211> LENGTH: 20
<212> TYPE: DNA
```

```
<213> ORGANISM: Artificial Sequence
<220> FEATURE:
<223> OTHER INFORMATION: Antisense Compound

<400> SEQUENCE: 66
tcgtgctgcc cgtgcatctg                                                    20

<210> SEQ ID NO 67
<211> LENGTH: 20
<212> TYPE: DNA
<213> ORGANISM: Artificial Sequence
<220> FEATURE:
<223> OTHER INFORMATION: Antisense Compound

<400> SEQUENCE: 67
accagggaag ccatgcaccc                                                    20

<210> SEQ ID NO 68
<211> LENGTH: 20
<212> TYPE: DNA
<213> ORGANISM: Artificial Sequence
<220> FEATURE:
<223> OTHER INFORMATION: Antisense Compound

<400> SEQUENCE: 68
tttaaaagct tgcagtcaaa                                                    20

<210> SEQ ID NO 69
<211> LENGTH: 20
<212> TYPE: DNA
<213> ORGANISM: Artificial Sequence
<220> FEATURE:
<223> OTHER INFORMATION: Antisense Compound

<400> SEQUENCE: 69
cccaagggtt tcccaatgca                                                    20

<210> SEQ ID NO 70
<211> LENGTH: 20
<212> TYPE: DNA
<213> ORGANISM: Artificial Sequence
<220> FEATURE:
<223> OTHER INFORMATION: Antisense Compound

<400> SEQUENCE: 70
tgaacttctt ttcggaactg                                                    20

<210> SEQ ID NO 71
<211> LENGTH: 20
<212> TYPE: DNA
<213> ORGANISM: Artificial Sequence
<220> FEATURE:
<223> OTHER INFORMATION: Antisense Compound

<400> SEQUENCE: 71
taatgtgaac ttcttttcgg                                                    20

<210> SEQ ID NO 72
<211> LENGTH: 20
<212> TYPE: DNA
<213> ORGANISM: Artificial Sequence
<220> FEATURE:
<223> OTHER INFORMATION: Antisense Compound

<400> SEQUENCE: 72
ggttcaaaga tggtggccag                                                    20
```

```
<210> SEQ ID NO 73
<211> LENGTH: 20
<212> TYPE: DNA
<213> ORGANISM: Artificial Sequence
<220> FEATURE:
<223> OTHER INFORMATION: Antisense Compound

<400> SEQUENCE: 73
ttcagggttc aaagatggtg                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Compound

<400> SEQUENCE: 74
cttgattcag ggttcaaaga                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Compound

<400> SEQUENCE: 75
aaaagcttga ttcagggttc                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense Compound

<400> SEQUENCE: 76
tgcccaaaag cttgattcag                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Compound

<400> SEQUENCE: 77
aaggatgccc aaaagcttga                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Compound

<400> SEQUENCE: 78
ggcctgttct ctccagctcc                                               20

<210> SEQ ID NO 79
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 79
aactcccttt cttgatactt                                              20

<210> SEQ ID NO 80
<211> LENGTH: 20
<212> TYPE: DNA
<213> ORGANISM: Artificial Sequence
<220> FEATURE:
<223> OTHER INFORMATION: Antisense Compound

<400> SEQUENCE: 80
gttaccattc tgtacaggta                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense Compound

<400> SEQUENCE: 81
ccaagagaaa ctctggcaca                                              20

<210> SEQ ID NO 82
<211> LENGTH: 20
<212> TYPE: DNA
<213> ORGANISM: Artificial Sequence
<220> FEATURE:
<223> OTHER INFORMATION: Antisense Compound

<400> SEQUENCE: 82
tcttgcccaa agcaaagttg                                              20

<210> SEQ ID NO 83
<211> LENGTH: 20
<212> TYPE: DNA
<213> ORGANISM: Artificial Sequence
<220> FEATURE:
<223> OTHER INFORMATION: Antisense Compound

<400> SEQUENCE: 83
ctatacttga tactgtgcca                                              20

<210> SEQ ID NO 84
<211> LENGTH: 20
<212> TYPE: DNA
<213> ORGANISM: Artificial Sequence
<220> FEATURE:
<223> OTHER INFORMATION: Antisense Compound

<400> SEQUENCE: 84
cttggaggta ctatacttga                                              20

<210> SEQ ID NO 85
<211> LENGTH: 20
<212> TYPE: DNA
<213> ORGANISM: Artificial Sequence
<220> FEATURE:
<223> OTHER INFORMATION: Antisense Compound

<400> SEQUENCE: 85
gctgctcatc acagatgtag                                              20

<210> SEQ ID NO 86
<211> LENGTH: 20
<212> TYPE: DNA
```

```
<213> ORGANISM: Artificial Sequence
<220> FEATURE:
<223> OTHER INFORMATION: Antisense Compound

<400> SEQUENCE: 86
ccgtatccat gtcctctctt                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Compound

<400> SEQUENCE: 87
aaactgtagc ttcagtccac                                               20

<210> SEQ ID NO 88
<211> LENGTH: 20
<212> TYPE: DNA
<213> ORGANISM: Artificial Sequence
<220> FEATURE:
<223> OTHER INFORMATION: Antisense Compound

<400> SEQUENCE: 88
ttctcaatct gaccctgcct                                               20

<210> SEQ ID NO 89
<211> LENGTH: 20
<212> TYPE: DNA
<213> ORGANISM: Artificial Sequence
<220> FEATURE:
<223> OTHER INFORMATION: Antisense Compound

<400> SEQUENCE: 89
gatgtgcttt agagttaatg                                               20

<210> SEQ ID NO 90
<211> LENGTH: 20
<212> TYPE: DNA
<213> ORGANISM: Artificial Sequence
<220> FEATURE:
<223> OTHER INFORMATION: Antisense Compound

<400> SEQUENCE: 90
ctcgcgctgg gaagaagctg                                               20

<210> SEQ ID NO 91
<211> LENGTH: 20
<212> TYPE: DNA
<213> ORGANISM: H. sapiens
<220> FEATURE:
<223> OTHER INFORMATION: target sequence

<400> SEQUENCE: 91
atcaggctgc atggttcttg                                               20

<210> SEQ ID NO 92
<211> LENGTH: 20
<212> TYPE: DNA
<213> ORGANISM: H. sapiens
<220> FEATURE:
<223> OTHER INFORMATION: target sequence

<400> SEQUENCE: 92
ttgagtcagg aagattccaa                                               20
```

```
<210> SEQ ID NO 93
<211> LENGTH: 20
<212> TYPE: DNA
<213> ORGANISM: H. sapiens
<220> FEATURE:
<223> OTHER INFORMATION: target sequence

<400> SEQUENCE: 93
agctgctaca catcttagtg                                                    20

<210> SEQ ID NO 94
<211> LENGTH: 20
<212> TYPE: DNA
<213> ORGANISM: H. sapiens
<220> FEATURE:
<223> OTHER INFORMATION: target sequence

<400> SEQUENCE: 94
tcccgggact gcagtggtgt                                                    20

<210> SEQ ID NO 95
<211> LENGTH: 20
<212> TYPE: DNA
<213> ORGANISM: H. sapiens
<220> FEATURE:
<223> OTHER INFORMATION: target sequence

<400> SEQUENCE: 95
cgctaggcat ggcgatggat                                                    20

<210> SEQ ID NO 96
<211> LENGTH: 20
<212> TYPE: DNA
<213> ORGANISM: H. sapiens
<220> FEATURE:
<223> OTHER INFORMATION: target sequence

<400> SEQUENCE: 96
gtgaaagcgg tgacggtcat                                                    20

<210> SEQ ID NO 97
<211> LENGTH: 20
<212> TYPE: DNA
<213> ORGANISM: H. sapiens
<220> FEATURE:
<223> OTHER INFORMATION: target sequence

<400> SEQUENCE: 97
agcggtgacg gtcatgatgg                                                    20

<210> SEQ ID NO 98
<211> LENGTH: 20
<212> TYPE: DNA
<213> ORGANISM: H. sapiens
<220> FEATURE:
<223> OTHER INFORMATION: Target sequence

<400> SEQUENCE: 98
accggctgga agccctcaag                                                    20

<210> SEQ ID NO 99
<211> LENGTH: 20
<212> TYPE: DNA
<213> ORGANISM: H. sapiens
<220> FEATURE:
<223> OTHER INFORMATION: Target sequence
```

```
<400> SEQUENCE: 99
ttgccatcgt cagacatttt                                               20

<210> SEQ ID NO 100
<211> LENGTH: 20
<212> TYPE: DNA
<213> ORGANISM: H. sapiens
<220> FEATURE:
<223> OTHER INFORMATION: Target sequence

<400> SEQUENCE: 100
atcgtcagac attttggcct                                               20

<210> SEQ ID NO 101
<211> LENGTH: 20
<212> TYPE: DNA
<213> ORGANISM: H. sapiens
<220> FEATURE:
<223> OTHER INFORMATION: Target sequence

<400> SEQUENCE: 101
attttggcct tcagatcctg                                               20

<210> SEQ ID NO 102
<211> LENGTH: 20
<212> TYPE: DNA
<213> ORGANISM: H. sapiens
<220> FEATURE:
<223> OTHER INFORMATION: Target sequence

<400> SEQUENCE: 102
gaagaacagt gtcatggagc                                               20

<210> SEQ ID NO 103
<211> LENGTH: 20
<212> TYPE: DNA
<213> ORGANISM: H. sapiens
<220> FEATURE:
<223> OTHER INFORMATION: Target sequence

<400> SEQUENCE: 103
ctcattgcag tcagcagaaa                                               20

<210> SEQ ID NO 104
<211> LENGTH: 20
<212> TYPE: DNA
<213> ORGANISM: H. sapiens
<220> FEATURE:
<223> OTHER INFORMATION: Target sequence

<400> SEQUENCE: 104
tgcagtcagc agaaaaggca                                               20

<210> SEQ ID NO 105
<211> LENGTH: 20
<212> TYPE: DNA
<213> ORGANISM: H. sapiens
<220> FEATURE:
<223> OTHER INFORMATION: Target sequence

<400> SEQUENCE: 105
tgcattgctg ggtgcagatt                                               20

<210> SEQ ID NO 106
<211> LENGTH: 20
<212> TYPE: DNA
```

```
<213> ORGANISM: H. sapiens
<220> FEATURE:
<223> OTHER INFORMATION: Target sequence

<400> SEQUENCE: 106
tacctggaat cttttcttgc                                               20

<210> SEQ ID NO 107
<211> LENGTH: 20
<212> TYPE: DNA
<213> ORGANISM: H. sapiens
<220> FEATURE:
<223> OTHER INFORMATION: Target sequence

<400> SEQUENCE: 107
tggggagccc tcttcaggca                                               20

<210> SEQ ID NO 108
<211> LENGTH: 20
<212> TYPE: DNA
<213> ORGANISM: H. sapiens
<220> FEATURE:
<223> OTHER INFORMATION: Target sequence

<400> SEQUENCE: 108
taataccaaa atatcttcgt                                               20

<210> SEQ ID NO 109
<211> LENGTH: 20
<212> TYPE: DNA
<213> ORGANISM: H. sapiens
<220> FEATURE:
<223> OTHER INFORMATION: Target sequence

<400> SEQUENCE: 109
ccaaaatatc ttcgtgcttc                                               20

<210> SEQ ID NO 110
<211> LENGTH: 20
<212> TYPE: DNA
<213> ORGANISM: H. sapiens
<220> FEATURE:
<223> OTHER INFORMATION: Target sequence

<400> SEQUENCE: 110
ggctttcctt ctaaaacaga                                               20

<210> SEQ ID NO 111
<211> LENGTH: 20
<212> TYPE: DNA
<213> ORGANISM: H. sapiens
<220> FEATURE:
<223> OTHER INFORMATION: Target sequence

<400> SEQUENCE: 111
ctgcccaatt ttgacatgct                                               20

<210> SEQ ID NO 112
<211> LENGTH: 20
<212> TYPE: DNA
<213> ORGANISM: H. sapiens
<220> FEATURE:
<223> OTHER INFORMATION: Target sequence

<400> SEQUENCE: 112
gtgaagcaac tcctctccaa                                               20
```

```
<210> SEQ ID NO 113
<211> LENGTH: 20
<212> TYPE: DNA
<213> ORGANISM: H. sapiens
<220> FEATURE:
<223> OTHER INFORMATION: Target sequence

<400> SEQUENCE: 113
gcaactcctc tccaatgagc                                              20

<210> SEQ ID NO 114
<211> LENGTH: 20
<212> TYPE: DNA
<213> ORGANISM: H. sapiens
<220> FEATURE:
<223> OTHER INFORMATION: Target sequence

<400> SEQUENCE: 114
ttcctagagg agctgatggc                                              20

<210> SEQ ID NO 115
<211> LENGTH: 20
<212> TYPE: DNA
<213> ORGANISM: H. sapiens
<220> FEATURE:
<223> OTHER INFORMATION: Target sequence

<400> SEQUENCE: 115
aaccgtgcac gaatgagctt                                              20

<210> SEQ ID NO 116
<211> LENGTH: 20
<212> TYPE: DNA
<213> ORGANISM: H. sapiens
<220> FEATURE:
<223> OTHER INFORMATION: Target sequence

<400> SEQUENCE: 116
tgcacgaatg agcttttgtg                                              20

<210> SEQ ID NO 117
<211> LENGTH: 20
<212> TYPE: DNA
<213> ORGANISM: H. sapiens
<220> FEATURE:
<223> OTHER INFORMATION: Target sequence

<400> SEQUENCE: 117
cctagggaag gcaggccctt                                              20

<210> SEQ ID NO 118
<211> LENGTH: 20
<212> TYPE: DNA
<213> ORGANISM: H. sapiens
<220> FEATURE:
<223> OTHER INFORMATION: Target sequence

<400> SEQUENCE: 118
gcaggccctt ccatgcagca                                              20

<210> SEQ ID NO 119
<211> LENGTH: 20
<212> TYPE: DNA
<213> ORGANISM: H. sapiens
<220> FEATURE:
<223> OTHER INFORMATION: Target sequence
```

```
<400> SEQUENCE: 119
gtcaacttga acaatattcc                                              20

<210> SEQ ID NO 120
<211> LENGTH: 20
<212> TYPE: DNA
<213> ORGANISM: H. sapiens
<220> FEATURE:
<223> OTHER INFORMATION: Target sequence

<400> SEQUENCE: 120
cttgaacaat attcctgact                                              20

<210> SEQ ID NO 121
<211> LENGTH: 20
<212> TYPE: DNA
<213> ORGANISM: H. sapiens
<220> FEATURE:
<223> OTHER INFORMATION: Target sequence

<400> SEQUENCE: 121
tggcttttca ccagtgtgct                                              20

<210> SEQ ID NO 122
<211> LENGTH: 20
<212> TYPE: DNA
<213> ORGANISM: H. sapiens
<220> FEATURE:
<223> OTHER INFORMATION: Target sequence

<400> SEQUENCE: 122
cagatgcacg ggcagcacga                                              20

<210> SEQ ID NO 123
<211> LENGTH: 20
<212> TYPE: DNA
<213> ORGANISM: H. sapiens
<220> FEATURE:
<223> OTHER INFORMATION: Target sequence

<400> SEQUENCE: 123
gggtgcatgg cttccctggt                                              20

<210> SEQ ID NO 124
<211> LENGTH: 20
<212> TYPE: DNA
<213> ORGANISM: H. sapiens
<220> FEATURE:
<223> OTHER INFORMATION: Target sequence

<400> SEQUENCE: 124
tgcattggga aacccttggg                                              20

<210> SEQ ID NO 125
<211> LENGTH: 20
<212> TYPE: DNA
<213> ORGANISM: H. sapiens
<220> FEATURE:
<223> OTHER INFORMATION: Target sequence

<400> SEQUENCE: 125
cagttccgaa aagaagttca                                              20

<210> SEQ ID NO 126
<211> LENGTH: 20
<212> TYPE: DNA
```

```
<213> ORGANISM: H. sapiens
<220> FEATURE:
<223> OTHER INFORMATION: Target sequence

<400> SEQUENCE: 126
ccgaaaagaa gttcacatta                                               20

<210> SEQ ID NO 127
<211> LENGTH: 20
<212> TYPE: DNA
<213> ORGANISM: H. sapiens
<220> FEATURE:
<223> OTHER INFORMATION: Target sequence

<400> SEQUENCE: 127
ctggccacca tctttgaacc                                               20

<210> SEQ ID NO 128
<211> LENGTH: 20
<212> TYPE: DNA
<213> ORGANISM: H. sapiens
<220> FEATURE:
<223> OTHER INFORMATION: Target sequence

<400> SEQUENCE: 128
caccatcttt gaaccctgaa                                               20

<210> SEQ ID NO 129
<211> LENGTH: 20
<212> TYPE: DNA
<213> ORGANISM: H. sapiens
<220> FEATURE:
<223> OTHER INFORMATION: Target sequence

<400> SEQUENCE: 129
tctttgaacc ctgaatcaag                                               20

<210> SEQ ID NO 130
<211> LENGTH: 20
<212> TYPE: DNA
<213> ORGANISM: H. sapiens
<220> FEATURE:
<223> OTHER INFORMATION: Target sequence

<400> SEQUENCE: 130
gaaccctgaa tcaagctttt                                               20

<210> SEQ ID NO 131
<211> LENGTH: 20
<212> TYPE: DNA
<213> ORGANISM: H. sapiens
<220> FEATURE:
<223> OTHER INFORMATION: Target sequence

<400> SEQUENCE: 131
ctgaatcaag cttttgggca                                               20

<210> SEQ ID NO 132
<211> LENGTH: 20
<212> TYPE: DNA
<213> ORGANISM: H. sapiens
<220> FEATURE:
<223> OTHER INFORMATION: Target sequence

<400> SEQUENCE: 132
tcaagctttt gggcatcctt                                               20
```

```
<210> SEQ ID NO 133
<211> LENGTH: 20
<212> TYPE: DNA
<213> ORGANISM: H. sapiens
<220> FEATURE:
<223> OTHER INFORMATION: Target sequence

<400> SEQUENCE: 133
ggagctggag agaacaggcc                                               20

<210> SEQ ID NO 134
<211> LENGTH: 20
<212> TYPE: DNA
<213> ORGANISM: H. sapiens
<220> FEATURE:
<223> OTHER INFORMATION: Target sequence

<400> SEQUENCE: 134
tacctgtaca gaatggtaac                                               20

<210> SEQ ID NO 135
<211> LENGTH: 20
<212> TYPE: DNA
<213> ORGANISM: H. sapiens
<220> FEATURE:
<223> OTHER INFORMATION: Target sequence

<400> SEQUENCE: 135
tgtgccagag tttctcttgg                                               20

<210> SEQ ID NO 136
<211> LENGTH: 20
<212> TYPE: DNA
<213> ORGANISM: H. sapiens
<220> FEATURE:
<223> OTHER INFORMATION: Target sequence

<400> SEQUENCE: 136
caactttgct ttgggcaaga                                               20

<210> SEQ ID NO 137
<211> LENGTH: 20
<212> TYPE: DNA
<213> ORGANISM: H. sapiens
<220> FEATURE:
<223> OTHER INFORMATION: Target sequence

<400> SEQUENCE: 137
tggcacagta tcaagtatag                                               20

<210> SEQ ID NO 138
<211> LENGTH: 20
<212> TYPE: DNA
<213> ORGANISM: H. sapiens
<220> FEATURE:
<223> OTHER INFORMATION: Target sequence

<400> SEQUENCE: 138
tcaagtatag tacctccaag                                               20

<210> SEQ ID NO 139
<211> LENGTH: 20
<212> TYPE: DNA
<213> ORGANISM: H. sapiens
<220> FEATURE:
<223> OTHER INFORMATION: Target sequence
```

<400> SEQUENCE: 139
ctacatctgt gatgagcagc                                               20

<210> SEQ ID NO 140
<211> LENGTH: 20
<212> TYPE: DNA
<213> ORGANISM: H. sapiens
<220> FEATURE:
<223> OTHER INFORMATION: Target sequence

<400> SEQUENCE: 140
aagagaggac atggatacgg                                               20

<210> SEQ ID NO 141
<211> LENGTH: 20
<212> TYPE: DNA
<213> ORGANISM: H. sapiens
<220> FEATURE:
<223> OTHER INFORMATION: Target sequence

<400> SEQUENCE: 141
cattaactct aaagcacatc                                               20

<210> SEQ ID NO 142
<211> LENGTH: 19
<212> TYPE: DNA
<213> ORGANISM: random sequence
<220> FEATURE:
<223> OTHER INFORMATION: Antisense Compound

<400> SEQUENCE: 142
cgagaggcgg acgggaccg                                                19

<210> SEQ ID NO 143
<211> LENGTH: 21
<212> TYPE: DNA
<213> ORGANISM: random sequence
<220> FEATURE:
<223> OTHER INFORMATION: Antisense Compound

<400> SEQUENCE: 143
cgagaggcgg acgggaccgt t                                             21

<210> SEQ ID NO 144
<211> LENGTH: 21
<212> TYPE: DNA
<213> ORGANISM: random sequence
<220> FEATURE:
<223> OTHER INFORMATION: Antisense Compound

<400> SEQUENCE: 144
cggtcccgtc cgcctctcgt t                                             21

<210> SEQ ID NO 145
<211> LENGTH: 19
<212> TYPE: DNA
<213> ORGANISM: random sequence
<220> FEATURE:
<223> OTHER INFORMATION: Antisense Compound

<400> SEQUENCE: 145
cgagaggcgg acgggaccg                                                19

<210> SEQ ID NO 146
<211> LENGTH: 19
<212> TYPE: DNA

-continued

```
<213> ORGANISM: random sequence
<220> FEATURE:
<223> OTHER INFORMATION: Antisense Compound

<400> SEQUENCE: 146
gctctccgcc tgccctggc                                              19
```